(12) United States Patent
Kerwin et al.

(10) Patent No.: US 6,720,344 B2
(45) Date of Patent: Apr. 13, 2004

(54) METHODS AND COMPOSITIONS FOR STIMULATING OSTEOBLAST PROLIFERATION OR TREATING MALIGNANT CELL PROLIFERATION AND METHODS FOR SELECTING OSTEOBLAST PROLIFERATION STIMULANTS

(75) Inventors: Sean M. Kerwin, Round Rock, TX (US); Laurence H. Hurley, Austin, TX (US); Mark R. DeLuca, Round Rock, TX (US); Bob M. Moore, III, Nesbit, MS (US); Gregory R. Mundy, San Antonio, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 10/108,606

(22) Filed: Mar. 27, 2002

(65) Prior Publication Data

US 2003/0119791 A1 Jun. 26, 2003

Related U.S. Application Data

(63) Continuation of application No. 09/230,208, filed as application No. PCT/US97/10643 on Jun. 20, 1997, now abandoned.
(60) Provisional application No. 60/016,088, filed on Jun. 20, 1996.

(51) Int. Cl.[7] ............... A61K 31/428; C07D 277/82
(52) U.S. Cl. ............... 514/367; 514/375; 548/163
(58) Field of Search ................. 514/367, 375; 548/163

(56) References Cited

U.S. PATENT DOCUMENTS

| | | | |
|---|---|---|---|
| 3,629,284 A | 12/1971 | Yamamoto et al. | 260/326.13 |
| 4,054,574 A | 10/1977 | Wu et al. | 548/163 |
| 4,332,727 A | 6/1982 | Boltze et al. | 548/501 |
| 4,450,167 A | 5/1984 | Le Martret et al. | 424/258 |
| 4,607,053 A | 8/1986 | Karanewsky et al. | 514/575 |
| 4,675,331 A * | 6/1987 | Kume et al. | 514/367 |
| 4,874,864 A | 10/1989 | Schnur et al. | 546/153 |
| 4,929,623 A | 5/1990 | Abe et al. | 514/293 |
| 4,970,318 A | 11/1990 | Schnur et al. | 546/198 |
| 5,154,931 A | 10/1992 | Kruger et al. | 424/549 |
| 5,166,161 A | 11/1992 | Kokura et al. | 514/314 |
| 5,322,847 A | 6/1994 | Marfat et al. | 514/303 |
| 5,362,742 A | 11/1994 | Meguro et al. | 514/312 |
| 5,389,646 A | 2/1995 | Labroo | 514/320 |
| 5,430,144 A | 7/1995 | Schoen et al. | 540/461 |
| 5,468,587 A | 11/1995 | Bailey et al. | 430/203 |
| 5,545,735 A | 8/1996 | Bochis et al. | 540/490 |
| 5,550,134 A | 8/1996 | Audia et al. | 514/284 |
| 5,565,408 A | 10/1996 | Hagen et al. | 504/104 |
| 5,635,197 A | 6/1997 | Audia et al. | 424/423 |
| 5,780,300 A | 7/1998 | Artavanis-Tsakonas et al. | 435/377 |
| 5,843,618 A | 12/1998 | Bailey et al. | 430/203 |
| 5,892,007 A | 4/1999 | Ramage | 536/23.1 |
| 5,929,232 A | 7/1999 | Jacobsen et al. | 540/145 |
| 5,943,585 A | 8/1999 | May et al. | 438/400 |
| 5,945,365 A | 8/1999 | Reddy | 502/117 |
| 6,034,066 A | 3/2000 | Johnson et al. | 514/18 |
| 6,057,341 A | 5/2000 | Charpentier | 514/337 |
| 6,060,449 A | 5/2000 | Hamuro et al. | 514/12 |
| 6,060,567 A | 5/2000 | Lai et al. | 526/126 |
| 6,077,669 A | 6/2000 | Little et al. | 435/6 |

FOREIGN PATENT DOCUMENTS

| | | |
|---|---|---|
| DE | 2133649 | 1/1972 |
| EP | 0168309 | 1/1986 |
| EP | 221211 | 5/1987 |
| EP | 0223141 | 5/1987 |
| EP | 0261459 | 3/1988 |
| EP | 0295656 | 12/1988 |
| EP | 0343894 | 11/1989 |
| EP | 395 093 | 10/1990 |
| EP | 404 440 | 12/1990 |
| EP | 0499242 | 8/1992 |
| EP | 0584952 | 3/1994 |
| EP | 0617030 | 9/1994 |
| EP | 0674903 | 10/1995 |
| EP | 0712628 | 5/1996 |
| FR | 2583404 | 12/1986 |
| JP | 01203325 | 8/1989 |
| JP | 03130216 | 8/1991 |
| WO | WO 89/03830 | 5/1989 |
| WO | WO 90/15052 | 12/1990 |
| WO | WO 94/03432 | 2/1994 |
| WO | WO 94/22463 | 10/1994 |
| WO | WO 97/15308 | 5/1997 |

OTHER PUBLICATIONS

Chen et al. Journal of Cell Biology 142(1):295–305 (1998).

Eckhardt et al., Proc. Nat'l Acad. Sci. USA 91:6674–6678 (1994).

Eyrolles et al., J. Med. Chem. 37: 1508–1517 (1994).

Ghosh–Choudhury et al., Endocrinology 137:331–339 (1996).

Gori et al. J. Bone Miner. Res. 14(9): 1522–1535 (1999) (Abstract) at <http://www.ncbi.nlm.nih.gov> (visited Jul. 31, 2001).

Houghton et al. Bone 22(1):7–16 (1998) (Abstract) at <http://www.ncbi.nlm.nih.gov> (visited Jul. 31, 2002).

Kamala et al., Indian J. Chem. 22B:1194–96 (1983).

(List continued on next page.)

Primary Examiner—Joseph K. McKane
Assistant Examiner—Kamal Saeed
(74) Attorney, Agent, or Firm—Morrison & Foerster LLP

(57) ABSTRACT

The present invention relates to methods for stimulating osteoblast proliferation and methods for selecting pharmacologically active compounds useful for stimulating osteoblast proliferation.

7 Claims, 3 Drawing Sheets

OTHER PUBLICATIONS

Kirshenbaum et al., Cancer res. 54:2199–2206 (1994).
Lee et al. Mol. Cell. Biol. 20(23):8783–8792 (2000) (Abstract) at <http://www.ncbi.nlm.nih.gov> (visited Jul. 31, 2001).
Marfat et al., Chemical Abstracts 117:782—Abst. #90279j. (1992).
*The Merck Index* (9$^{th}$ Ed.); Rahway, NJ pp. 182,894,901, 1058,1080,1239 (1976).
Rickard et al. J. Bone Miner. Res. 11(3):312–324 (1996) (Abstract) at <http://www.ncbi.nlm.nih.gov> (visted Jul. 31, 2002).
Rosen et al., J. Med. Chem. (1995) 38(25):4855–4874.
Stedman's Medical Dictionary (26$^{th}$ Ed.) Williams & Wilkins pp. 1267 (2000).
Takashi et al., Jpn. Kokai Tokyo Koho, #JP03130216 A2, Jun. 4, 1994.
Yamada et al. Histochem. J. 31(10):687–694 (1999) (Abstract) at <http://www.ncbi.nlm.nih.gov> (visited Jul. 31, 2001).
Waisser et al., Collect. Czech. Chem. Commun. 56:2978–2985 (1991).

* cited by examiner

METHODS AND COMPOSITIONS FOR STIMULATING OSTEOBLAST PROLIFERATION OR TREATING MALIGNANT CELL PROLIFERATION AND METHODS FOR SELECTING OSTEOBLAST PROLIFERATION STIMULANTS

The present application is a continuation of U.S. patent application Ser. No. 09/230,208, filed Jan. 20, 1999, now abandoned, which is a 371 application of PCT/US97/10643, filed Jun. 20, 1997, which claims priority benefit of U.S. Provisional Patent Application Serial No. 60/016,088 filed Jun. 20, 1996. The contents of the above applications are incorporated by reference in their entirety.

FIELD OF THE INVENTION

The present invention relates to compounds and their use for the treatment of nuclear hormone receptor (NHR) family associated disorders. More specifically, the present invention relates to compounds having a particular 3-dimensional spatial orientation that are capable of binding to and thus altering the function of NHRs. Such compounds would be useful as therapeutic agents for disorders associated with NHRs such as the retinoid x receptor (RXR). The invention also relates to compositions and methods for the treatment or prophylaxis of osteoporosis, bone loss, arthritis, inflammation, cancer and skin conditions.

BACKGROUND OF THE INVENTION AND DESCRIPTION OF THE PRIOR ART

Modern day methods for the discovery of therapeutic agents for the amelioration of major diseases center on the interdisciplinary approaches of molecular biology, enzymology, crystallography, drug synthesis, molecular modeling and pharmacology. The typical approach involves: identification, isolation, purification, and crystallization of a target protein associated with the disease(s) of interest; modeling the protein binding and active sites; and modeling, synthesizing and evaluating compounds to optimize their pharmacological activity. Even with the advanced state of the art, drug discovery and, in particular, prediction of structure-activity relationships continue to require significant effort on the part of the pharmaceutical industry. Thus, the need to develop efficient and cost effective methods for the identification of pharmacologically active compounds for the treatment specific diseases still remains.

Osteoporosis is a condition characterized by a decrease in bone mass with decreased density and enlargement of bone spaces, producing porosity and fragility. This condition afflicts both men and women, particularly menopausal women, with advancing age. This condition is primarily a disorder in the formation of bone matrix. Osteoblasts, the bone-forming population of cells, are typically reduced in number. Osteoblasts are derived from adjacent mesenchymal precursors in a process regulated by local bone-derived factors. Osteoclasts, a population of cells that break down bone and that are associated with bone resorption, are not reduced in number. Osteoclasts are large, usually multinuclear cells found on the resorbing surfaces of mineralized bone. Osteoclasts are formed by fusion of mononuclear precursors, originating from extraskeletal blood-born precursors.

All known and local stimulators of osteoclastic bone resorption, including parathyroid hormone, 1, 25D, IL-2, and TNF, modulate their stimulatory effects on the osteoclast through an initial effect on osteoblasts. Osteoblasts are therefor believed to play a major role in regulating bone turnover by controlling the rate of new bone formation, as well as by serving to generate signals that stimulate osteoclastic bone resorption.

NHR families are associated with the modulation of mammalian cell proliferation and differentiation. These cellular processes are controlled by signal molecules that regulate gene expression. NHRs such as retinoid receptors are associated with many diseases and disorders such as osteoporosis, cancer, acne, AIDS, arthritis, psoriasis, lupus erythematosus and the like. The retinoid x receptor (RXR) serves to modulate cellular transcriptional activity thereby controlling cellular proliferation.

It is recognized in the art that osteoblasts play a very complex role in the formation of bone. It is generally thought that osteoclasts serve to dissolve (resorb) bone so that osteoblasts can then deposit more bone. It is reasonable then that compounds which can either inhibit the excessive resorption of bone or stimulate the proliferation of osteoblasts will be useful for the prevention of bone loss or the stimulation of bone growth.

Takashi et al. (Jpn. Kokai Tokyo Koho JP03130216 A2, Jun. 4, 1994) discloses diphenyl compounds having the following general structure

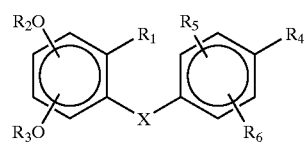

where X is —$CH_2$— or —C(=O)—, for the treatment and prophylaxis of osteoporosis.

Labroo (U.S. Pat. No. 5,389,646 issued Feb. 14, 1995) discloses compounds having the following general structure

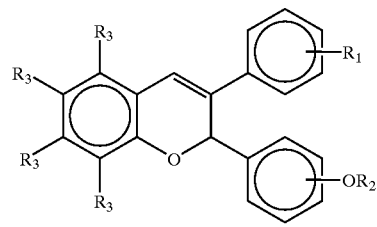

where $R_1$ is H, OH, C1–C17 alkoxy, (C1–C17) alkylcarbonyloxy, (C1–C17)alkylcarbonylamino or (C1–C17)alkylcarbonyl; $R_2$ is —$(CH_2)_{(1-6)}$—$CH_2$-heterocycle; and $R_3$ is H, OH, C1–C17 alkoxy, (C1–C17) alkylcarbonyloxy, (C1–C17)alkylcarbonylamino or (C1–C17)alkylcarbonyl, for the treatment and prevention of bone loss.

Other compounds such as the one below

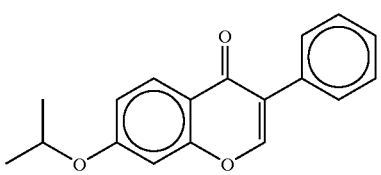

have been proposed for the treatment of osteoporosis. Even so, those compounds have not found general use due to their limited efficacy. Thus, the need for more efficacious compounds for the treatment of osteoporosis still remains.

Kamala et al. (*Indian J. Chem.* (1983), 22B, 1194–96) and Waisser et al. (Collect. Czech. *Chem. Commun.* (1991), 56, 2978–2985) disclose the synthesis of

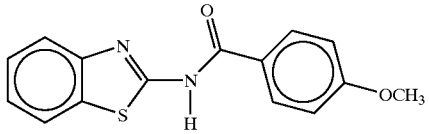

and its uses as a synthetic intermediate and anti-tuberculotic agent, respectively.

Bis-aromatic compounds are widely known for their use in the treatment of cancer and tumors. Such compounds generally effectively inhibit DNA replication thereby exerting their cytotoxic effect upon mammalian cells. Here too, no compound has been found to be generally applicable for the treatment of a broad spectrum of cancers and tumors. Thus, the need for more efficacious broader spectrum anti-cancer and tumoricidal compounds still remains.

It is an object of the present invention to overcome the limitations inherent in the art of modeling pharmaceutical agents by providing a method for selecting candidate chemical agents using defined 3-dimensional spatial characteristics. These spatially defined chemical compounds in some aspects further overcome limitations associated with available osteogenic agents by providing agents that stimulate production of bone morphogenic proteins, and thus provide compositions useful for stimulating osteoblast proliferation and in diseases which result in bone loss.

A further object of the invention is to provide agents that bind other receptors in the nuclear hormone receptor (NHR) family that are associated with diseases.

It is another object of the present invention to provide a method of using particular pharmacologically active compounds for the treatment or prophylaxis of physiological disorders or diseases associated with NHRs such as osteoporosis, arthritis, cancer, tumors and the like.

It is another object of the present invention to provide a method for the selection of pharmacologically active compounds which are capable of stimulating osteoblast proliferation and differentiation and are useful for the treatment of physiological disorders associated with NHRs and in particular diseases associated with bone loss.

Another object of the present invention is to provide methods for selecting and screening for pharmacologically active compositions which are capable of stimulating osteoblast proliferation and differentiation activity. Such selected composition would be used for the treatment or prophylaxis of osteoporosis and other physiological disorders associated with NHRS.

SUMMARY OF THE INVENTION

The present invention provides methods of stimulating osteoblast proliferation, as well as methods for selecting pharmacologically active compounds. In one embodiment, the method for stimulating osteoblast proliferation comprises selecting substances of the general formula I

X—L—Z, wherein:

X is selected from the group consisting of:

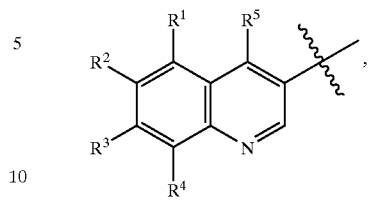

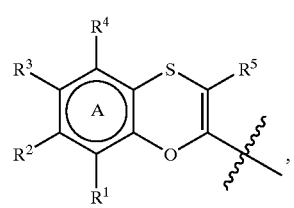

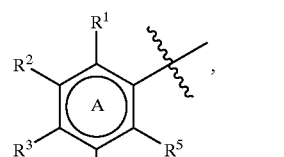

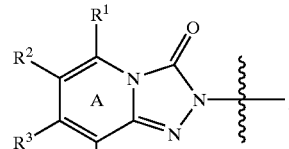

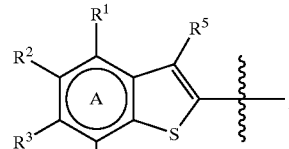

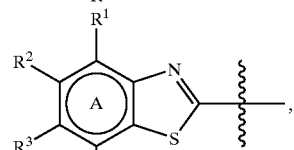

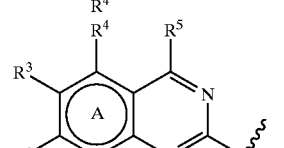

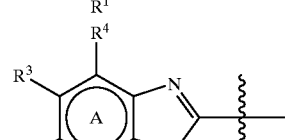

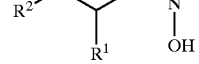 or

-continued

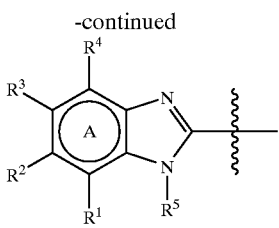

L is selected from the group consisting of:

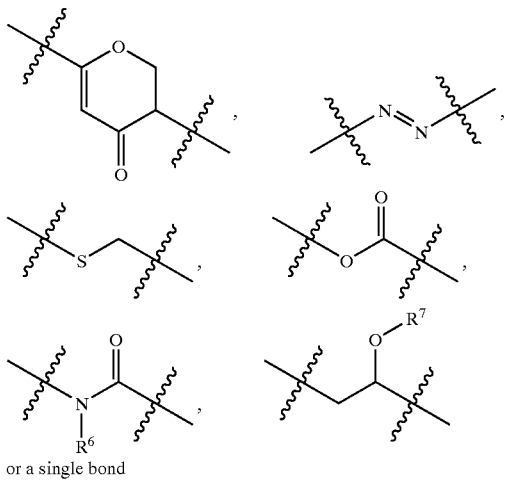

or a single bond

Z is selected from the group consisting of:

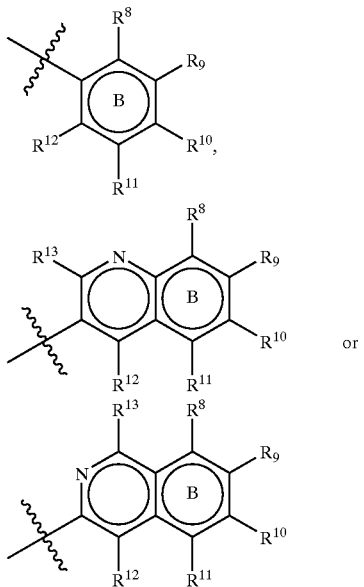

wherein $R^1$ is selected from the group consisting of:
  H, OH, C1–C4 alkyl, C1–C4 alkoxy, C1–C4 alkylthio, halo and (C1–C12)alkyl-carbonyloxy;
$R^2$ is selected from the group consisting of:
  H, OH, halo, C1–C6 alkyl, C1–C6 alkenyl, C1–C6 alkoxy and (C1–C12)alkyl-carbonyloxy;
$R^3$ is selected from the group consisting of:
  H, OH, halo, C1–C6 alkyl, C1–C6 alkoxy, C1–C6 alkenyl and (C1–C12)alkyl-carbonyloxy;
$R^4$ is selected from the group consisting of:
  H, OH, halo, C1–C6 alkyl, C1–C6 alkoxy and (C1–C12)alkyl-carbonyloxy;
$R^5$ is selected from the group consisting of:
  H, halo, C1–C6 alkyl, C1–C6 alkoxy, —OC(=O)Me, phthalimide and (C1–C12)alkyl-carbonyloxy;
$R^6$ is selected from the group consisting of:
  H, OH, —NH$_2$, C1–C4 alkyl and C1–C4 alkoxy;
$R^7$ is selected from the group consisting of:
  H, C1–C4 alkyl, (C1–C4)alkyl-carbonyl and (C7–C10) arylalkyl;
$R^8$ is selected from the group consisting of:
  H, OH, halo, —CF$_3$, C1–C4 haloalkyl, C1–C4 alkyl, C1–C4 alkoxy, —NHC(=O)Me and —N(C1–C4 alkyl)$_2$;
$R^9$ is selected from the group consisting of:
  H, OH, halo, —CN, —NO$_2$, C1–C4 haloalkyl, —CF$_3$, C1–C8 alkyl, C1–C8 alkoxy, —NHC(=O)Me and —OC(=O)Me;
$R^{10}$ is selected from the group consisting of:
  H, OH, halo, —CN, —NO$_2$, C1–C4 haloalkyl, —CO$_2$H, C1–C12 alkyl, C1–C12 alkoxy, phenyl, C1–C12 alkenyl, (C1–C4)alkoxycarbonyl, —NHC(=O)Me, (C1–C4)alkylcarbonyl, (C1–C12)alkylcarbonyloxy and heteroaryl;
$R^{11}$ is selected from the group consisting of:
  H, OH, halo, C1–C4 haloalkyl, —CF$_3$, C1–C4 alkyl, —NH$_2$, C1–C4 alkoxy, —NHC (=O)Me, C1–C4 alkenyl, (C1–C4)alkoxycarbonyl, (C1–C4) alkylcarbonyl, and (C1–C4)alkylcarbonyloxy;
$R^{12}$ is selected from the group consisting of:
  H, OH, —NR$_2$, C1–C4 alkyl, C1–C4 alkoxy, and (C1–C4 alkylcarbonyl; and
$R^{13}$ is selected from the group consisting of:
  H, OH, halo, —NH$_2$, C1–C4 alkyl, C1–C4 alkoxy, —N(C1–C4 alkyl)$_2$; and
exposing cells comprising osteoblast cells to an effective amount of the pharmacologically active compound.

These methods are expected to result in the stimulation of osteoblast proliferation, and hence a useful application in the prevention of bone loss and/or promotion of bone growth.

In further defined embodiments, the substance selected as part of the method is more particularly defined in that $R^{10}$ and $R^{11}$ may join together to form a 5–7 membered carbocycle or oxacarbocycle fused to the ring to which they are attached, where the carbocycle and oxacarbocycle are substituted with one or more groups independently selected from the group consisting of:
  C1–C4 alkyl, C1–C4 alkoxy, OH, halo, carboxyl, H and aryl, to provide a pharmacologically active compound.

It is also contemplated and within the scope of the invention that the pharmacologically active compound of the formula I may bind more than one different type of nuclear hormone receptor (NHR), and hence be useful in treatment of other NHR related diseases.

While not intending to be limited to any particular mechanism of action, it is contemplated that the pharmacologically active compound of the formula I may promote osteoblast growth or enrich osteoblast population by enhancing BMP-2 promoter activity.

It is also contemplated and within the scope of the present invention that pharmacologically active compounds of the formula I may be used in combination with other compounds for the stimulation or promotion of osteoblast growth. They may also be used for, the stimulation of bone growth or the inhibition of bone loss and/or bone resorption.

Another aspect of the present invention provides a method for selecting a pharmacologically active compound or candidate pharmacologically active compounds. In one embodiment, the pharmacological activity of the compounds is a capacity for stimulating BMP-2 promoter activity. The method in one embodiment comprises:

selecting candidate compounds having a spatially defined 3-dimensional structure as in formula II W—L—Y    Formula II wherein:
W contains an aromatic group having a centroid indicated by the letter "A";
Y contains a carbocyclic group having a centroid indicated by the letter "B";
L is a group linking X and Z;
a plane "P" is formed by the aromatic atoms of the aromatic group in W;
the centroid "B" lies within about 1, or about 0.7 angstroms above or below the plane "P";
the centroid "A" and the centroid "B" are spaced apart by about 6, or about 6.6, to about 8, or about 8.5 angstroms;
to provide spatially defined molecules; and
selecting spatially defined molecules capable of stimulating BMP-2 promoter activity.

The spatially defined molecules in the above method are further defined in some embodiments as having at least two hydrogen bond accepting groups located either within or in close proximity to L, the hydrogen bond accepting groups being further defined as follows:

1) the hydrogen bond accepting groups are within about 2, or about 2.3, to about 5, or about 5.4 angstroms apart;
2) one hydrogen bond accepting group is about 4, or about 4.5, to about 7, or about 7.7 angstroms from centroid "A" and about 2, or about 2.7, to about 3, or about 3.8 angstroms from centroid "B"; and
3) one hydrogen bond accepting group is about 2, or about 2.6, to about 3, or about 3.8 angstroms, from centroid "A" and about 4, or about 4.6, to about 7, or about 6.9 angstroms from centroid "B".

In some embodiments of the method, L is further defined as occupying a space which outer limit is less than or equal to about 3, preferably about 3.1 angstroms, as measured by heavy atom distance, above or below and normal to the plane "P" as measured along a normal to the plane "P". In other embodiments, L may be even further defined as occupying a space which outer limit is about 4, preferably about 4.7 to about 6.0 angstroms, as measured by heavy atom distance, perpendicular to a line connecting centroid "A" to centroid "B" and within the plane "P".

Pharmaceutically acceptable preparations of these compounds are also claimed, and are used to provide a pharmacologically active preparation for stimulating osteoblast proliferation and/or reducing bone resorption.

It is contemplated and within the scope of the present invention that the pharmacologically active compound of the formula II may possess activities other than stimulation of osteoblast proliferation and inhibiting bone resorption. Such activities would generally be associated with binding to one or more nuclear hormone receptors, and in so doing providing a treatment for various other diseases that are associated with receptor activity.

It is also contemplated and within the scope of the present invention that many pharmacologically active compounds not specifically enumerated herein may nonetheless fall within the spatially defined structure of formula II. Such spatially defined molecules would also fall within the scope of the method, where they are capable of stimulating BMP-2 promoter activity, or stimulating osteoblast proliferation, or some other desired pharmacological activity. These compounds thus would have utility in stimulating bone formation or reducing the loss of bone tissue.

It should be understood that a compound of the formula II may also contain other structural parameters not recited herein, yet fall within the defined scope of the invention. Such other structural parameters are generally secondary to those recited. That is, although addition of a particular substituent to either W or Y may render a compound of formula II more or less active than without that particular substituent, the compound having the substituent is within the scope of the present method as long as it comprises the characteristics recited above for the compound of formula II, or any of the formulas as described here.

Another embodiment of the present invention provides a method for treating and/or preventing malignant cell proliferation one embodiment of the method comprises:

administering to a population of cells comprising malignant cells a malignant cell proliferation inhibiting amount of a pharmacologically active compound having a spatially defined structure as defined by formula II W—L—Y; and    Formula II inhibiting malignant cells, wherein the pharmacologically active compound is further defined by a 3-dimensional structure wherein:
W contains an aromatic group having a centroid indicated by the letter "A";
Y contains a carbocyclic group having a cenzvroid indicated by the letter "B";
L is a group linking X and Z;
a plane "P" is formed by the aromatic atoms of the aromatic group in W;
the centroid "B" lies within about 1, or about 0.7 angstroms above or below the plane "P", and
the controid "A" and the centroid "B" are about 6, or 6.6 to about 8, or about 8.5 angstroms apart.

The pharmacologically active compound of the above method may be further defined as having a spatially defined structure wherein at least two hydrogen bond accepting groups are located either within or in close proximity to L, with the hydrogen bond accepting groups being further defined as follows;

1) the hydrogen bond accepting groups are within about 2, or about 2.3, to about 5, or about 5.4 angstroms apart;
2) one hydrogen bond accepting group is about 4, or about 4.5, to about 7, or about 7.7 angstroms from centroid "A" and about 2, or about 2.7, to about 3, or about 3.8, angstroms from centroid "B"; and
3) one hydrogen bond accepting group is about 2, or about 2.6, to about 3, or about 3.8, angstroms from centroid "A" and about 4, or about 4.6 to about 6, or about 6.9 angstroms from centroid "B".

In some embodiments of the method, L is further defined as occupying a space which outer limit is less than or equal to about 2.5, or about 3 or 3.1 angstroms, as measured by heavy atom distance, above or below and normal to the plane "P" as measure along a normal to the plane "P". In yet another embodiment, the pharmacologically active compound is further defined wherein L occupies a space which outer limit is about 4, or preferably about 4.7 to about 5, or preferably 6.0 angstroms, as measured by heavy atom distance, perpendicular to a line connecting centroid "A" to centroid "B" and within the plane "P".

Other aspects of the present invention provide methods of stimulating BMP-2 promoter activity or osteoblast proliferation and pharmacologically active compounds of the formula III

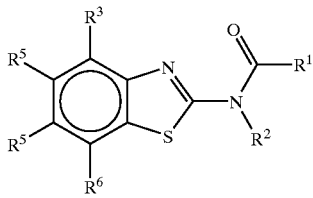

Formula III wherein:
R$^1$ is selected from the group consisting of:
   aryl, naphthyl, heteroaryl, cycloalkyl, cycloalkenyl, azacycloalkyl, oxacycloalkyl, azacycloalkenyl, oxacycloalkenyl, keto substituted cycloalkyl, and keto substituted cycloalkenyl, where each of the above substituents is substituted by one or more of the groups independently selected from the group consisting of:
   C1–C7 alkyl, C1–C7 alkoxy, benzyloxy, hydroxy, C1–C2 haloalkyl, halo, cyano, carboxyl, hydrogen, (C1–C4)alkoxycarbonyl, —N(C1–C4 alkyl)$_2$, (C1–C4)alkylcarbonyloxy, aryl, (C1–C4) alkylcarbonylamino, (C1–C4)alkylcarbonyl, (C1–C4)alkyl-aryl, and —NH$_2$;
R$^2$ is selected from the group consisting of:
   H, C1–C4 alkyl, C1–C4 alkenyl, C1–C4 alkynyl, C1–C4 alkoxy and —NH$_2$;
R$^3$ and R$^6$ are selected from the group consisting of:
   H, hydroxy, halo, (C1–C5)alkylcarbonyloxy, cyano, C1–C4 alkyl, C1–C4 alkenyl and C1–C4 alkoxy;
R$^4$ and R$^5$ are selected from the group consisting of:
   H, halo, hydroxy, (C1–C4)alkyl-carbonyloxy, cyano, C1–C2 haloalkyl, C1–C4 alkoxy, benzoyl, (C1–C4) alkyl-aryl, (C1–C6)alkylaminocarbonyloxy, phenylaminocarbonyloxy, C1–C4 alkyl, C1–C4 alkenyl, C1–C4 alkynyl, (C1–C4)alkenyl-aryl, (C1–C4)alkynyl-aryl, (C1–C4)alkyl-(C6–C10) cycloalkyl, (C1–C4)alkenyl-(C6–C10)cycloalkyl, (C1–C4)alkynyl-(C6–C10)cycloalkyl, (C1–C4)alkyl-(C6–C10)cycloalkenyl, (C1–C4)alkenyl-(C6–C10) cycloalkenyl, (C1–C4)alkynyl-(C6–C10)cycloalkenyl, carboxy and (C1–C4)alkoxycarbonyl.

The method generally comprises administering an effective amount of a compound of the formula III to cells comprising osteoblasts or osteoblast precursor cells.

Further defined embodiments of the method for stimulating BMP-2 promoter activity or osteoblast proliferation employ compounds of the type described above wherein R$^3$ and R$^4$ join together to form a 5–7 membered carbocycle or oxacarbocycle fused to the ring to which they are attached, where the carbocycle or oxacarbocycle is substituted by one or more of the groups selected from the group consisting of: C1–C4 alkyl, C1–C4 alkoxy, hydroxy, halo, carboxyl, hydrogen and aryl.

In alternative embodiments of the method, the pharmacologically active compound is defined as follows:
   R$^4$ and R$^5$ join together to form a 5–7 membered carbocycle or oxacarbocycle fused to the ring to which they are attached, where the carbocycle or oxacarbocycle is substituted by one or more of the groups selected from the group consisting of: C1–C4 alkyl, C1–C4 alkoxy, hydroxy, halo, carboxyl, hydrogen and aryl.

In yet another alternative embodiment, the pharmacologically active compound is further defined wherein:
   R$^5$ and R$^6$ join together to form a 5–7 membered carbocycle or oxacarbocycle fused to the ring to which they are attached, where the carbocycle or oxacarbocycle is substituted by one or more of the groups selected from the group consisting of: C1–C4 alkyl, C1–C4 alkoxy, hydroxy, halo, carboxyl, hydrogen and aryl.

Another aspect of the present invention comprises a pharmacologically active composition possessing osteoblast proliferation activity. In some embodiments, the composition is defined by reference to a particularly defined process comprising:
   oxidizing a compound of the formula VI

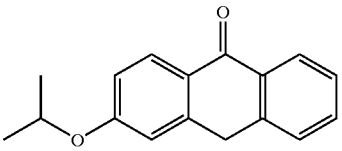

Formula VI with either heat or CrO$_3$/H$_2$O/AcOH for a period of time sufficient to form the pharmacologically active composition. This preparation may be further purified and the most active fractions selected. Compositions provided as a result of the above process and having an ED$_{50}$ of about 1 to about 50 μg/ml, as measured using the assay as described in Example 1, are expected to possess osteoblast proliferation activity and a capacity for stimulating BMP-2 promoter activity.

It is contemplated and within the scope of the present invention that the above process may comprise other similar or equivalent processes which will effect the conversion of the compound of the formula VI to a desired composition having the defined pharmacological activity. Such methods do not depart from the spirit or scope of the present invention.

It is also contemplated and within the scope of the present invention that the pharmacologically active composition so prepared will be useful in the treatment or prophylaxis of diseases or disorders associated with tumor cell proliferation, arthritis, inflammation, bone resorption, skin conditions, and diseases that may be treated employing receptor-directed therapies.

Other features, advantages and embodiments of the invention will be apparent to those skilled in the art from the following description, accompanying data and appended claims.

BRIEF DESCRIPTION OF THE DRAWINGS

The following drawings form part of the present specification and are included to further demonstrate certain aspects of the invention. The invention may be better understood by reference to one or more of these drawings in combination with the detailed description of specific embodiments presented herein.

DETAILED DESCRIPTION OF THE INVENTION

Figure 1:
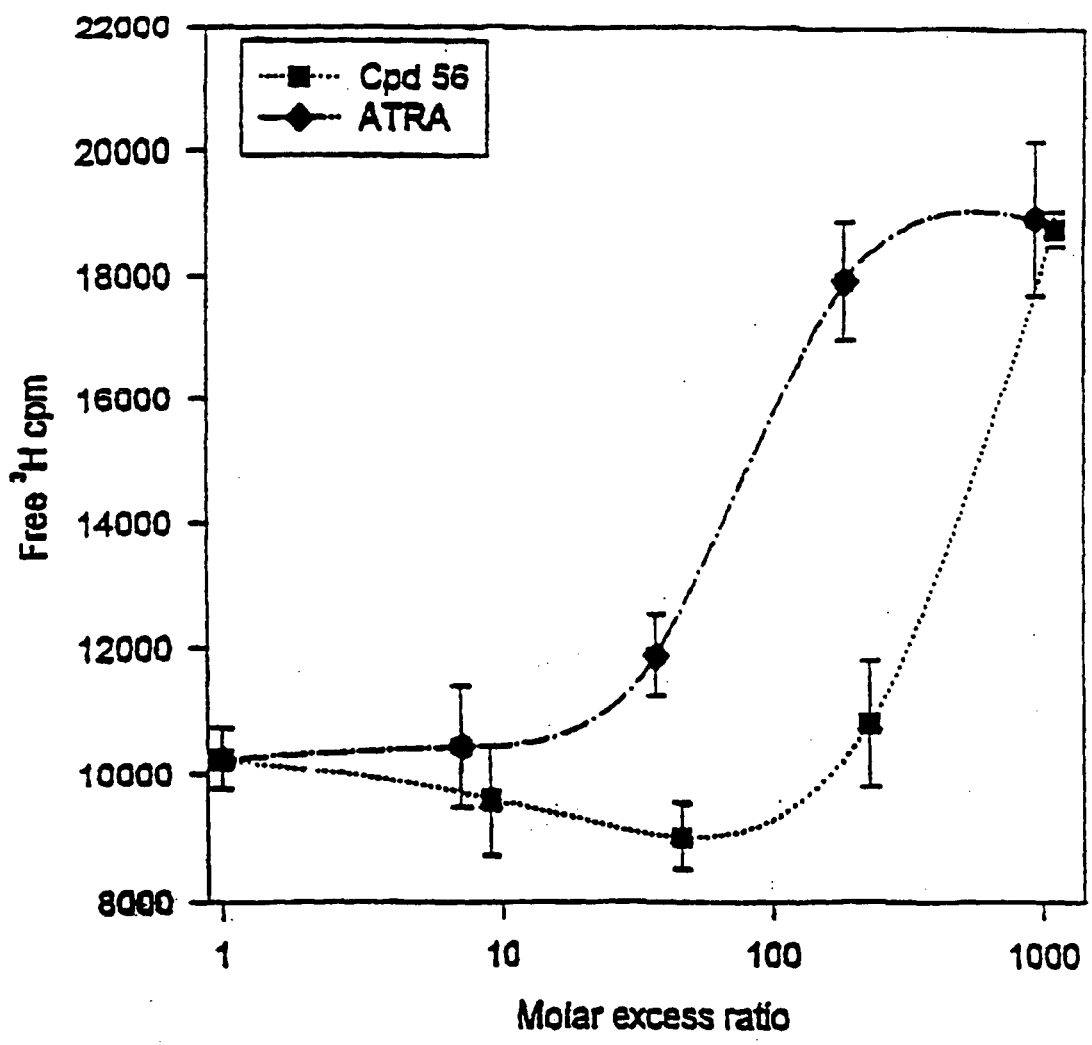
FIG. 1. A plot showing the results obtained from a retinoic acid displacement assay.

Method for the Selection of Pharmacologically Active Compounds

The present invention relates, among other things, to methods for the selection of a pharmacologically active compound or compounds from a group of compounds. Selected compounds will possess the herein defined spatial chemical structure, and have an observable capability for stimulating osteoblast proliferation or maintaining osteoblast growth in culture.

The chemical structure of the selected compound can be defined using the following structural and spatial parameters. The spatial parameters may be obtained by determining the 3-dimensional structure of the selected compounds. Methods useful for 3-dimensional structure determination include: single crystal x-ray diffraction or 2-dimensional to 3-dimensional conversion algorithms such as CONCORD or molecular mechanics (MM2). The selected compound will possess two hydrophobic groups exemplified by an aromatic group and a carbocyclic, or alternatively a heterocyclic, group. Each of these two hydrophobic groups can be described by a centroid, the position of which is simply the average position of all of the atoms in the hydrophobic group. For compounds that possess the desired activity, the distance between these two centroids will fall into the range of about 7, or about 7.9 to about 8, or about 8.5 Å. In addition to these two hydrophobic groups, compounds displaying the desired activity will possess a chemical grouping or substituent that is capable of forming a hydrogen bond or of serving as a Lewis base. One can formally associate with this hydrogen bond acceptor or Lewis basic site in the molecule, a hydrogen bond donating or Lewis acidic group that is external to the molecule. This external hydrogen bond donating group or Lewis acidic group will be oriented relative to the molecule in such a way as to make chemical contact with the complementary site on the molecule. In this way, the external site will be placed at a distance between 2 and 4 Å from the complementary site on the molecule, and in such a way as to form hydrogen bonding or Lewis acid/base associations. A certain geometric relationship must hold between the two hydrophobic groups and the external hydrogen bond donating/Lewis acidic site. This geometric relationship can be described in terms of distances and angles. The external site will be asymmetrically disposed with respect to the two hydrophobic groups, such that one hydrophobic group (the distal hydrophobic group) is farther away from the external site than the other (proximal) hydrophobic group. For compounds possessing the desired activity, the distance between the external hydrogen bond donating/Lewis acidic group and the centroid describing the distal hydrophobic group will fall within the range of about 6, or about 6.7 to about 7, or about 7.7 Å, and will optimally fall within the range of about 6, or about 6.8 to about 7, or about 7.7 Å. For s compounds possessing the desired activity, the distance between this external site and the centroid describing the proximal hydrophobic site will fall within the range of about 4, or about 4.6, to about 6, or about 6.3, Å, and will optimally be within the range of about 4, or about 4.9, to about 6.0 Å. In addition to the groups already described, compounds possessing the desired activity will also possess a second group capable of serving as a hydrogen bond donor or as a Lewis base.

An angle can be used to describe the relative orientation of this second hydrogen bond accepting/Lewis basic site in the molecule. This angle is that formed between the centroid describing the distal hydrophobic group, this second hydrogen bond accepting group, and the external hydrogen bond donating/Lewis acidic group. For compounds that possess the desired activity, this angle will fall within the range 74 to 112 degrees, and will optimally be within the range 85 to 89 degrees.

Figure 2:
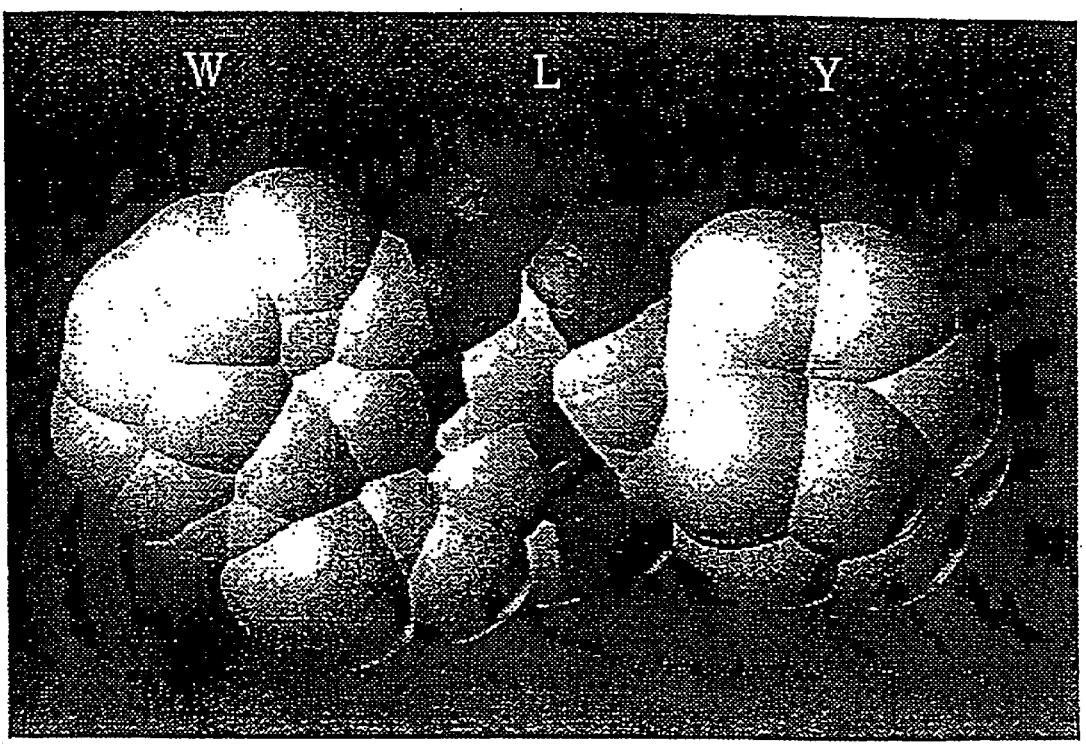
FIG. 2. A top view of a space filling model of one embodiment of a compound of the formula II.
Figure 3:
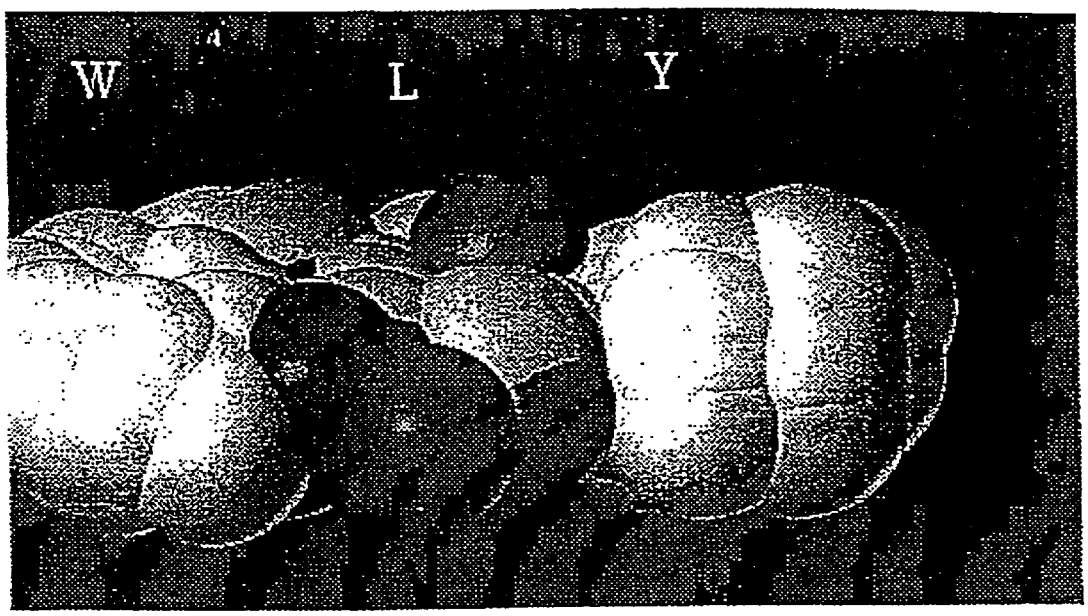
FIG. 3. A side view of a space filling model of one embodiment of a compound of the formula II.

The spatial definition of some embodiments of the compound of the formula II can be further understood by FIGS. 2 and 3 which are representations of a space filling model of the core rings in W and Y and the L group of the compound of the formula II. Note the positioning and space filled by each of W, L and Y as represented by the white regions. The shaded regions indicate hydrogen bond accepting regions found within or in close proximity to L. For the purpose of simplification, the substituents which may append from the core rings in W and Y are not shown. The 3-dimensional structure shown is required of a compound possessing the pharmacological activities recited herein. It should be understood that the compounds contemplated and encompassed by the scope herein can adapt other conformations which may yield pharmacological activity. Such other conformations may involve bond distortions, bond angle distortions, spatial size variations, group spatial orientation variations and the like and are all within the scope of the present invention.

In one embodiment, the selected compound will possess osteoblast proliferation stimulating activity and/or be capable of maintaining or enhancing osteoblast growth in vitro. Such activity may be determined using any one of a number of methods known to the skilled artisan, such as by using the luciferase promoter assay described in Example 1. In that assay, a compound possessing the ability to stimulate osteoblast proliferation or growth will stimulate luciferase activity. Since BMP-2 luciferase promoter constructs were transfected into immortalized murine osteoblasts (2T3 cells), the stimulation of luciferase activity is reasonably correlated to a osteoblast proliferation stimulation activity as recognized by those of ordinary skill in the art.

This method contemplates compounds having a osteoblast proliferation stimulation activity at least about that of the reference compound 2-(4-methoxybenzoyamino)-1,3-benzthiazole. By the phrase "at least about" is meant an activity no less than about 100× less than that activity for the reference compound and preferably an activity at least equal to or greater than the reference compound as determined by the $ED_{50}$ in the promoter assay. Under the assay conditions of Example 1, the reference compound has an $ED_{50}$ of about 0.1 micromolar; therefore, compounds selected by this method should have an $ED_{50}$ no greater than 10 micromolar.

Method for Stimulating Bone Growth

The present invention in one aspect provides a method directed to the use of compounds of the formulae II and III for the stimulation of osteoblast proliferation. It is intended that these compounds will possess the ability to stimulate osteoblast proliferation and thereby bone growth.

This method may be practiced either in vivo or in vitro. When in vivo, it is contemplated that all vertebrate animals, particularly those suffering from osteoporosis, will exhibit at least some stimulation of osteoblast proliferation when treated with compounds of the formula II or III.

When practiced in vitro, it is contemplated that compounds of the formula II or III may be assayed by any number of techniques known to the skilled artisan for determining osteoblast proliferation stimulating activity. One such technique is described as the osteoblast proliferation assay of Example 1.

Without being held bound by the mechanism, it is believed the compounds of the formula II and III exert their bone growth stimulation activity by stimulating osteoblast proliferation which is a result of the compounds' ability to modulate cellular transcription by binding to one or more different types of NHRs.

A Evidence that compounds of the formulae II and III possess the ability to bind to NHRs may be obtained using the assay described in Example 6. In that assay, a compound is tested for its ability to displace tritiated cis-retinoic acid (RA) from a retinoid receptor. Displaced RA is quantitated by scintillation. FIG. 1 shows the results obtained when a compound displaces RA. Compounds possessing the ability to displace RA from retinoic acid receptors can be used to treat or prevent disorders or diseases associated with those receptors. Such diseases and disorders include, by way or example, osteoporosis, arthritis, acne, cancer, diabetes, leukemia, cardiac hypertrophy, inflammation, lymphomas, carcinomas, other oncologic diseases, cervical dysplasia, melanoma, psoriasis, pityriasis rubra pilaris, pustulosis palmoplantaris, nongenital warts, cirrhosis, oral lichen planus, xeroderma pigmentosa, immunosupression and lupus erythematosus.

Preparation of a Composition Possessing Pharmacological Activity—Oxidation Product In some embodiments, the present invention relates to a method for the preparation of a pharmacologically active composition from 4-isopropoxybenzoic acid, or any intermediate compound that provides isopropoxyanthrone possessing activity such as might be found in compositions useful for the inhibition of bone loss or stimulation of bone growth.

Shown in Scheme 1 and described in Example 4 is a multistep synthesis for the conversion of 4-isopropoxybenzoic acid to a pharmacologically active composition possessing the desired osteoblast stimulatory activity. However, one could begin with any of the intermediates in Scheme 1 and still prepare the desired composition by following the appropriate synthetic step(s) disclosed herein. Thus it is contemplated that this pharmacologically active composition is a product of a single to multi-step synthesis where the key step is the oxidative conversion of an oxyanthrone to the desired composition by either heat or $CrO_3/H_2O/AcOH$ treatment. It should be understood that other similar or equivalent reaction conditions and/or ells reagents not recited herein may be used for carry out the oxidative conversion to arrive at the composition possessing antiproliferative activity. Thus, such other reaction conditions and/or agents are considered within the scope and spirit of the present invention.

Scheme 1.

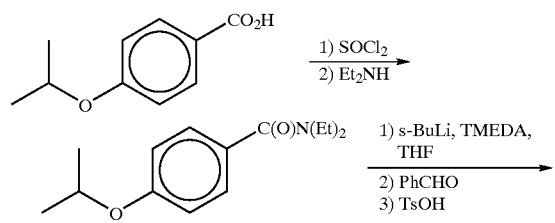

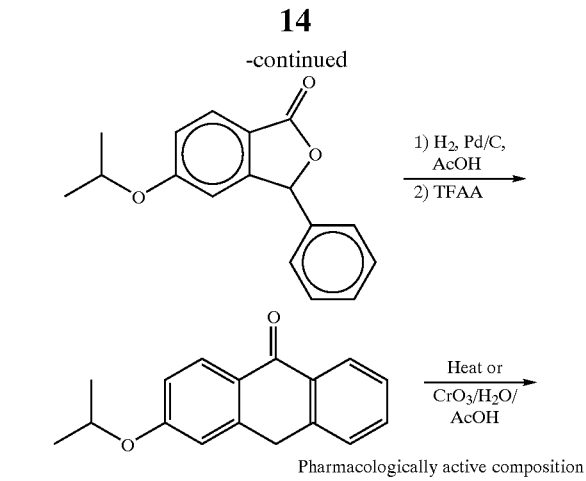

Pharmacologically active composition

Activity of fractionated material that has been through the oxidative step possesses osteoblast proliferation stimulation activity as described in the assay disclosed in Example 1. In that assay, an increase in the production of luciferase action as compared to control was observed, indicating the promotion of gene expression by the candidate composition. In that assay, the present composition, pharmacologically active composition provided by the above-defined process exhibited an $ED_{50}$ of about 10 μg/ml. Preparations that demonstrate an $ED_{50}$ of from about 1 to about 50 μg/ml, or within the range of about 5 to about 40 μg/ml, or even more particularly from about 10 to about 40 μg/ml constitute those preparations contemplated by the present invention.

Method for Preventing and/or Treating Malignant Cell Disorders

This method is for the treatment and/or prophylaxis of malignant cell associated disorders and diseases comprising administering a malignant cell growth inhibiting amount of any one or more of the pharmacologically active compounds of the formulae I, II, III and VI as defined above.

It is believed these compounds are capable of binding to NHRs and would therefore be useful for inhibiting or preventing malignant cell proliferation. Pharmacologically active compounds for malignant cell disorders will be selected as described in Example 3, wherein spatially defined molecules that inhibit or prevent malignant cell proliferation are discernible. Compounds active in that assay would be capable of inhibiting or preventing melanoma cell growth or proliferation. A malignant cell inhibiting amount is defined as an amount capable of inhibiting tumor cell growth by 50% of control cells.

General

The pharmacological activities associated with the compounds provided in the present disclosure may be described as providing for the enhancement or stimulation of osteoblast proliferation, as providing for the retardation or inhibition of tumor or malignant cell proliferation, or as providing for the amelioration of skin conditions, such as acne. The pharmacological activity of these compounds may be described in other aspects of the invention as having a anti-arthritic, anti-aging and/or anti-skin wrinkle activity.

As used herein, "nuclear hormone receptor" (NHR) is intended to mean cellular receptors located in the cell nucleus that are involved in modulating hormone mediated physiological responses. Examples of such receptors include, by way of example and without limitation: steroid hormone receptors such as estrogen, androgen, progesterone, glucocorticoid and mineralocorticoid receptors; retinoic acid receptors such as such retinoid A and retinoid X receptor families and subtypes; thyroid hormone receptors such as vitamin D receptor; and orphan receptors such as ROR and RZR.

As used herein, "alkyl" is intended to include branched, cyclic and straight-chain saturated aliphatic hydrocarbon groups having the specified number of carbon atoms; "haloalkyl" is intended to include branched, cyclic and straight-chain saturated aliphatic hydrocarbon groups having the specified number of carbon atoms, substituted with 1 or more halogen (for example $-C_vF_w$ where v=1 to 3 and w=1 to (2v+1)); "alkoxy" represents an alkyl group of indicated number of carbon atoms attached through an oxygen bridge; "alkylthio" represents an alkyl group of indicated number of carbon atoms attached through a sulfur bridge; and "cycloalkyl" is intended to include saturated ring groups, including mono-, bi- or poly-cyclic ring systems, such as cyclopropyl, cyclobutyl, cyclopentyl, cyclohexyl, cycloheptyl, adamantyl and cyclooctyl. "Alkenyl" is intended to include hydrocarbon chains of either a straight, cyclic or branched configuration and one or more unsaturated carbon-carbon bonds which may occur in any stable point along the chain, such as ethenyl, propenyl, and the like; "cycloalkenyl" is intended to include partially unsaturated cyclic ring groups; and "alkynyl" is intended to include hydrocarbon chains of either a straight, cyclic or branched configuration and one or more triple carbon-carbon bonds which may occur in any stable point along the chain, such as ethynyl, propynyl and the like.

"Alkylcarbonyl" is intended to include an alkyl group of an indicated number of carbon atoms attached through a carbonyl group to the residue of the compound at the designated location; "alkoxyCarbonyl" is intended to include an alkoxy group of an indicated number of carbon atoms attached through a carbonyl group to the residue of the compound at the designated location; "alkylcarbonylamino" is intended to include an alkyl group of an indicated number of carbon atoms attached through a carbonyl group to an amino bridge, where the bridge is attached to the residue of the compound at the designated location; "alkylcarbonyloxy" is intended to include an alkyl group of an indicated number of carbon atoms attached to a carbonyl group, where the carbonyl group & attached through an oxygen atom to the residue of the compound at the designated location; "alkoxycarbonylamino is intended to mean an alkoxy group having the indicated number of carbons and being attached to a carbonyl groud which is then attached through an amino group to the residue of the compound at the designated location; an "alkylamino" is intended to mean an alkyl group having the indicated number of carbon atoms attached to an amino group which is then attached to the residue of the compound at the designated location.

"Halo" or "halogen" as used herein refers to fluoro, chloro, bromo, and iodo; and "counterion" is used to represent a small, negatively charged species such as chloride, bromide, hydroxide, acetate, sulfate, and the like.

As used herein, "aromatic group" is intended to mean aryl or heteroaryl; "aryl" is intended to mean phenyl or phenyl with substituted phenyl rings: "arylalkyl" represents an aryl group attached through an alkyl bridge. By way of example, the term "$C_7$–$C_{10}$ arylalkyl" is intended to refer to an aryl group attached through a $C_1$–$C_4$ alkyl bridge to the residue of the indicated compound; the term "($C_1$–$C_3$ alkyl)aryl" is intended to refer to a $C_1$–$C_3$ alkyl group which is attached through an aryl ring to the residue of the indicated compound: the term "aryl($C_1$–$C_3$ alkyl)" is intended to refer to an aryl group attached through a $C_1$–$C_3$ alkyl group to the residue of the indicated compound.

As used herein, "carbocycle" or "carbocyclic" is intended to mean any stable 3- to 7-membered monocyclic or bicyclic or 7- to 14-membered bicyclic or tricyclic or an up to 26-membered polycyclic carbon ring, any of which may be saturated (cycloalkyl), partially unsaturated (cycloalkenyl), or aromatic. Examples of such carbocyles include, but are not limited to, cyclopropyl, cyclopentyl, cyclohexyl, phenyl, biphenyl, naphthyl, indanyl, adamantyl, or tetrahydronaphthyl (tetralin).

As used herein, "azacycloalkyl" is intended to mean a cycloalkyl group having at least one ring embedded carbon replaced by a nitrogen; "oxacycloalkyl" is intended to mean a cycloalkyl group having at least one ring embedded carbon replaced by an oxygen; "azacycloalkenyl" is intended to mean a cycloalkenyl group having at least one ring embedded carbon replaced by a nitrogen; and "oxacycloalkenyl" is intended to mean a cycloalkenyl group having at least one ring embedded carbon replaced by an oxygen.

The compounds herein described may have asymmetric centers. All chiral, diastereomeric, and racemic forms are included in the present invention. Many geometric isomers of olefins, C=N double bonds, and the like can also be present in the compounds described herein, and all such stable isomers are contemplated in the present invention unless the specific stereochemistry or isomer form is specifically indicated. It will be appreciated that certain compounds of the present invention contain an asymmetrically substituted carbon atom, and may be isolated in optically active or racemic forms. It is well known in the art how to prepare optically active forms, such as by resolution of racemic forms or by synthesis, from optically active starting materials. Also, it is realized that cis and trans geometric isomers of the compounds of the present invention are described and may be isolated as a mixture of isomers or as separated isomeric forms.

Combinations of substituents and/or variables are permissible only if such combinations result in stable compounds. By "stable compound" or "stable structure" it is meant a compound that is sufficiently robust to survive isolation to a useful degree of purity from a reaction mixture, and formulation into an efficacious therapeutic agent.

The term "substituted", as used herein, means that any one or more hydrogens on the designated atom or group is replaced with a selection from an indicated group, provided that the designated atom's normal valency is not exceeded, and that the substitution results in a stable compound.

As used herein, the term "heteroaryl" is intended to mean a completely unsaturated heterocycle; "heterocycle" is intended to mean a stable 5- to 7-membered monocyclic or bicyclic or 7- to 10-membered bicyclic heterocyclic ring which is either saturated or unsaturated, and which consists of carbon atoms and from 1 to 4 heteroatoms independently selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzofuranyl, benzothiophenyl, carbazole, chromanyl, chromenyl, cinnolinyl, decahydroquinolinyl, furanyl, furazanyl, imidazolidinyl, imidazolinyl, imidazolyl, indolinyl, indolizinyl, indolyl, isobenzofuranyl, isochromanyl, isoindolinyl, isoindolyl, isoquinolinyl (benzimidazolyl), isothiazolyl, isoxazolyl, morpholinyl, naphthyridinyl, octahydroisoquinolinyl, oxazolidinyl., oxazolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridinyl, pyridyl, pyrimidinyl, pyrrolidinyl, pyrrolinyl, pyrrolyl, quinazolinyl, quinolinyl, quinoxalinyl, quinuclidinyl, carbolinyl, tetrahydrofuranyl, tetrahydroisoquinolinyl, tetrahydroquinolinyl, tetrazolyl, thianthrenyl, thiazolyl, thienyl, thiophenyl, triazinyl, xanthenyl. Also included are fused ring and spiro compounds containing, for example, the above heterocycles.

The following abbreviations are used herein and are defined as follows:

| RXR | retinoid x receptor |
|-----|---------------------|
| RAR | retinoid A receptor |
| NHR | nuclear hormone receptor |
| BMP | bone morphogenic protein |
| ROR | retinoid related orphan receptor |
| RZR | retinoid Z-related receptors |
| PR | progesterone receptor |
| ER | estrogen receptor |
| AR | androgen receptor |
| GR | glucocorticoid receptor |
| MR | mineralocorticoid receptor |
| TR | thyroid receptor |
| VDR | vitamin D receptor |
| | 1,25(OH)$_2$D 1,25-dihydroxy vitamin D |
| IL-2 | interleukin 2 |
| TNF | tumor necrosis factor |

Pharmaceutical Formulation

As used herein, the term "pharmacologically active compounds" is taken to mean any compound of the formulae I, II, III, IV, V or VI having the desired beneficial pharmacologic or therapeutic activity such as a pharmacological activity to stimulate or maintain osteoblast proliferation.

The pharmacologically active compounds contemplated within the scope of the invention may be in their free acid, free base, or pharmaceutically acceptable salt forms. They may be derivatives or prodrugs of any of the given compounds.

Loading of the pharmacologically active compounds into a pharmaceutical formulation may be accomplished following well known techniques such as those described Remington's Pharmaceutical Sciences, 17th ed., Mack Publishing Company, Easton, Pa., 1985, the disclosure of which is hereby incorporated by reference.

Pharmacologically active compound loading into the formulation may need to be varied according to the pharmacological activity of the compound, the indication being treated, the targeted dosing regimen, the projected method of administration, the integrity or stability of the final formulation or other such reasons.

The pharmaceutical formulation of the present invention may be administered by a variety of methods. Such methods include, by way of example and without limitation: intraperitoneal, intra-articular, intra-arterial, intracardiac, intracavity, intracartilaginous, intradermal, intrathecal, intraocular, intraspinal, intrasynovial, intrathoracic, intratracheal, intrauterine, epidural, percutaneous, intravascular, intravenous, intracoronary, intramuscular or subcutaneous injection; inhalation; or oral, nasal, buccal, rectal, ophthalmic, otic, urethral, vaginal, or sublingual dosage administration. Such methods of administration and others contemplated within the scope of the present invention are known to the skilled artisan.

The pharmaceutical formulation of the present invention may be provided in a variety of ways. Any ingredients used in the present formulation should not degrade or decompose a significant portion of the pharmacologically active compound used prior to administration.

For injection, the pharmaceutical formulation may be a powder suitable for reconstitution with an appropriate solution, as, for example and without limitation: freeze dried, rotary dried or spray dried powders; amorphous powders; or granules, precipitates or particulates. For injection, the pharmaceutical formulation may also be a suspension in the appropriate solutions, such as, by way of example and without limitation, water, aqueous solvents, nonprotic solvents, protic solvents, hydrophilic solvents, hydrophobic solvents, polar solvents, nonpolar solvent and/or combinations thereof, optionally containing stabilizers, pH modifiers, surfactants, bioavailability modifiers and/or combinations thereof.

The pharmaceutical formulation may be administered in the form of a depot injection or implant preparation which may be formulated in such a manner as to permit a sustained release of the pharmacologically active compound. The formulation can be compressed into pellets or small cylinders and implanted subcutaneously or intramuscularly as depot injections or implants. Implants may employ inert materials such as biodegradable polymers or synthetic silicones, for examples, Silastic, silicone rubber-manufactured by the Dow-Corning Corporation.

For nasal administration, the pharmaceutical formulation may be a spray or aerosol containing the appropriate solvents is (such as water, aqueous, nonaqueous, polar, nonpolar, hydropic, hydrophilic and/or combinations thereof) and optionally other compounds (stabilizers, antimicrobial agents, antioxdants, pH modifiers, surfactants and/or bioavailability modifiers). A propellant such as compressed air, nitrogen, carbon dioxide or hydrocarbon based low boiling solvents (such as butane, propane or others) would be used in an aerosol formulation. In addition, pastes, ointments or creams containing the micelles of the invention may also be used. It is contemplated that bioavailability enhancers such as alcohols or other compounds that enhance the penetration of the pharmacologically active compound from the pharmaceutical formulation into the nasal mucosa may be needed to prepare suitable formulations for nasal administration.

For oral, buccal, and sublingual administration, the pharmaceutical formulation may be in the form of a gelcap, caplet, tablet, capsule, suspension or powder. For rectal administration, the pharmaceutical formulation may be in the form of a suppository, ointment, enema, tablet and cream for release of compound in the intestines, sigmoid flexure and/or rectum.

In solid unit dosage forms the compounds can be combined with conventional carriers, for example, binders, such as acacia, corn starch or gelatin; disintegrating agents, such as, corn starch, guar gum, potato starch or alginic acid; lubricants, such as, stearic acid or magnesium stearate; and inert fillers, such as lactose, sucrose or corn starch.

The term "unit dosage form" is used herein to mean a single or multiple dose form containing a quantity of the pharmacologically active compound containing formulation, said quantity being such that one or more predetermined units are normally required for a single therapeutic administration. In the case of multiple dose forms, such as suspensions or scored tablets, said predetermined unit will be one fraction such as 5 ml (teaspoon) quantity of a suspension or a half or quarter of a scored tablet, of the multiple dose form.

The pharmaceutical formulations may also be administered as liquid suspensions or solutions using a sterile liquid, such as an oil, water, an alcohol, or mixtures thereof, with or without the addition of a pharmaceutically suitable surfactants, suspending agent, or emulsifying agent for oral or parenteral administration.

For suspension preparations, the pharmaceutical formulation may include oils, for example, fixed oils, such as peanut oil, sesame oil, cottonseed oil, corn oil and olive oil; fatty acids, such as oleic acid, stearic acid and isotearic acid; and fatty acid esters, such as ethyl oleate, isopropyl myristate, fatty acid glycerides and acetylated fatty acid glycerides; with alcohols, such as ethanol, isopropanol, hexadecyl alcohol, glycerol and propylene glycol; with glycerol ketals, such as 2,2-dimethyl-1,3-dioxolane-4-methanol; with ethers, such as poly(ethyleneglycol) 450, with petroleum hydrocarbons, such as mineral oil and petrolatum; with water, or with mixtures thereof; with or without the addition of a pharmaceutically suitable surfactant, suspending agent or emulsifying agent.

Oils can also be employed in the preparation of formulations of the soft gelatin type and suppositories. Water, saline, aqueous dextrose and related sugar solutions, and glycerols may be employed in the preparation of suspension formulations which may suitably contain suspending agents, such as pectin, carbomers, methyl cellulose, hydroxypropyl cellulose or carboxymethyl cellulose, as well as buffers and preservatives. Soaps and synthetic detergents may be employed as surfactants and as vehicles for detergent compositions. Suitable soaps include fatty acid alkali metal, ammonium, and triethanolamine salts. Suitable detergents include cationic detergents, for example, dimethyl dialkyl ammonium halides, alkyl pyridinium halides, and alkylamine acetates; anionic detergents, for example, alkyl, aryl and olefin sulfonates, alkyl, olefin, ether and monoglyceride sulfates, and sulfosuccinates; nonionic detergents, for example, fatty amine oxides, fatty acid alkanolamides, and poly(oxyethylene)-block-poly(oxypropylene) copolymers; and amphoteric detergents, for example, alkyl β-aminopropionates and 2-alkylimidazoline quaternary ammonium salts; and mixtures thereof.

It is contemplated that either one or a combination of rapid or short-acting, fast-releasing, long-acting, sustained release, controlled release or slow release dosage forms may be used in the present invention. The course and duration of administration of and the dosage requirements for the formulation of the present invention will vary according to the subject being treated, the compound being administered, the formulation used, the method of administration used, the severity and type of indication being treated, the coadministration of other drugs and other factors.

The pharmacologically active compounds contained within the formulation may be formulated as their pharmaceutically acceptable salts. As used herein, "pharmaceutically acceptable salts" refer to derivatives of the disclosed compounds wherein the parent pharmacologically active compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfonic, sulfamic, phosphoric, nitric and the like; and the salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent pharmacologically active compound which contains a basic or acidic moiety by conventional chemical methods. Generally, such salts can be prepared by reacting the free acid or base forms of these compounds with a predetermined amount of the appropriate base or acid in water or in an organic solvent, or in a mixture of the two. Generally, nonaqueous media are preferred. Lists of suitable salts are found in Remington's Pharmaceutical Sciences, 17th ed., Mack Publishing Company, Easton, Pa., 1985, p. 1418, the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

PREFERRED EMBODIMENTS

Following long-standing patent law convention, the terms "a" and "an" mean "one or more" when used in this specification.

Methods for Stimulating BMP-2 Activity; Osteoblast Proliferation

The present invention provides a method of stimulating BMP-2 promoter activity and thereby osteoblast proliferation. In some embodiments, the method comprises exposing cells comprising osteoblasts or osteoblast precursor cells to a pharmacologically active compound of the formula I $$X-L-Z \qquad \text{Formula I}$$

wherein:

X is selected from the group consisting of:

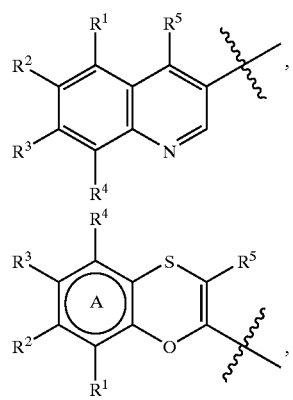

-continued

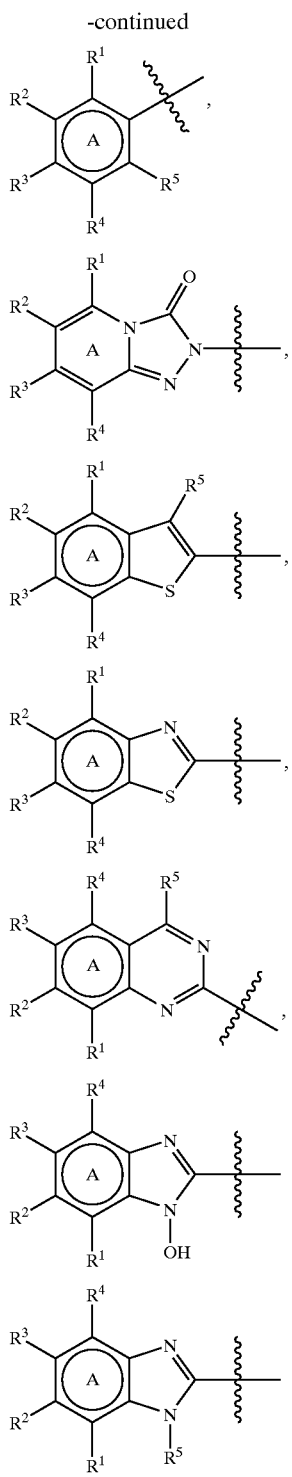

L is selected from the group consisting of:

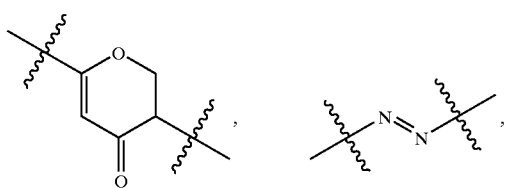

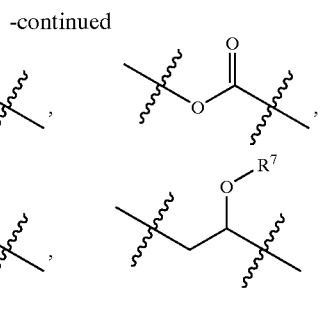

and a single bond

Z is selected from the group consisting of:

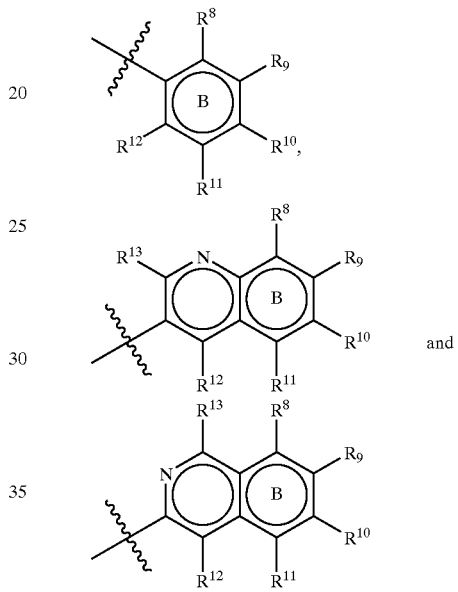

$R^1$ is selected from the group consisting of:
  H, OH, C1–C4 alkyl, C1–C4 alkoxy, C1–C4 alkylthio, halo and (C1–C12)alkyl-carbonyloxy;
$R^2$ is selected from the group consisting of:
  H, OH, halo, C1–C6 alkyl, C1–C6 alkenyl, C1–C6 alkoxy and (C1–C12)alkyl-carbonyloxy;
$R^3$ is selected from the group consisting of:
  H, OH, halo, C1–C6 alkyl, C1–C6 alkoxy, C1–C6 alkenyl and (C1–C12)alkyl-carbonyloxy;
$R^4$ is H;
$R^5$ is selected from the group consisting of:
  H, halo, C1–C6 alkyl, C1–C6 alkoxy, —OC(=O)Me, phthalimide and (C1–C12)alkyl-carbonyloxy;
$R^6$ is selected from the group consisting of:
  H, OH, —NH$_2$, C1–C4 alkyl and C1–C4 alkoxy;
$R^7$ is selected from the group consisting of:
  H, C1–C4 alkyl, (C1–C4)alkyl-carbonyl and (C7–C10) arylalkyl;
$R^8$ is selected from the group consisting of:
  H, OH, halo, —CF$_3$, C1–C4 alkyl, C1–C4 alkoxy, —NHC(=O)Me and —N(C1–C4 alkyl)$_2$;
$R^9$ is selected from the group consisting of:
  H, OH, halo, —CN, —NO$_2$, C1–C8 alkyl, C1–C8 alkoxy, —NHC(=O)Me and —OC(=O)Me;
$R^{10}$ is selected from the group consisting of:
  H, OH, halo, —CN, —NO$_2$, C1–C4 haloalkyl, —CO$_2$H, C1–C12 alkyl, C1–C12 alkoxy, phenyl, C1–C12 alkenyl, (C1–C4)alkoxycarbonyl, —NHC(=O)Me, (C1–C4)alkylcarbonyl, (C1–C12)alkylcarbonyloxy and heteroaryl;

$R^{11}$ is selected from the group consisting of:

H, OH, halo, C1–C4 haloalkyl, —CF₃, C1–C4 alkyl, —NH₂, C1–C4 alkoxy, —NHC(=O)Me, C1–C4 alkenyl, (C1–C4)alkoxycarbonyl, (C1–C4) alkylcarbonyl, and (C1–C4)alkylcarbonyloxy;

$R^{12}$ is selected from the group consisting of:

H, OH, —NH₂, C1–C4 alkyl, C1–C4 alkoxy, (C1–C4) alkylcarbonyl; and $R^{13}$ is selected from the group consisting of:

H, OH, halo, —NH₂, C1–C4 alkyl, C1–C4 alkoxy, —N(C1–C4 alkyl)₂.

In some embodiments of the method, the pharmacologically active compound of formula I may be further defined as follows:

$R^{10}$ and $R^{11}$ join together to form a 5–7 membered carbocycle or oxacarbocycle fused to the ring to which they are attached, where the carbocycle and oxacarbocycle are substituted with one or more groups selected from the group consisting of C1–C4 alkyl, C1–C4 alkoxy, OH, halo, carboxyl, H and aryl; provided that:

1) L is

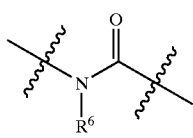

and

Z is

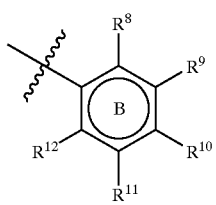

when

X is selected from:

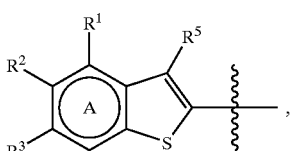

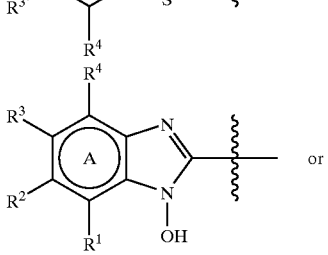

2) when X is

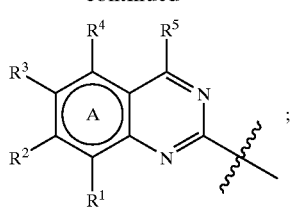

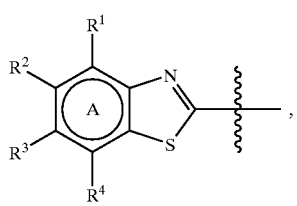

then

L is selected from the group consisting of:

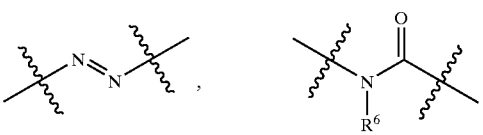

and a single bond 3) when X is:

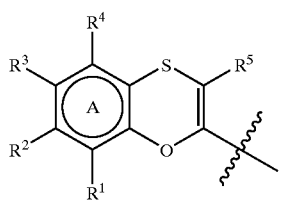

and

Z is:

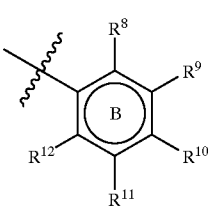

then

L is

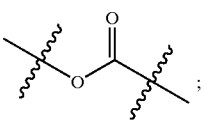

4) when X is:

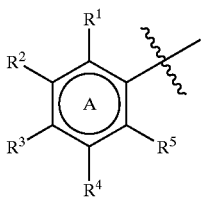

and

Z is:

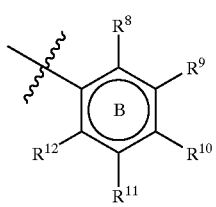

then
L is:

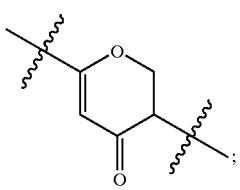

5) when X is:

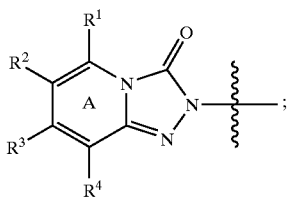

then
Z is:

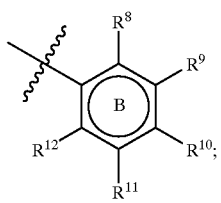

and

L is:

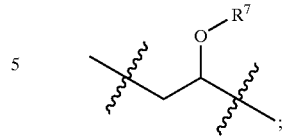

6) when X is:

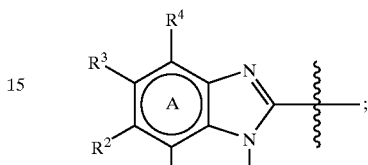

then
Z is:

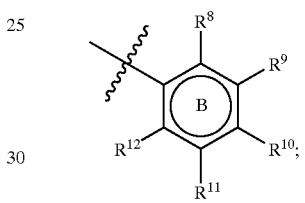

and
L is:

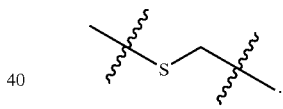

These methods may comprise a second step of stimulating BMP-2 promoter activity to provide for stimulation of osteoblast proliferation and bone growth. It is expected that bone resorption may also be reduced or inhibited.

Pharmacophore Model

Another aspect of the present invention provides a method for selecting a pharmacologically active compound. In some embodiments, the method comprises:

selecting candidate compounds having a spatially defined 3-dimensional structure as defined by formula II $$W-L-Y \qquad \text{Formula II}$$

to provide spatially defined candidate compounds, wherein,
W comprises an aromatic group having a centroid indicated by the letter "A";
Y comprises a carbocyclic group having a centroid indicated by the letter "B";
L comprises a group linking X and Z;
a plane "P" is formed by the aromatic atoms of the aromatic group in W;
the centroid "B" lies within about 0.7 angstroms above or below the plane "P"; and
the centroid "A" and the centroid "B" are by about 6, or about 6.6, to about 8, or about 8.5, angstroms apart; and
selecting spatially defined candidate compounds having pharmacological activity.

In some embodiments, the 3-dimensional structure of the spatially defined candidate compounds is further defined as follows:

L occupies a space which outer limit is less than or equal to about 3, or about 3.1, angstroms, as measured by heavy atom distance, above or below and normal to the plane "P" as measure along a normal to the plane "P".

In other embodiments, L occupies a space which outer limit is about 4, or about 4.7, to about 6.0 angstroms, as measured by heavy atom distance, perpendicular to a line connecting centroid "A" to centroid "B" and within the plane "P".

The compound of formula II in other embodiments of the method is defined as comprising at least two hydrogen bond accepting groups located either within or in close proximity to L, the hydrogen bond accepting groups being defined as follows:

1) the hydrogen bond accepting groups are within about 2, or about 2.3, to about 5, or about 5.4 angstroms apart;
2) one hydrogen bond accepting group is about 4, or about 4.5, to about 7, or about 7.7 angstroms from centroid "A" and about 2, or about 2.7, to about 3, or about 3.8 angstroms from centroid "B"; and
3) one hydrogen bond accepting group is about 2, or about 2.6 to about 3, or about 3.8 angstroms from centroid "A" and about 4, or about 4.6, to about 6, or about 6.9 angstroms from centroid "B".

In some embodiments, the method is further defined in that the compound of formula II is defined as:
1) not a compound of the formula X

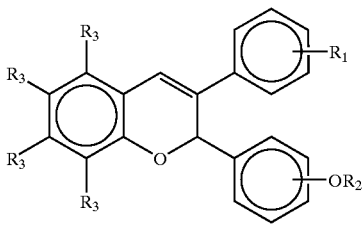

Formula X where $R_1$ is H, OH, C1–C17 alkoxy, (C1–C17)alkylcarbonyloxy, (C1–C17)alkylcarbonylamino or (C1–C17)alkylcarbonyl; $R_2$ is —(CH$_2$)$_{(1-6)}$—CH$_2$-heterocycle; and $R_3$ is H, OH, C1–C17 alkoxy, (C1–C17)alkylcarbonyloxy, (C1–C17)alkylcarbonylamino or (C1–C17)alkylcarbonyl; and
2) not a compound of the formula XI

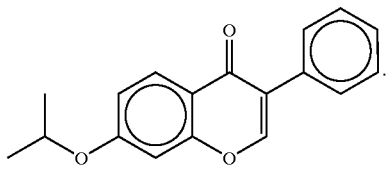

Formula XI

The invention also provides methods of using the spatially defined molecules defined by formula II for stimulating BMP-2 promoter activity, osteoblast proliferation, tumor inhibition, skin conditions or arthritis. Candidate substances that satisfy the spatial characteristics above will be selected on the basis of the specific pharmacological activity desired using the assays described herein.

The aromatic ring having the centroid "A" may be independently substituted with one or more of the group consisting of: H, halo, hydroxy, amino, carboxyl, cyano, C1–C6 alkyl, C1–C2 haloalkyl, C1–C6 alkoxy, C1–C6 alkenyl, —OC(=O)—(C1–C6 alkyl) and —NHC(=O)—(C1–C6 alkyl).

In other, further embodiments of the above preparations having the centroid "A" substitution or substitutions, the carbocyclic group having the centroid "B" is independently substituted with one or more of the group consisting of: H, halo, hydroxy, amino, carboxyl, cyano, nitro, trifluoromethyl, C1–C6 alkyl, C1–C2 haloalkyl, C1–C6 alkoxy, C1–C6 alkenyl, aryl, heteroaryl, —OC(=O)—(C1–C6 alkyl) and —NHC(=O)—(C1–C6 alkyl).

Benzthiazole—Methods in Osteoblast Proliferation

Another aspect of the present invention comprises a method for stimulating osteoblast proliferation or BMP-2 promoter activity employing a pharmacologically active compound of a formula III

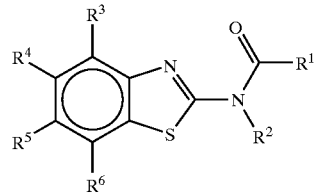

Formula III wherein:
$R^1$ is selected from the group consisting of:
 aryl, naphthyl, heteroaryl and cycloalkyl, wherein each of the $R^1$ substituents is substituted by one or more of the groups consisting of:
  C1–C7 alkyl, C1–C7 alkoxy, —NO$_2$, —CF$_3$, aryl, benzyloxy, hydroxy, C1–C2 haloalkyl, halo, cyano, carboxyl, hydrogen, aryl, (C1–C4)alkylcarbonylamino, (C1–C4)alkylcarbonyl, (C1–C4)alkyl-aryl, and NH$_2$;
$R^2$ is H, C1–C4 alkoxy, amino, or C1–C4 alkyl;
$R^3$ and $R^6$ are independently selected from the group consisting of:
 H, hydroxy, (C1–C5)alkylcarbonyloxy, cyano, C1–C4 alkyl, C1–C4 alkenyl and C1–C4 alkoxy; and
$R^4$ and $R^5$ are independently selected from the group consisting of:
 H, halo, hydroxy, (C1–C4)alkyl-carbonyloxy, cyano, C1–C2 haloalkyl, C1–C4 alkoxy, benzoyl, C1–C4 alkyl, C1–C4 alkenyl, C1–C4 alkynyl, (C1–C4)alkyl-aryl, (C1–C4)alkenyl-aryl, (C1–C4)alkynyl-aryl, (C1–C4)alkyl-(C6–C10)cycloalkyl, (C1–C4)alkenyl-(C6–C10)cycloalkyl, (C1–C4)alkynyl-(C6–C10) cycloalkyl, carboxy and (C1–C4)alkoxycarbonyl.

In some embodiments of the method, the pharmacologically active compound of formula III is further defined as follows:
$R^4$ and $R^5$ join together to form a 5–6 membered carbocycle or oxacarbocycle fused to the ring to which they are attached, where the carbocycle or oxacarbocycle is substituted by one or more substituents selected from the group consisting of:
 C1–C4 alkyl, C1–C4 alkoxy, hydroxy, halo, carboxyl, hydrogen and aryl.

The methods comprise administering an effective amount of the compound of formula III to cells comprising osteoblasts.

In a particular embodiment, the method comprises stimulating BMP-2 promoter activity comprising administering a pharmacologically active preparation of 2(2-methoxybenzamido)-1,3-benzthiazole. A method for stimulating proliferation of osteoblasts using the above-named compound is also specifically envisioned.

Benzthiazole and Related Compounds

Another aspect of the present invention relates to benzthiazole compounds and related compounds of the formula III as pharmacologically active preparations. These pharmacologically active preparations are expected to be useful in stimulating osteoblast proliferation, stimulating BMP-2 promoter activity, inhibiting or reducing bone resorption and for inhibiting tumor cells. The formula III is as follows:

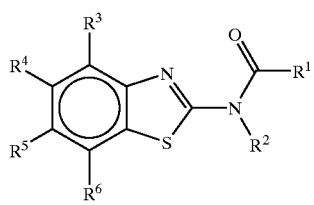

Formula III wherein:
$R^1$ is selected from the group consisting of:
  aryl, naphthyl, heteroaryl and cycloalkyl, where each of the above substituents is substituted by one or more of the groups independently selected from the group consisting of:
    C1–C7 alkyl, C1–C7 alkoxy, —CF$_3$, —NO$_2$, benzyloxy, hydroxy, C1–C2 haloalkyl, halo, cyano, carboxyl, hydrogen, aryl, (C1–C4)alkylcarbonylamino, (C1–C4)alkylcarbonyl, (C1–C4)alkyl-aryl, and —NH$_2$;
$R^2$ is selected from the group consisting of:
  H, C1–C4 alkoxy, amino, and C1–C4 alkyl;
$R^3$ and $R^6$ are independently selected from the group consisting of:
  H, hydroxy, (C1–C2)alkylcarbonyloxy, cyano, C1–C4 alkyl, C1–C4 alkenyl and C1–C4 alkoxy; and
$R^4$ and $R^5$ are independently selected from the group consisting of:
  H, halo, hydroxy, (C1–C4)alkyl-carbonyloxy, cyano, C1–C2 haloalkyl, C1–C4 alkoxy, benzoyl, C1–C4 alkyl, C1–C4 alkenyl, C1–C4 alkynyl, (C1–C4)alkyl-aryl, (C1–C4)alkenyl-aryl, (C1–C4)alkynyl-aryl, (C1–C4)alkyl-(C6–C10)cycloalkyl, (C1–C4)alkenyl-(C6–C10)cycloalkyl, (C1–C4)alkynyl-(C6–C10) cycloalkyl, carboxy and (C1–C4)alkoxycarbonyl.

These compounds are further defined in other embodiments of the invention as follows: $R^4$ and $R^5$ join together to form a 5–6 membered carbocycle or oxacarbocycle fused to the ring to which they are attached, where the carbocycle or oxacarbocycle is substituted by one or more of the groups selected from the group consisting of:
  C1–C4 alkyl, C1–C4 alkoxy, hydroxy, halo, carboxyl, hydrogen and aryl;
provided that:
when $R^2$, $R^3$, $R^4$, $R^5$, $R^6$ are all H, then $R^1$ cannot be:
  phenyl, naphthyl, mono-substituted phenyl in which the substitution pattern is any one of:
    2-azido, 2-nitro, 2-chloro, 2-bromo, 2-fluoro, 2 hydroxy, 2 carboxy, 2-(2-carboxy-5-chlorophenyl), 2-(4'acetylbenzsulfonyloxy), 2-(4'-(cyanoacetyl) benzsulfonyloxy), 2-(4'-ethoxyphenyl)amino, 2-di (4'-hydroxyphenyl)methyl, 2-di (4'-acetoxyphenyl) methyl, 2-(2,3-carboxypropenoyl)amino, 3-bromo, 3-chloro, 3-methoxy, 4-chloro, 4-bromo, 4-fluoro, 4-methyl, 4-nitro,4-methoxy, 4-ethoxy, 4-n-propoxy, 4-i-propoxy, 4-n-butoxy, 4-i-butoxy, 4-n-pentoxy, 4-benzyloxy, 4-allyloxy, 4-acetoxy, 4(2'-diethylamino)ethoxy, 4-amino, 4-dimethylamino, 4-guanidino, 4-thiomethyl, 4-(4'-methylbenzsulfonyl)amino, 4(diethylphosphono) methyl, 4-(di-i-propylphosphonol)methyl,

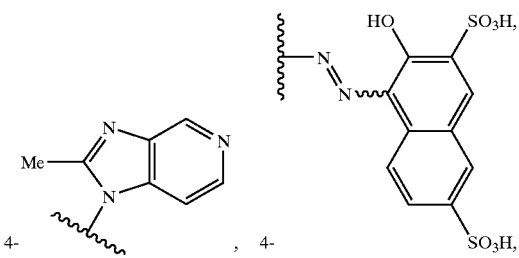

4-                     , 4-

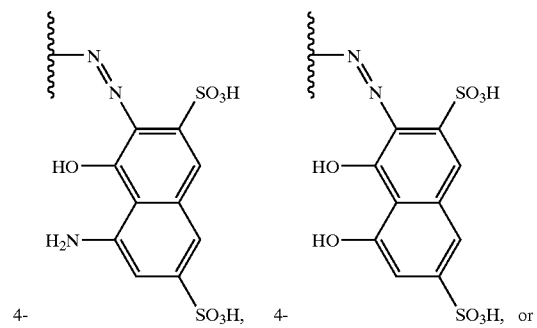

4-            SO$_3$H, 4-            SO$_3$H, or

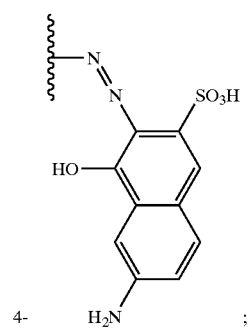

4-            ;

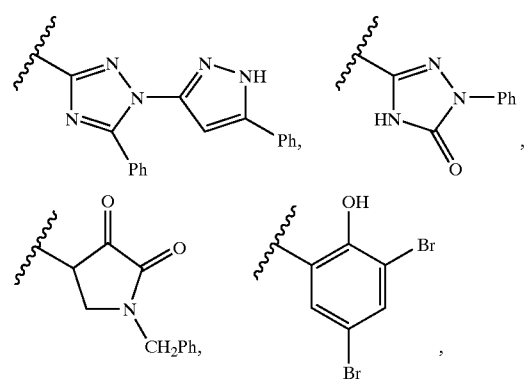

-continued
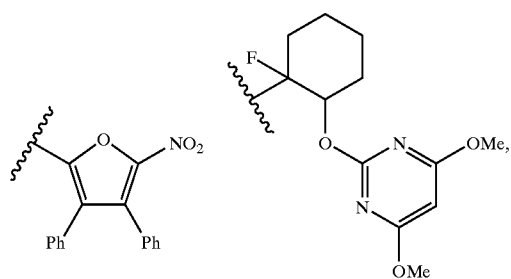
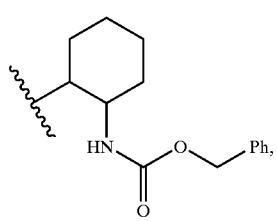
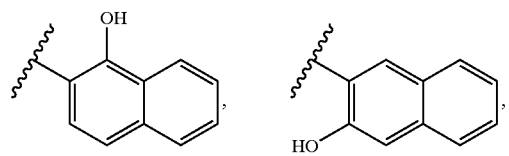
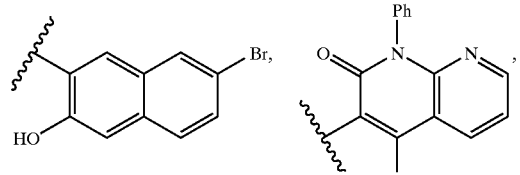
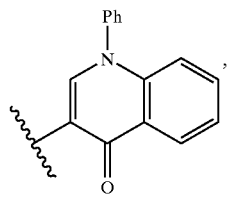
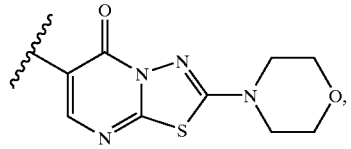
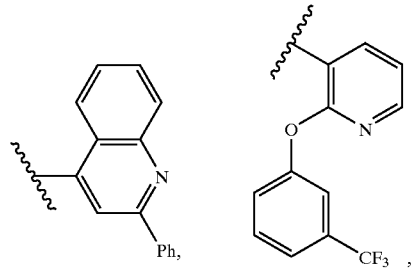
-continued
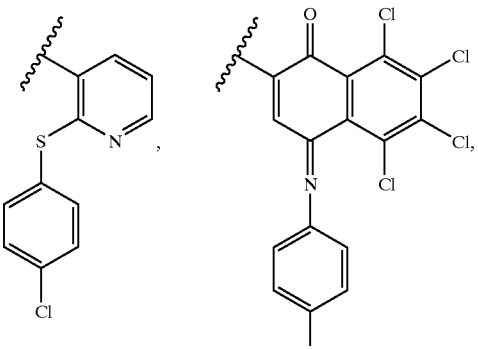
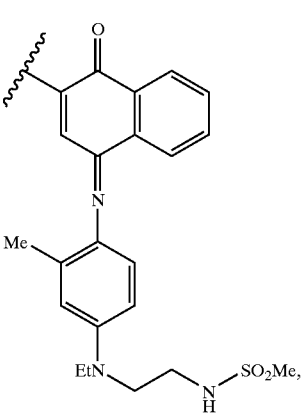
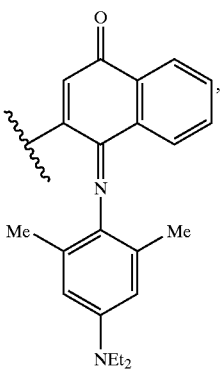
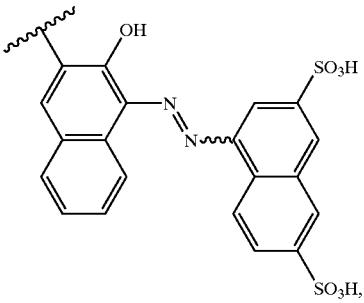

33
-continued
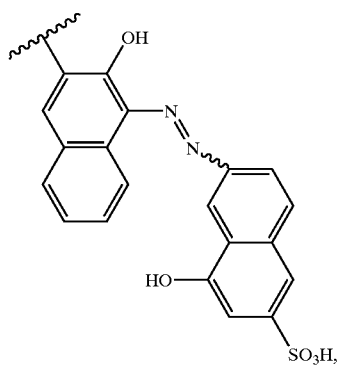
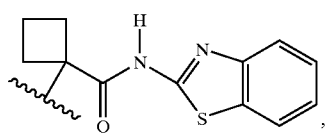
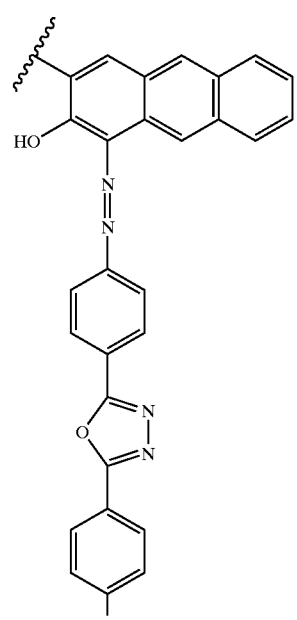
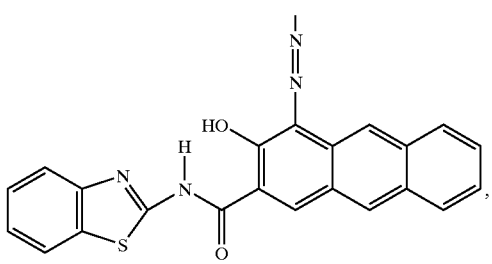
34
-continued
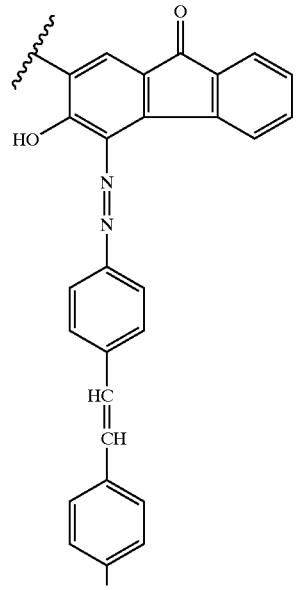
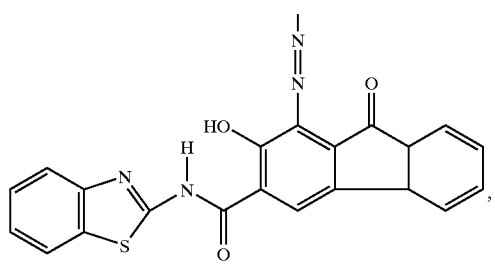
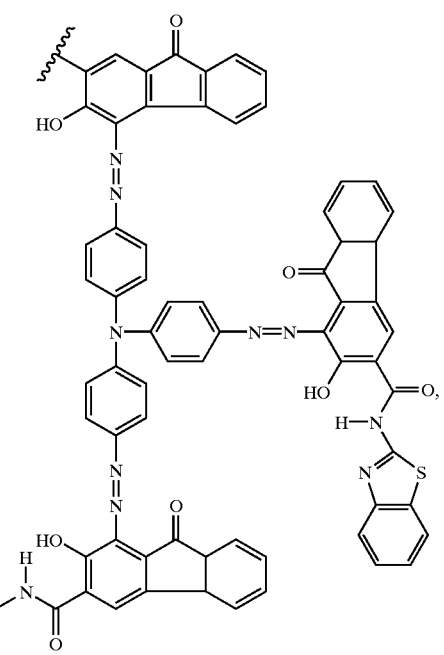

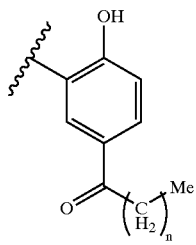

where n=5, 6, 8, 10.14,

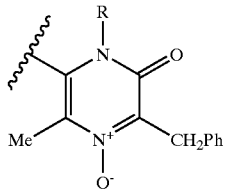

where R is either H or Me,

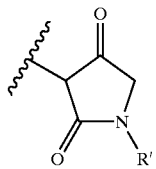

where R' is benzyl, 2-phenylethyl, alpha-naphthylmethyl, 4-methoxybenzyl, 3,4'-dichlorophenyl, or 2-(3',4'-dichlorophenyl)ethyl,

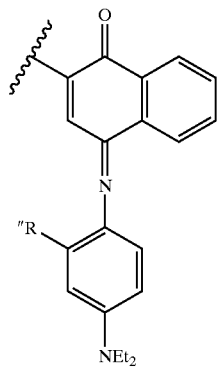

where R" is either H or Me,

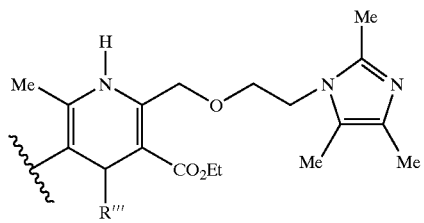

where R'" is 2-chlorophenyl, 2-fluorophenyl, or 3 chlorophenyl,

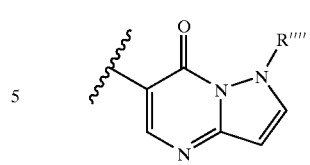

where R"" is either phenyl or 2-pyridyl,

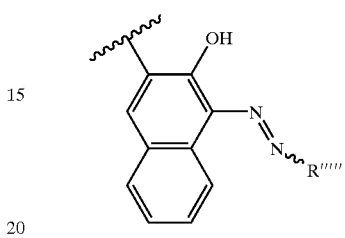

where R""' is taken from the set: 4-sulfophenyl, 3,6-disulfophenyl, 4-methoxy-3-sulfophenyl, 6-chloro-3-sulfophenyl, or 2,5-dichloro-4-sulfophenyl.

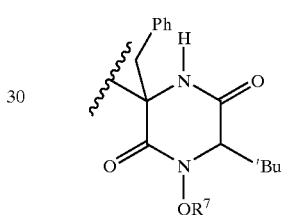

where $R^7$ is benzyl or hydrogen,

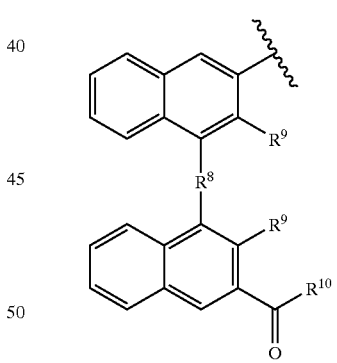

where $R^9$ is hydroxy, $R^{10}$ is

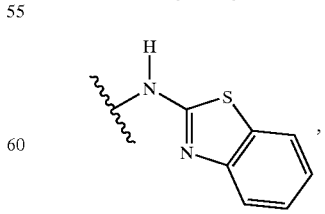

and $R^3$ is taken from the set:

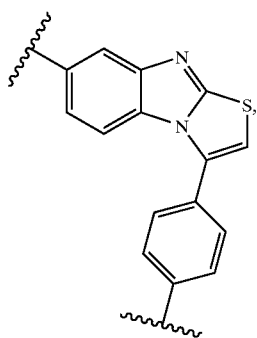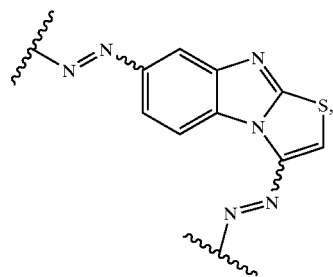
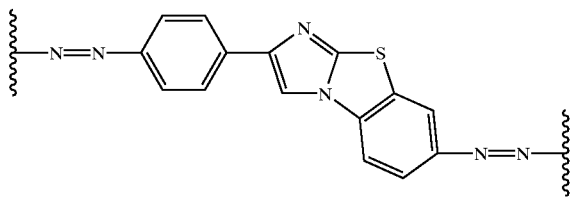
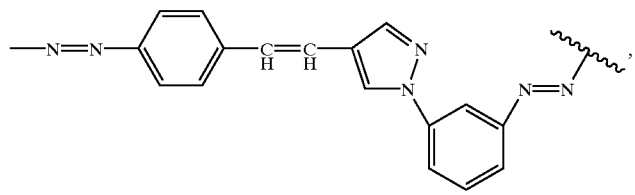
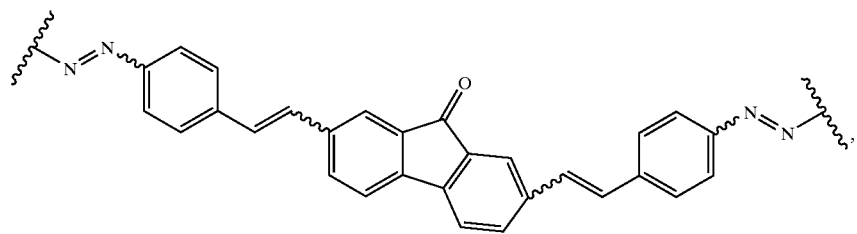
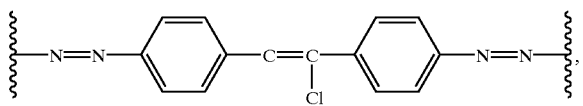
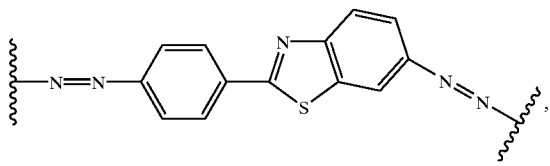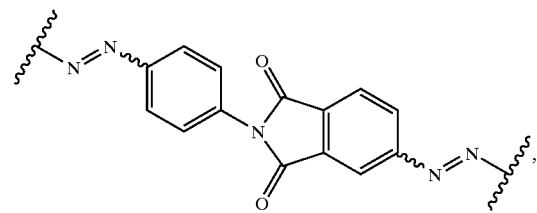

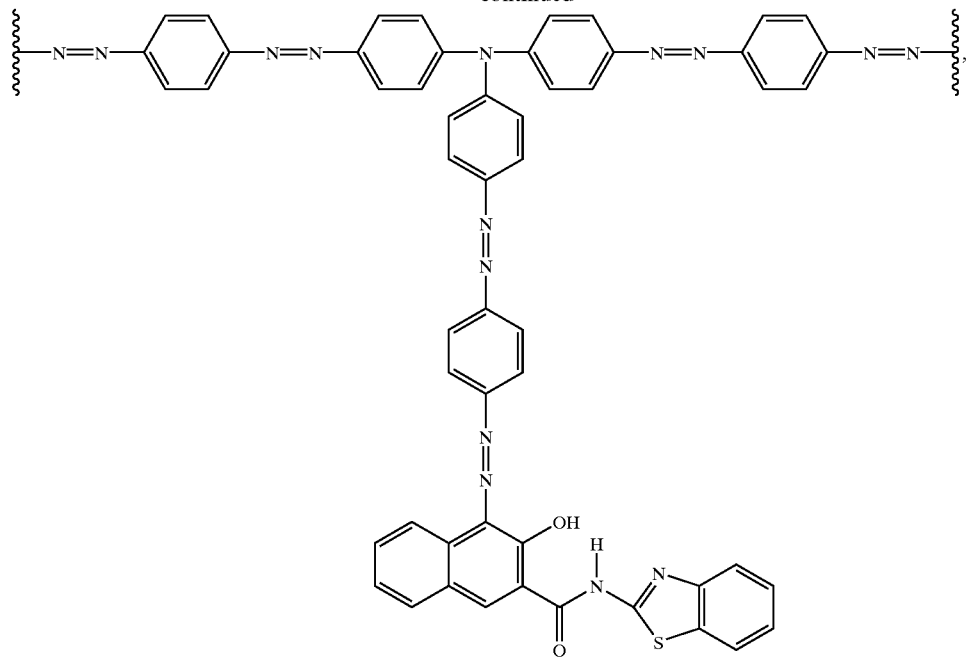
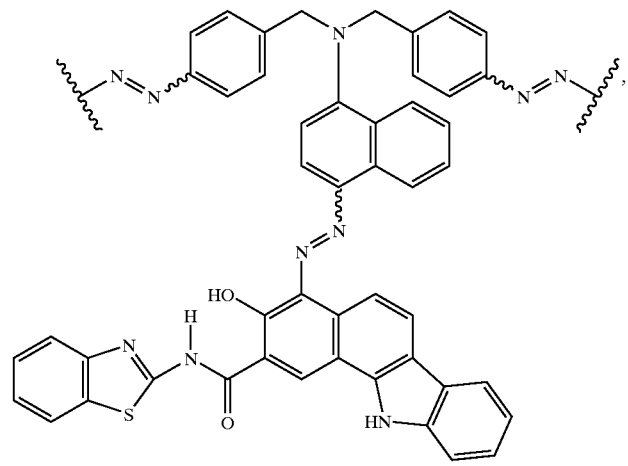
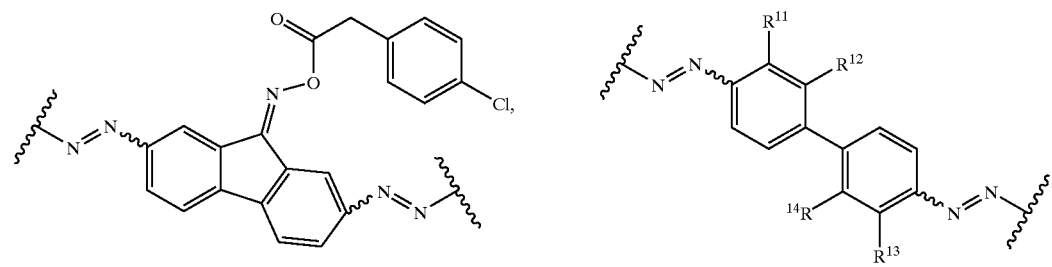
where $R^{11}$, $R^{12}$, $R^{13}$, and $R^{14}$ are all hydrogen, or where $R^{12}$ and $R^{14}$ both equal hydrogen and $R^{11}$ and $R^{13}$ together both equal hydrogen, methyl, methoxy, or chloro, or where $R^{11}$ and $R^{13}$ both equal hydrogen and $R^{12}$ and $R^{14}$ both equal chloro, where afasfasR11 is methal $R^{11}$ is methyl and $R_{12}$, $R^{13}$, and $R^{14}$ are all hydrogen,

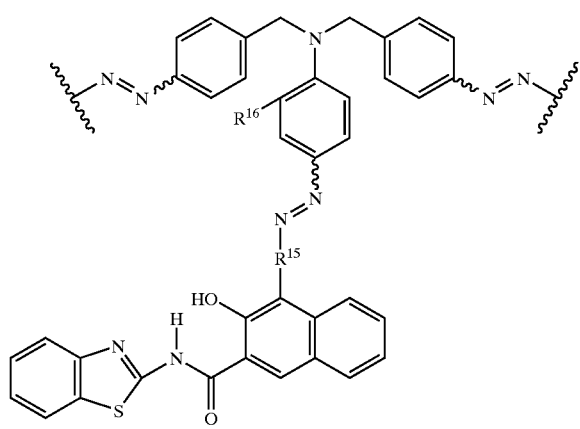

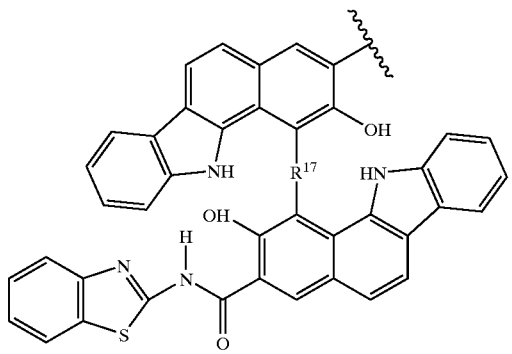

is methyl, or where $R^{11}$, $R^{12}$, $R^{14}$ are all hydrogen and $R^{13}$ is methyl where $R^{15}$ is a bond and $R^{16}$ is hydrogen or chloro, or where $R^{15}$ is 4-azophenyl and $R^{16}$ is chloro;

where $R^9$ is hydrogen, $R^{10}$ is

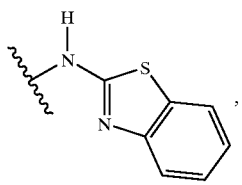

and $R^8$ is

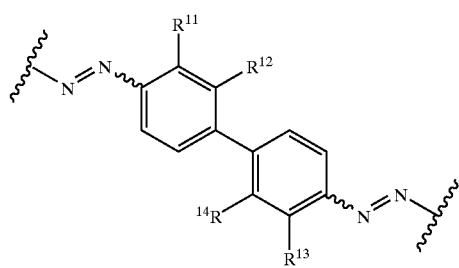

where $R^{11}$ and $R^{13}$ equal chloro and R12 and R14 equal hydrogen; or where $R^9$ is hydroxy, $R^{10}$ is hydroxy, and $R^8$ is

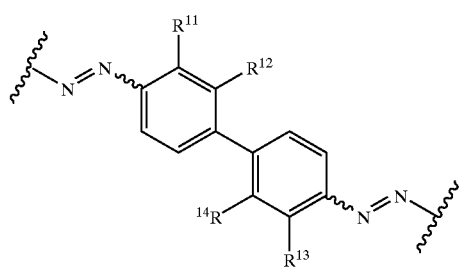

where $R^{12}$ and $R^{14}$ both equal hydroxy and $R^{11}$ and $R^{13}$ together both equal methyl, methoxy, or chloro, or where $R^{11}$ and $R^{13}$ both equal hydrogen and $R^{12}$ and $R^{14}$ both equal chloro, or where $R^{12}$, $R^{13}$, and $R^{14}$ are all hydrogen and $R^{11}$ where $R^{17}$ is taken from the set:

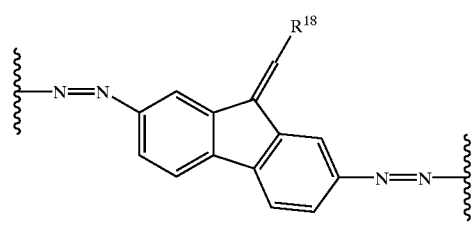

where $R^{18}$ is either phenyl or 3-thienyl,

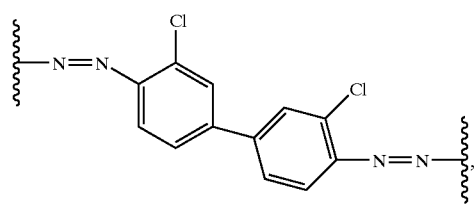

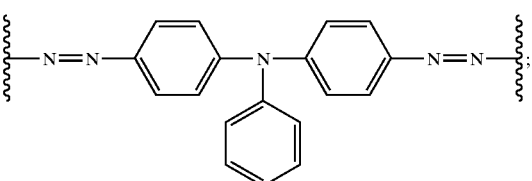

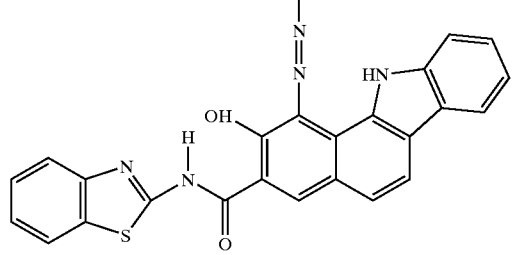

or

-continued

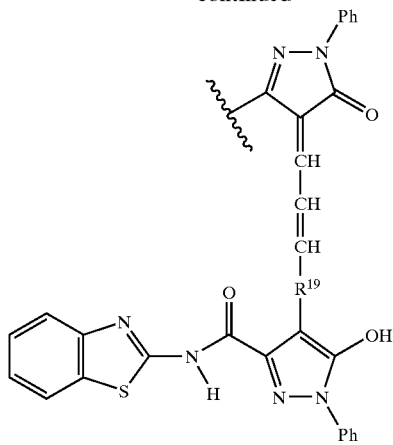

or where R19 is either a bond or —CH=CH—;

when $R^3$, $R^4$, $R^5$ and $R^6$ are all H, and R2 is phenyl, then R1 cannot be phenyl;

when R3, R4, R5, R6 are all H, and R2 is methyl, then R1 cannot be phenyl;

when R3, R4, R5, R6 are all H, and R2 is amino, then R1 cannot be 4-methoxyphenyl;

when R3, R4, R5, R6 are all H, and R2 is

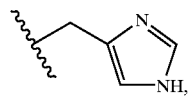

then R1 cannot be 3-chlorophenyl;

when R3, R4, R5, R6 are all H, and R2 is

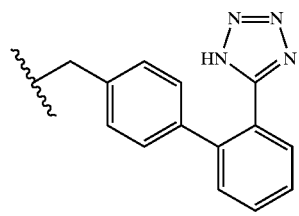

then R1 cannot be cyclopropyl;

when R3, R4, R5, R6 are all H, and R2 is either 2-(dimethylamino)ethyl or 3-(dimethylamino)propyl, then R1 cannot be phenyl;

when R3, R4, R5, R6 are all H, and R2 is N,N'-diphenylamidino, then R1 cannot be phenyl;

when R3, R4, R5, R6 are all H, and R2 is

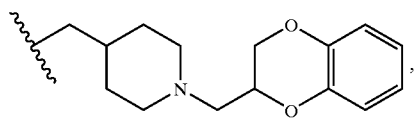

then R1 cannot be 2-furyl, 2-thiazoyl, 4-methoxyphenyl, 4-trifluoromethylphenyl, 3,4-dimethoxyphenyl;

when R3, R4, R5, R6 are all H, and R2 phenyl, then R1 cannot be:

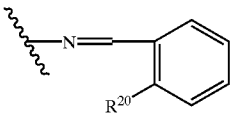

where R20 is any one of H, benzoyl, or nitro,

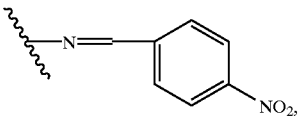

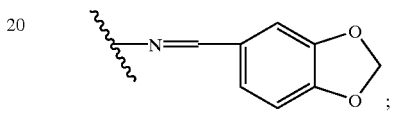

when R3, R4, R5, R6 are all H, and R2 is

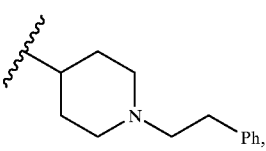

then R1 cannot be either 2-furyl or 3-furyl;

when R2, R4, R5, and R6 are all hydrogen and R3 is methoxy, then R1 cannot be:

phenyl, 2-carboxyphenyl, 4-guanidinophenyl, 4-nitrophenyl, 3,5-dinitrophenyl, 4-(diphenylphosphonomethyl)phenyl, 4-(2'-diethylphosphonoethoxy)phenyl, 4-(3'diethylphosphonopropoxy)phenyl, 4-(ethylphosphonomethyl)phenyl, 4-(ethyl, methylphosphonomethyl)phenyl, 4-(benzyl, ethylphosphonomethyl)phenyl, 4-(ethyl,i-propylphosphonomethyl)phenyl, 4-(diethylphosphonomethyl)phenyl, 4-(dimethylphosphonomethyl)phenyl, 4-(di-n-butylphosphonomethyl)phenyl,

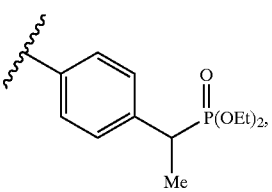

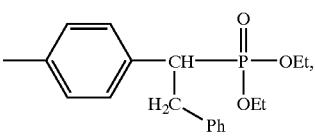

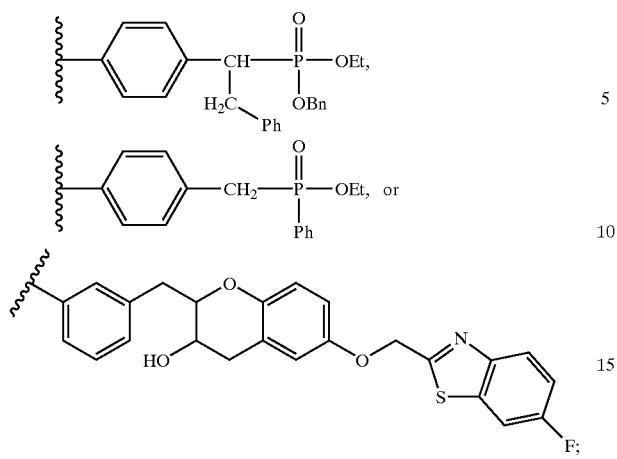

when R4, R5, and R6 are all hydrogen, R2 is benzyl or methyl, and R3 is methoxy, then R1 cannot be 4-(diethylphosphonomethyl)phenyl;

when R2, R4, R5, and R6 are all hydrogen and R3 is ethoxy, then R1 cannot be phenyl, 4-n-butoxyphenyl, 4-i-propoxyphenyl, 4-methoxyphenyl, or 4-ethoxyphenyl;

when R2, R4, R5, and R6 are all hydrogen and R3 is n-propoxy, then R1 cannot be 4-ethoxyphenyl;

when R2, R4, R5, and R6 are all hyarogen and R3 is methyl, then R1 cannot be phenyl, 4-guanidinophenyl, 4-(diethylphosphonomethyl)phenyl, when R2, R4, R5, and R6 are all hydrogen and R3 is trifluoromethyl, then R1 cannot be either 4-guanidinophenyl or 2,6-difluorophenyl;

when R2, R4, R5, and R6 are all hydrogen and R3 is nitro, then R1 cannot be either phenyl or 4-guanidinophenyl;

when R4, R5, and R6 are all hydrogen, R2 is ethyl, and R3 is chloro, then R1 cannot be phenyl;

when R2, R4, R5, and R6 are all hydrogen and R3 is chloro, then R1 cannot be 4-(diethylphosphonomethyl)phenyl, phenyl, 3,5-dibromo-3-hydroxyphenyl, or

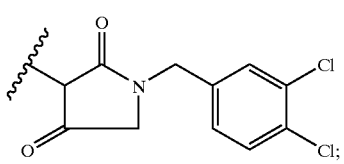

when R2, R4, R5, and R6 are all hydrogen and R3 is trifluoromethoxy, then R1 cannot be 4-(diethylphosphonomethyl)phenyl;

when R2, R3, R5 and R6 are all hydrogen and R4 is sulfo, then R1 cannot be

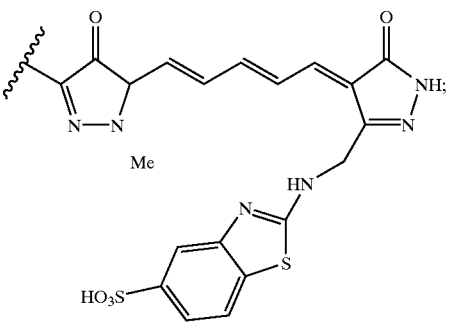

when R2, R3, R5 and R6 are all hydrogen and R4 is carboxy, then R1 cannot be:

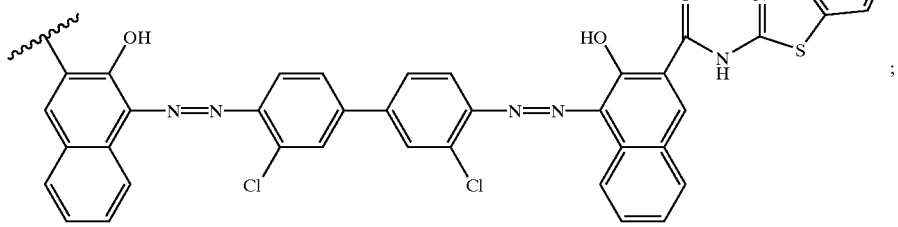

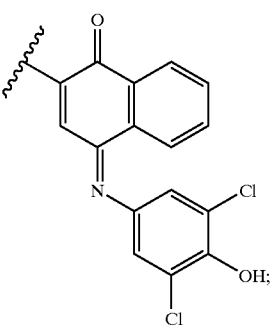

when R2, R3, R5, and R6 areall hydrogen and R4 is carbamoyl, then R1 cannot be 4-guanidinophenyl;

when R2, R3, R5, and R6 are all hydrogen and R4 is fluoro, then R1 cannot be 4-(guanidinomethyl)phenyl or

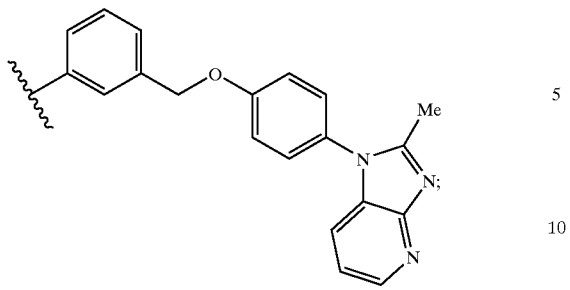

when R2, R3, R5, and R6 are all hydrogen and R4 is chloro, then R1 cannot be phenyl, 4-chlorophenyl,

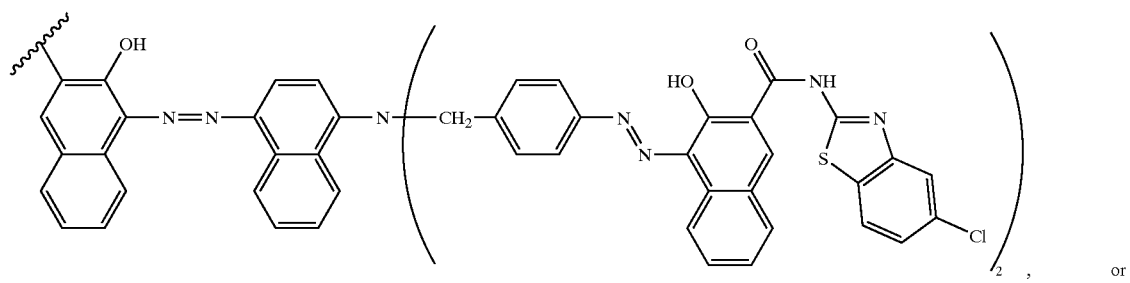

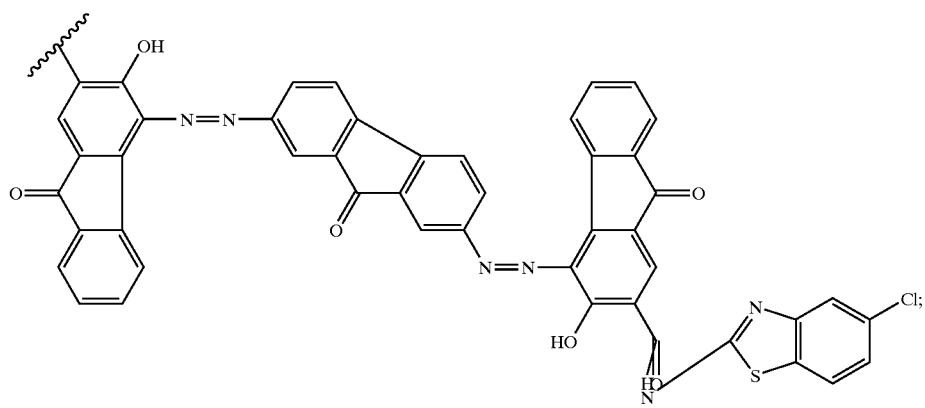

when R2, R3, R5, and R6 are all hydrogen and R4 is nitro, then R1 cannot be phenyl;

when R2, R3, R5, and R6 are all hydrogen and R4 is trifluoromethyl, then R1 cannot be 2,6-difluorophenyl;

when R2, R3, R5, and R6 are all hydrogen and R4 is methyl, then R1 cannot be phenyl;

when R2, R3, R5, and R6 are all hydrogen and R4 is phenyl, then R1 cannot be

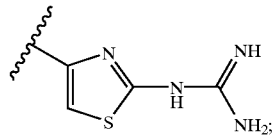

when R2, R3, R5, and R6 are all hydrogen and R4 is 4-(trifluoromethyl)benzoyl, then R1 cannot be 2,6-difluorophenyl or 2-chloro-6-fluorophenyl;

when R2, R3, R5, and R6 are all hydrogen and R4 is methoxy, then R1 cannot be phenyl;

when R2, R3, R5, R6 are all H and R4=

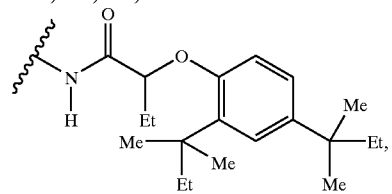

R1 cannot be

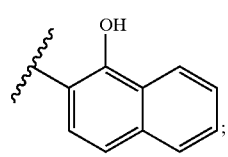

when R2, R3, R5, and R6 are all hydrogen and R4 is ethoxy, then Recombinant cannot be

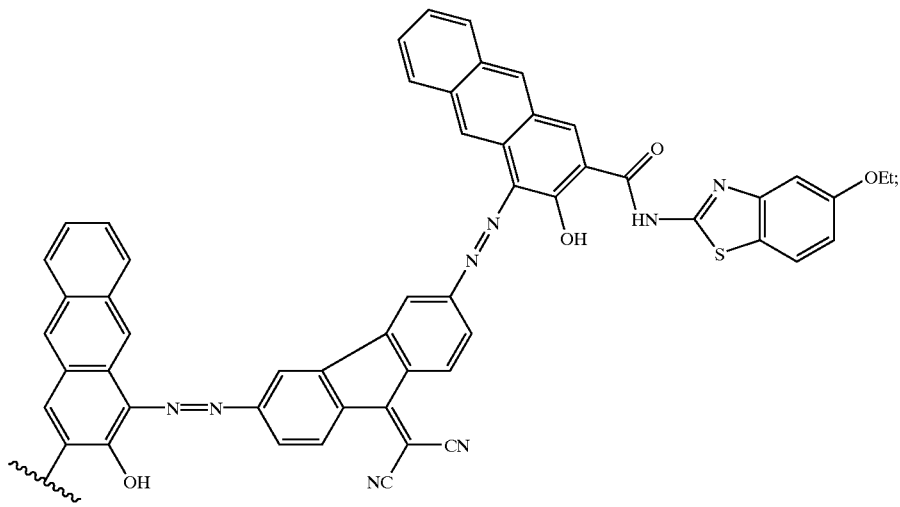
when R2, R3, R4, and R6 are all hydrogen and R5 is fluoro, then R1 cannot be phenyl, 2-aminophenyl, 4-nitrophenyl, 4-(diethylphosphonomethyl)phenyl, or
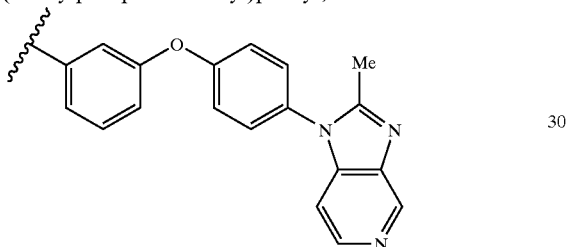
when R2, R3, R4, and R6 are all hydrogen and R5 is chloro, then R1 cannot be phenyl, 2-aminophenyl, 4-aminophsnyl, 2-fluorophenyl, 2,6-difluorophenyl, 4-nitrophenyl, 3,5-dinitrophenyl, 4-guanidophenyl, 4-(guanidinomethyl)phenyl,
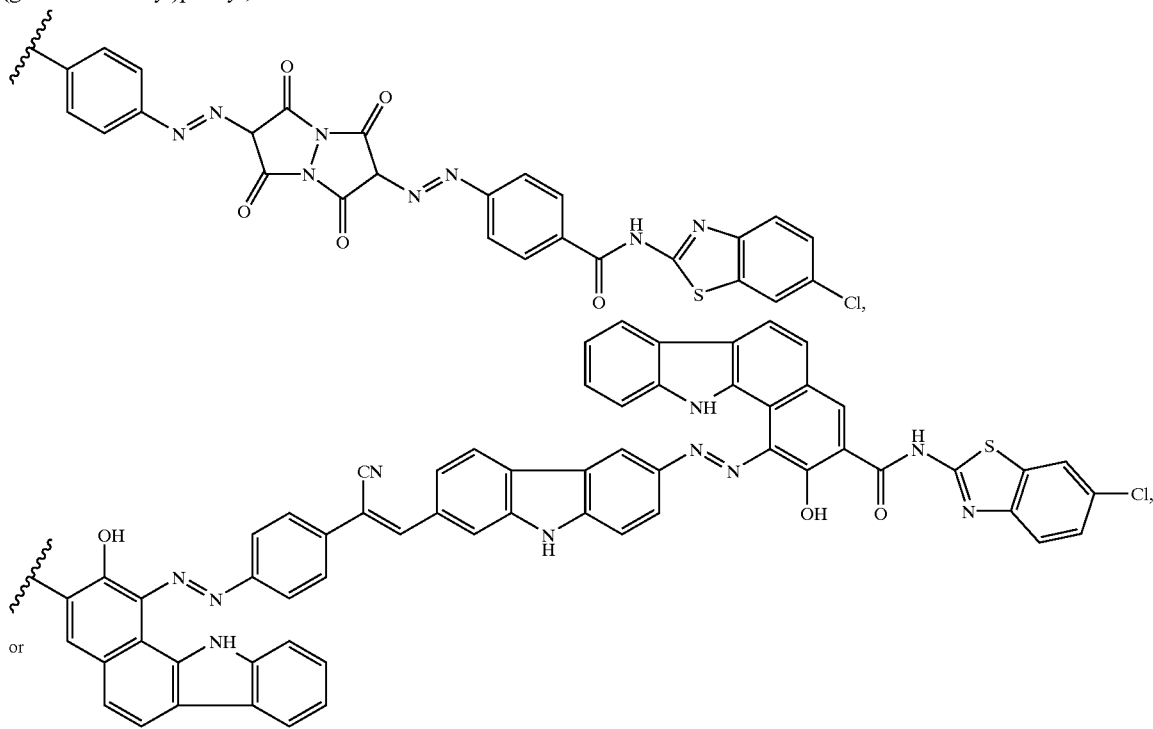
or

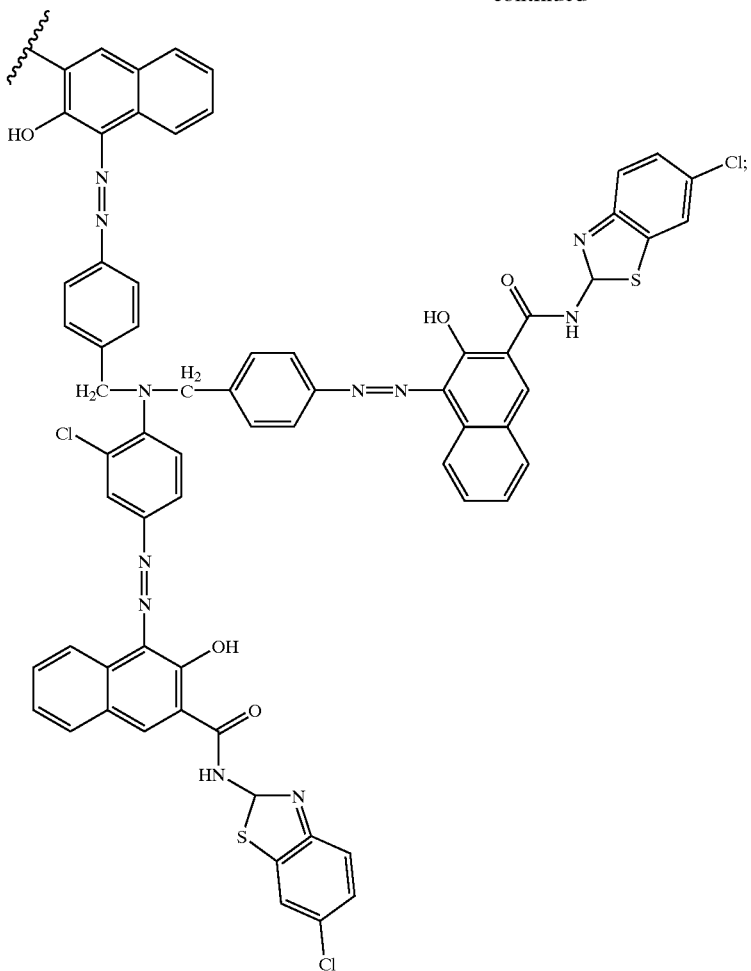

when R2, R3, R4, and R6 are all hydrogen and R5 is bromo, then R1 cannot be phenyl, 4-methoxyphenyl, 4-ethoxyphenyl, 4-n-butoxyphenyl, 4-i-butoxyphenyl, 4-n-propoxyphenyl, 4-i-propoxyphenyl, 4-nitrophenyl, 4-guanidinophenyl,4-(diethylphosphonomethyl)phenyl or

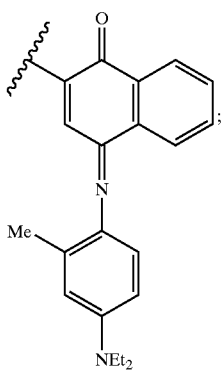

when R2, R3, R4, and R6 are all hydrogen and R5 is iodo, then R1 cannot be phenyl or 4-nitrophenyl;

when R2, R3, R4, and R6 are all hydrogen and R5 is amino, then R1 is amino, then R1 cannot be 4-guanidinophenyl;

when R2, R3, R4, and R6 are all hydrogen and R5 is acetamido, then R1 cannot be phenyl;

when R2, R3, R4, and R6 are all hydrogen and R5 is diethylamino, then R1 cannot be phenyl;

when R2, R3, R4, and R6 are all hydrogen and R5 is nitro, then R1 cannot be phenyl, 4-nitrophenyl, 4-methoxyphenyl, 4-ethoxyphenyl, 4-n-butoxyphenyl, 4-guanidinophenyl, 4-(guanidinomethyl)phenyl, 3-(guanidinomethyl)phenyl, 4-(diethylphosphonomethyl) phenyl, 3,5-dinitrophenyl,

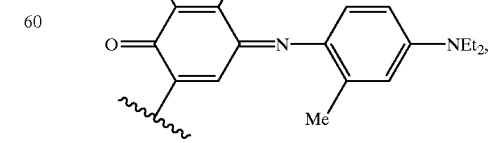

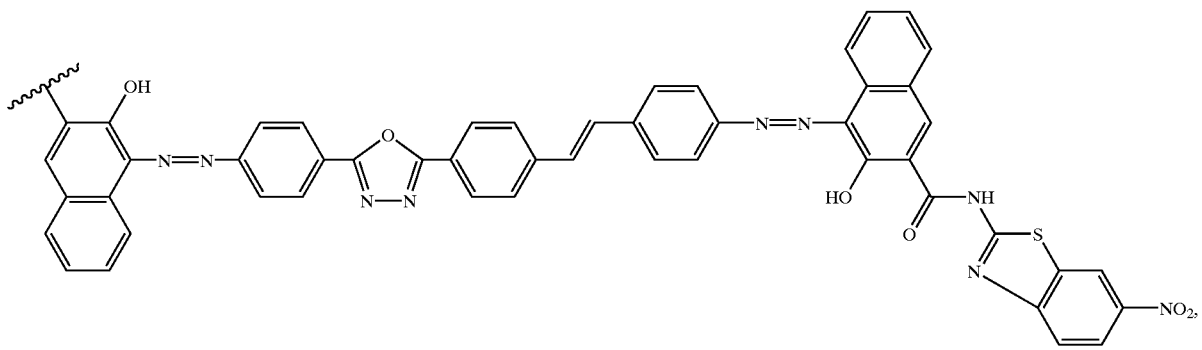

or

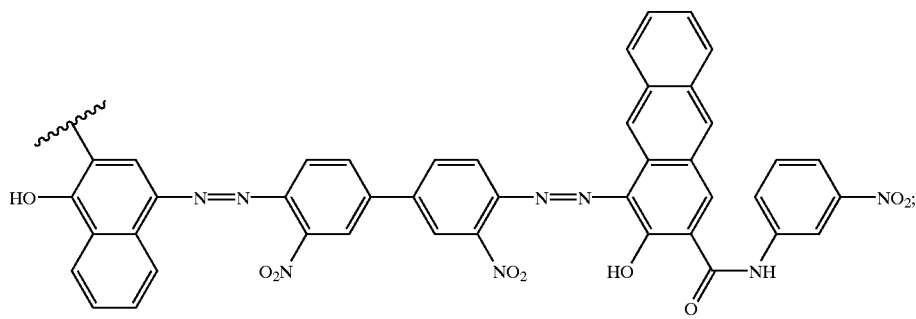

when R2, R3, R4, and R6 are all hydrogen and R5 is carboxy, then R1 cannot be phenyl;

when R2, R3, R4, and R6 are all hydrogen and R5 is carbamoyl, then R1 cannot be 4-guanidinophenyl, 4-(diethylphosphonomethyl)phenyl, or 4-(guanidinomethyl)phenyl;

when R2, R3, R4, and R6 are all hydrogen and R5 is cyano, then R1 cannot be 4-guanidinophenyl or

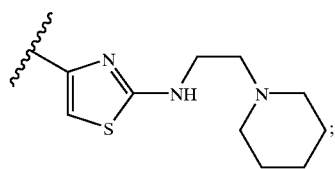

when R2, R3, R4, and R6 are all hydrogen and R5 is carbethoxmethoxy, then R1 cannot be 4-(diethylphosphonomethyl)phenyl;

when R2, R3, R4, and R6 are all hydrogen and R5 is carbethoxy, then R1 cannot be 4-(diethylphosphonomethyl)phenyl;

when R2, R3, R4, and R6 are all hydrogen and R5 is 2-hydroxyethyl, then R1 cannot be 4-guanidinophenyl;

when R2, R3, R4, and R6 are all hydrogen and R5 is methyl, then R1 cannot be phenyl, 4-chlorophenyl, 4-methylphenyl, 4-methoxyphenyl, 4-guanidinophenyl, 4-(diethylphosphonomethyl)phenyl, 4-hydroxy-3-iodo-5-nitrophenyl,

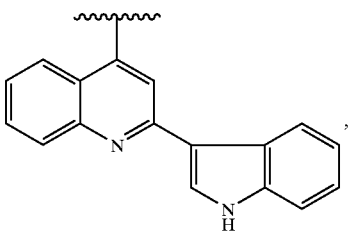

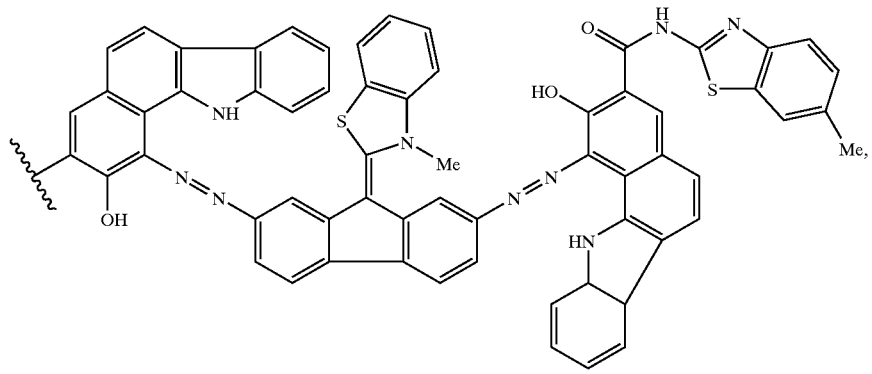

-continued

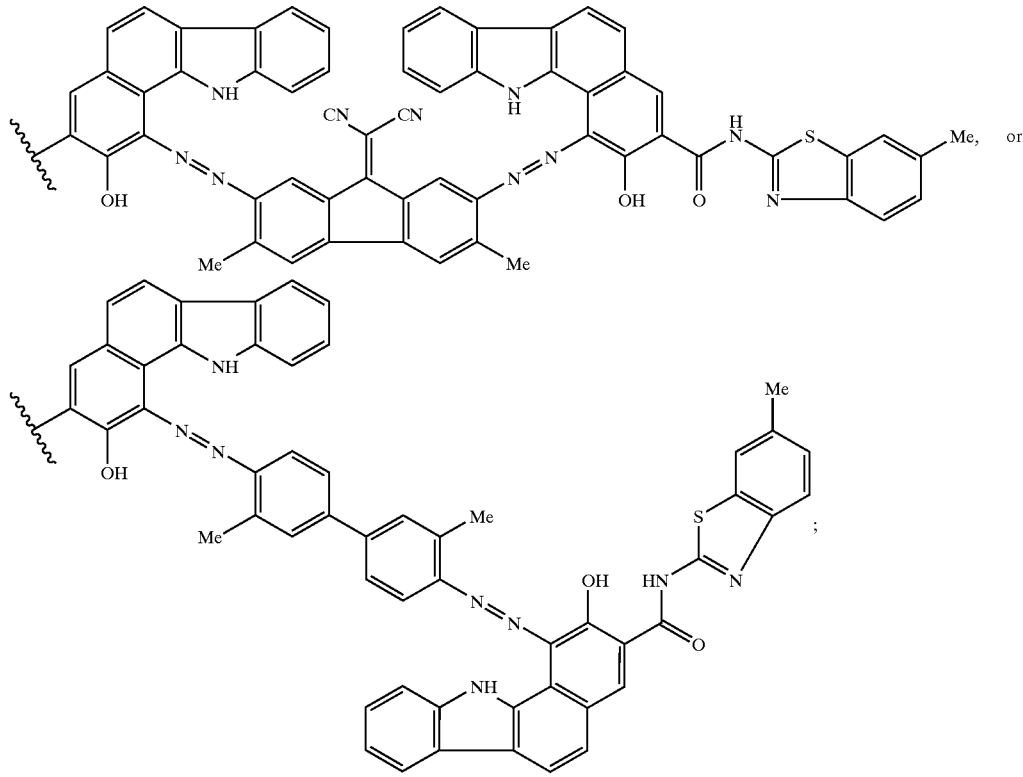

when R2, R3, R4, and R6 are all hydrogen and R5 is n-butyl, then R1 cannot be phenyl;
when R2, R3, R4, and R6 are all hydrogen and R5 is thiomethyl, then R1 cannot be 4-guanidinophenyl or 4-(diethylphosphonomethyl)phenyl;
when R2, R3, R4, and R6 are all hydrogen and R5 is methylsulfinyl, then R1 cannot be 4-guanidinophenyl;
when R2, R3, R4, and R6 are all hydrogen and R5 is methylsulfonyl, then R1 cannot be 4-guanidinophenyl;
when R2, R3, R4, and R6 are all hydrogen and R5 is sulfamoyl, then cannot be phenyl, 4-guanidinophenyl, or 3,5-dinitrophenyl;
when R3, R4, and R6 are all hydrogen, R2 is phenyl, and R5 is sulfo, then R1 cannot be

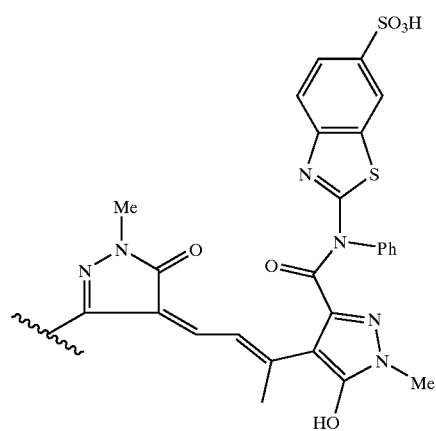

when R2, R3, R4, and R6 are all hydrogen and R5 is $SCH_2CF_3$, then R1 cannot be 2,6-difluorophenyl;

when R2, R3, R4, and R6 are all hydrogen and R5 is $SOCF_3$, then R1 cannot be 2,6-d) whenluorophenyl;
when R2, R3, R4, and R6 are all hydrogen and R5 is $SCF_3$, then R1 cannot be 2,6-difluorophenyl or 2-chlorophenyl;
when R2, R3, R4, and R6 are all hydrogen and R5 is i-propyl, then R1 cannot be 4-guanidinophenyl;
when R2, R3, R4, and R6 are all hydrogen and R5 is trifluoromethyl, then R1 cannot be 4-guanidinophenyl, 4-(diethylphosphonomethyl)phenyl, 4-(guanidinomethyl)phenyl, 2-fluorophenyl, 2-methylphenyl, 2-chloro-6-fluorophenyl, 2-chlorophenyl, or 2,6-difluorophenyl;
when R2, R3, R4, and R6 are all hydrogen and R5 is trifluoromethoxy, then R1 cannot be 2-trifluoromethylphenyl, 2-methoxyphenyl, 2-bromophenyl, 2-chlorophenyl, 2-methylphenyl, 2-chloro-6-fluorophenyl, 2,4-dichlorophenyl, 2,6-difluorophenyl, or 3,5-dichlorophenyl;
when R2, R3, R4, and R6 are all hydrogen and R5 is OCHFz, then R1 cannot be 2,6-difluorophenyl;
when R2, R3, R4, and R6 are all hydrogen and R5 is $OCF_2CHF_2$, then R1 cannot be 2,6-difluorophenyl;
when R2, R3, R4, and R6 are all hydrogen and R5 is $OCF_2CHF_3$, then R1 cannot be 2-chlorophenyl or 2,6-difluorophenyl;
when R2, R3, R4, and R6 are all hydrogen and R5 is 2-chloro-4(trifluoromethoxy)phenoxy, then R1 cannot be 2-chlorophenyl, 2,6-difluorophenyl, or 2-chloro-6-fluorophenyl;
when R2, R3, R4, and R6 are all hydrogen and R5 is 2,3,4,5-tetrabromo-6-cyanophenyl;
when R2, R3, R4, and R6 are all hydrogen and R5 is methoxy, then R1 cannot be phenyl, 4-methoxyphenyl, 4-ethoxyphenyl, 4-n-propoxy)phenyl, 4-(i-propoxy)phenyl, 4-n-butoxy)phenyl, 4-(i-butoxy)phenyl, 4-(n-pentoxy)phenyl, 4-(3-methylbutoxy)phenyl, 4-methylphenyl, 4-chlorophenyl, 3,4-diaminophenyl, 4-amino-3-nitrophenyl, 4-acetamido-3-nitrophenyl, 2-fluorophenyl, 4-(diethylphosphonomethyl)phenyl,

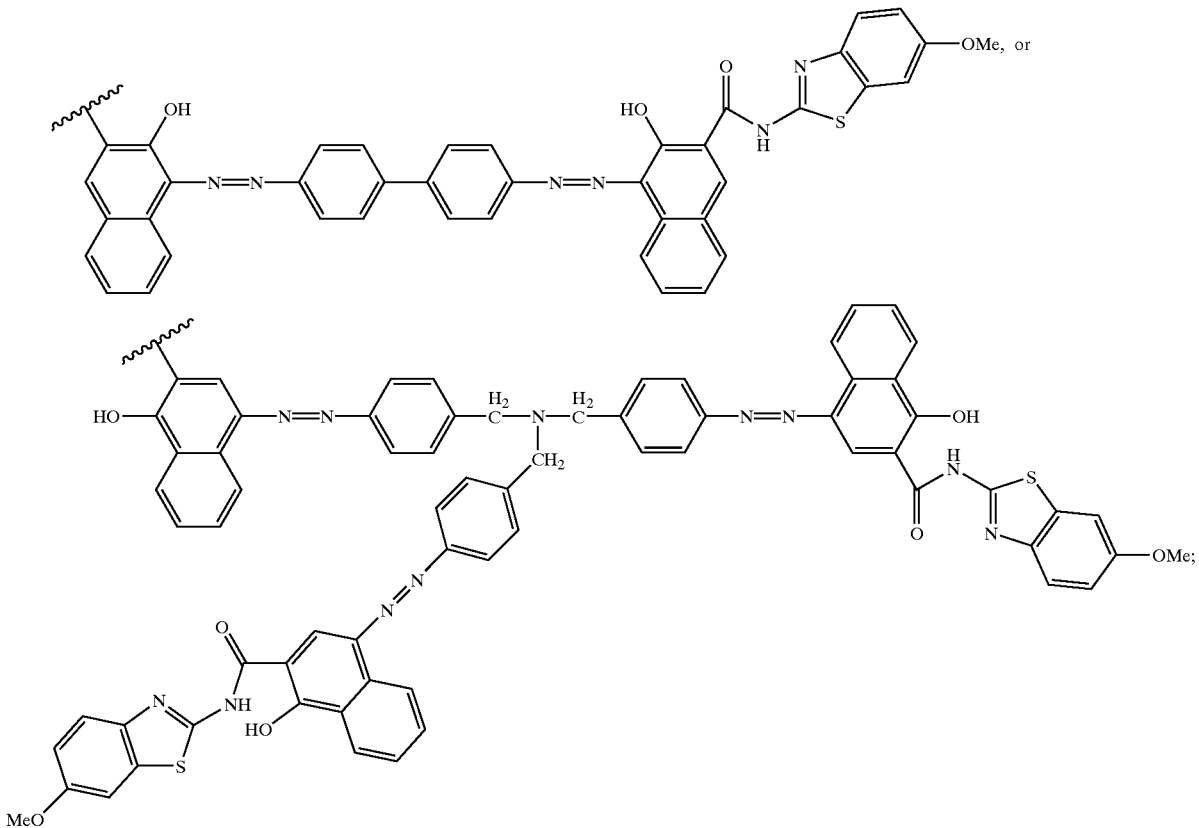

when R2, R3, R4, and R6 are all hydrogen and R5 is n-propoxy, then R1 cannot be phenyl, 4-methoxyphenyl, 4-ethoxyphenyl, 4-(n-propoxy)phenyl, 4-(i-propoxy) phenyl, or 4-(n-butoxy)phenyl;

when R2, R3, R4, and R6 are all hydrogen and R5 is ethoxy, then R1 cannot be phenyl, 4-hydroxyphenyl, 4-methoxyphenyl, 4-ethoxyphenyl, 4-(n-propoxy)phenyl, 4-(i-propoxy)phenyl, 4-(n-butoxy)phenyl, 4-(i-butoxy) phenyl, 2-fluorophenyl, 4-guanidinophenyl, 4-(diethylphosphonomethyl)phenyl, 2-(di-(4'-hydroxyphenyl)methyl)phenyl,

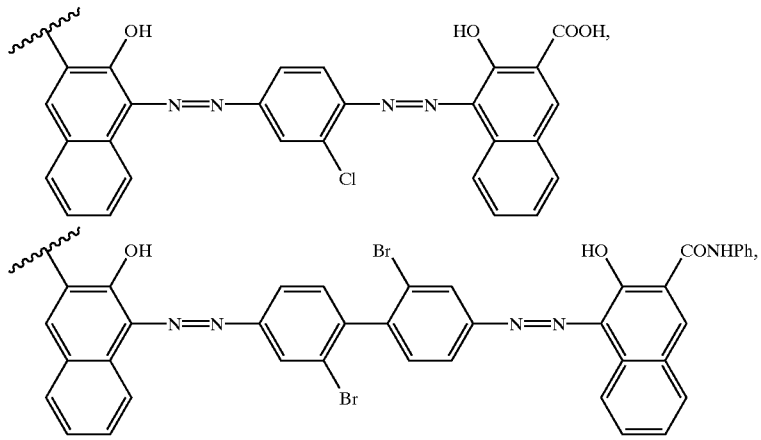

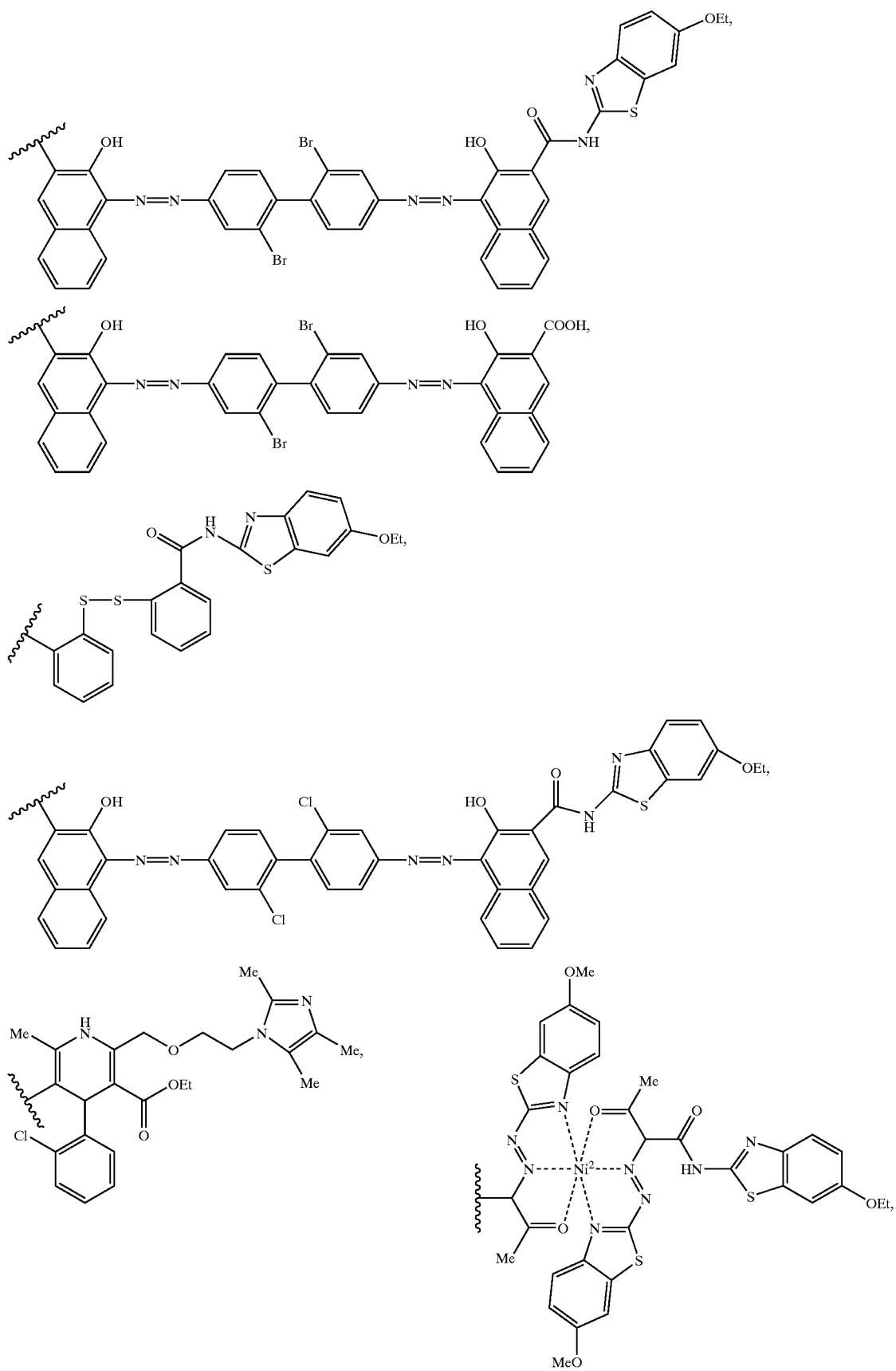

-continued
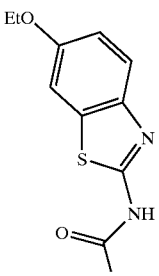
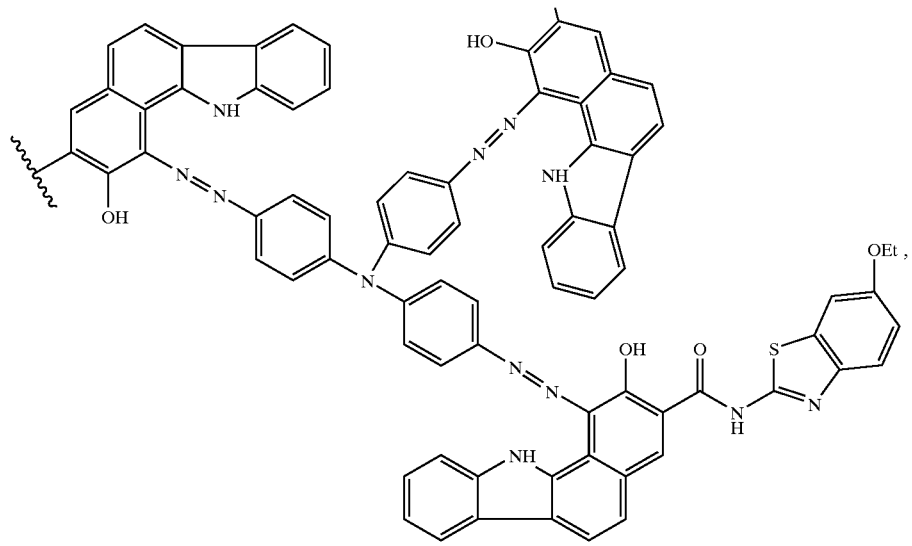
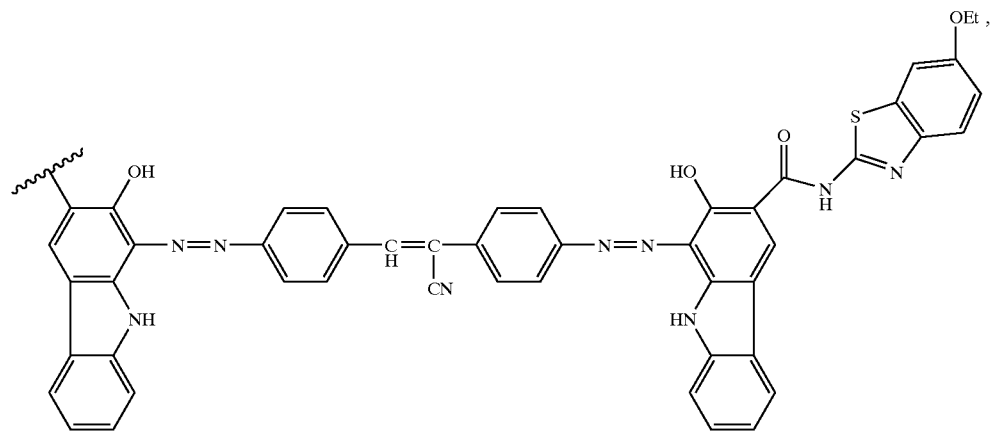
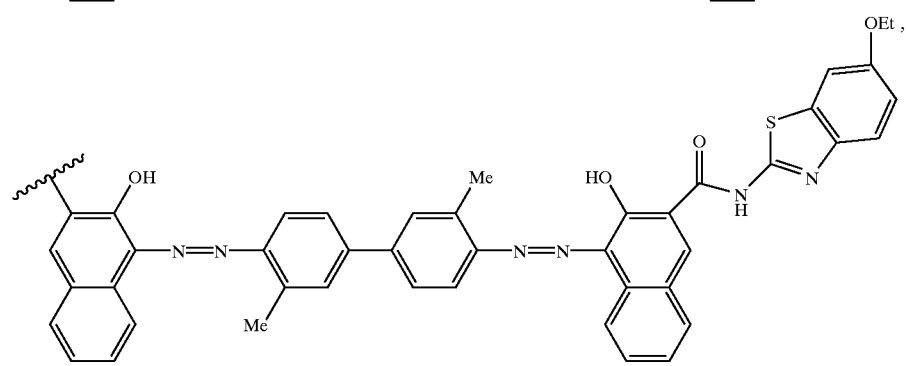

-continued
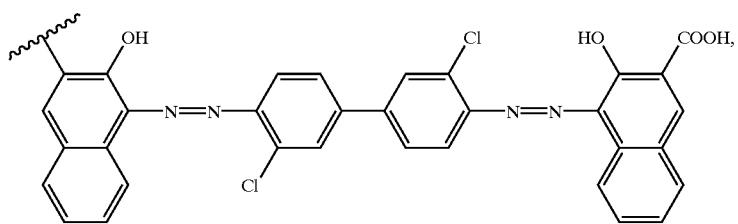
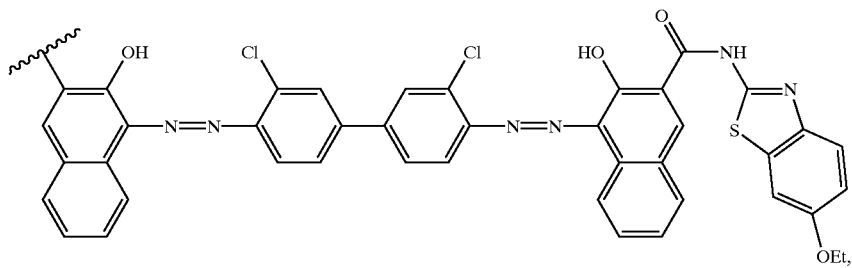
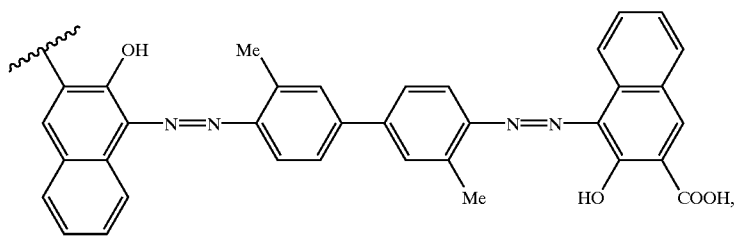
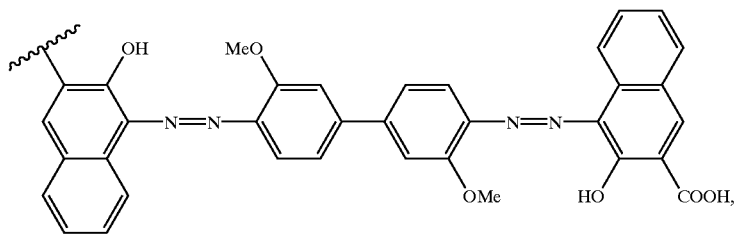
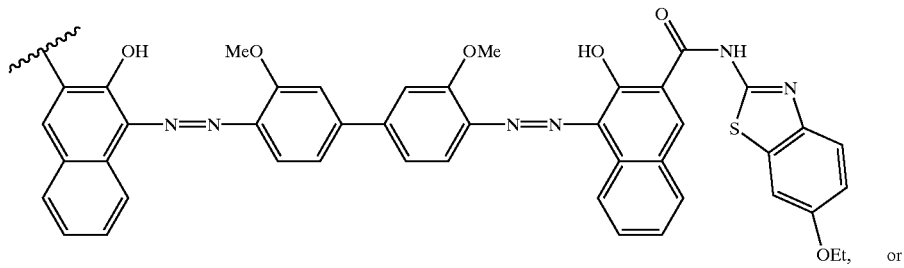
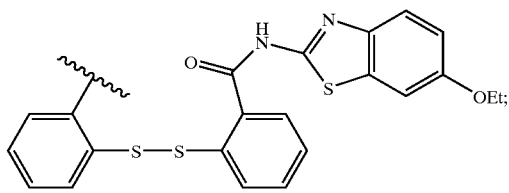

when R2, R3, R4, and R6 are all hydrogen and R5 is i-propoxy, then R1 cannot be phenyl, 4-methoxyphenyl, or 4-ethoxyphenyl;

when R2, R3, R4, and R6 are all hydrogen and R5 is n-butoxy, then R1 cannot be phenyl, 4-methoxyphenyl, 4-ethoxyphenyl, or 4-(n-butoxy)phenyl;

when R2, R3, R4, and R6 are all hydrogen and R5 is i-butoxy, then R1 cannot be 4-methoxyphenyl;

when R2, R3, R4, and R6 are all hydrogen and R5 is benzyloxy, then R1 cannot be 4-(diethylphosphonomethyl)phenyl;

when R2, R3, R4, and R6 are all hydrogen and R5 is phenyl, then R1 cannot be 3-(guanidinomethyl)phenyl, 4-(guanidinomethyl)phenyl, 2,6-difluorophenyl,

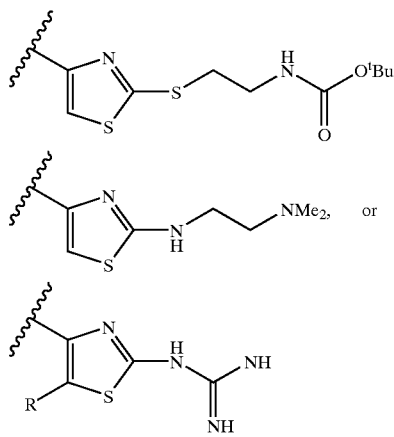

where R is hydrogen, methyl, ethyl n-propyl, or i-propyl;

when R2, R3, R4, and R6 are all hydrogen and R5 is 4-fluorophenyl, then R1 cannot be

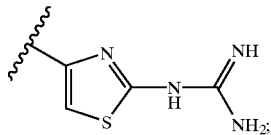

when R2, R3, R4, R6 are all H, R5 is phenylazo, then R1 cannot be phenyl;

when R2, R3, R4, and R5 are all hydrogen and R6 is nitro, then R1 cannot be phenyl;

when R2, R3, R4, and R5 are all hydrogen and R6 is phenyl, then R1 cannot be

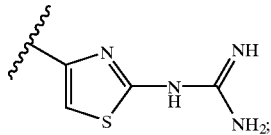

when R2, R3, and R4 are all hydrogen, R5 is 2-chloro-4-(trifluormethyl)phenoxy, and R6 is either methyl or hydrogen, then R1 cannot be 2-chlorophenyl 2-chloro-6-fluorophenyl, or 2,6-difluorophenyl;

when R2, R4, and R5 are all hydrogen, R3 is methyl and R5 is $SCH_2CO_2Et$, then R1 cannot be 4-cyanophenyl;

when R2, R3, R6 are all H, R4 and R5 both equal Me, then R1 cannot be 4-guanidinophenyl, 2-hydroxyphenyl, 4-(diethoxyphosonylmethyl)phenyl,

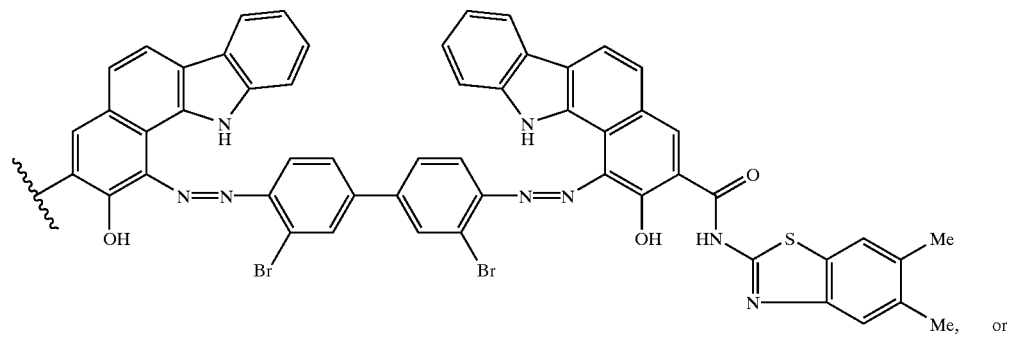

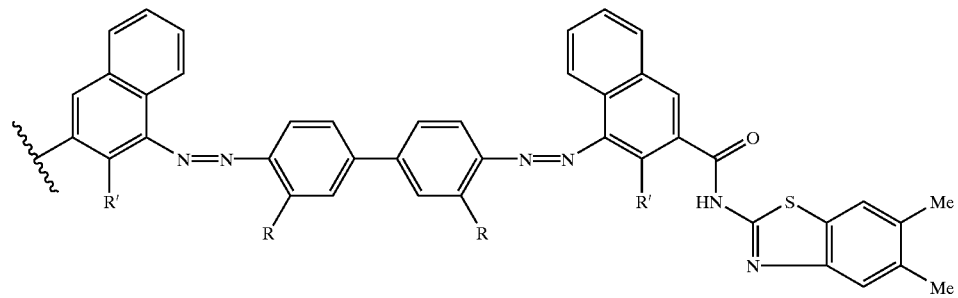

in which R is either Cl or Me and R' is H or OH; when R2, R5, R6 equal H and R3 and R4 together equal —CH═CH—CH═CH—, then R1 cannot be phenyl, 4-(3'-(diethylphosphono)propyloxyphenyl, 4-(diethylphosphonomethyl)phenyl, 4-methylphenyl, 4-nitrophenyl, 4-chlorophenyl,
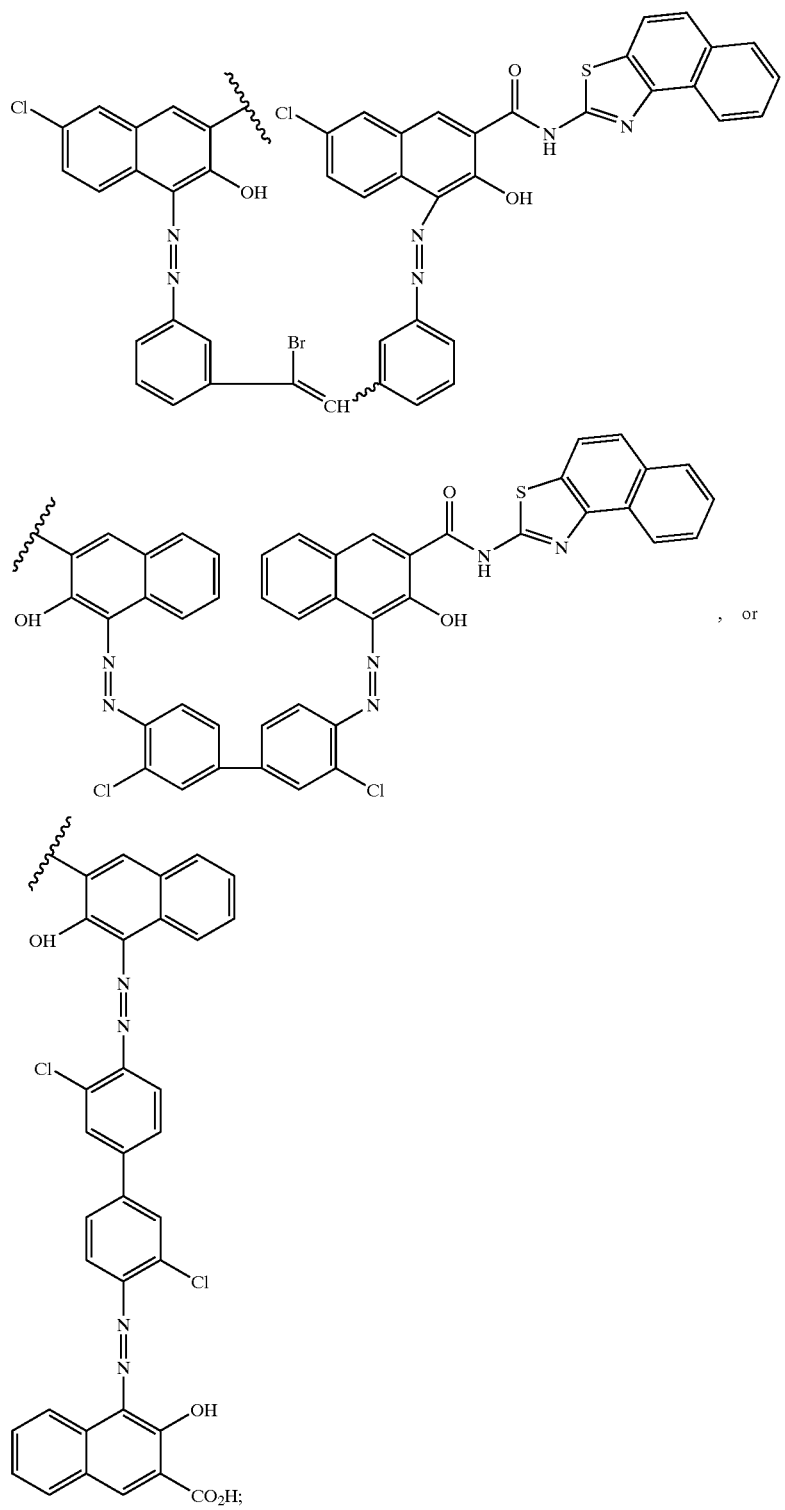

when R2, R3, and R6 are all hydrogen and R4 and R5 both equal carbomethoxy, then R1 cannot be

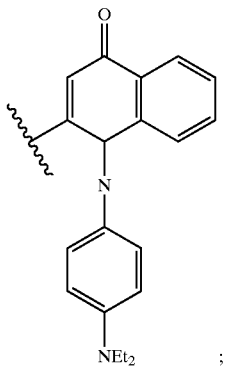

;

when R2, R4 and R6 are all hydrogen, R3 is methoxy, and R5 is phenyl, then R1 cannot be:

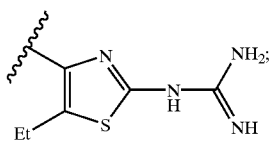

when R2, R3, and R6 are all hydrogen, and R4 and R5 both equal methoxy, then R1 cannot be:

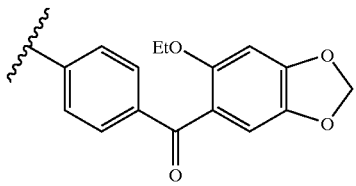

when R2, R3, and R6 are all hydrogen, R4 is chloro, and R5 is nitro,

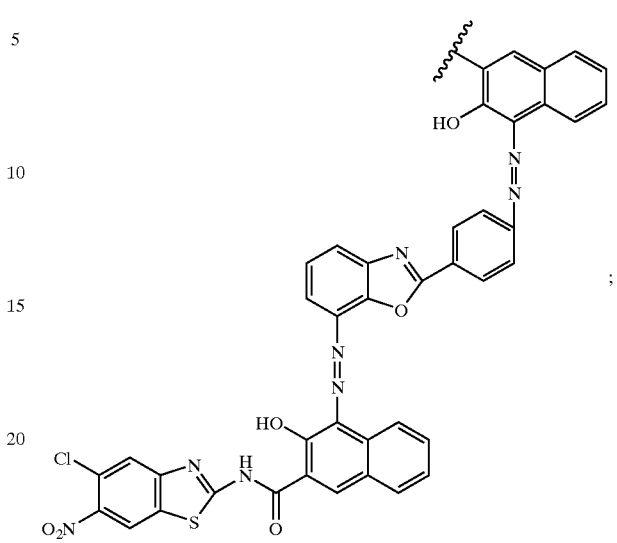

;

then R1 cannot be:

when R2, R4, and R6 are all hydrogen, R3 is benzoyl, and R5 is chloro, then R1 cannot be 4-(diethylphosphonomethyl)phenyl;

when R2, R4 and R6 are all hydrogen, R3 is phenyl, and R5 is bromo, then R1 cannot be 4-(diethylphosphonomethyl)phenyl;

when R2, R3, R4 are all hydrogen and R5 and R6 together equal —CH=CH—CH=CH—, then R1 cannot be 2-hydroxyphenyl

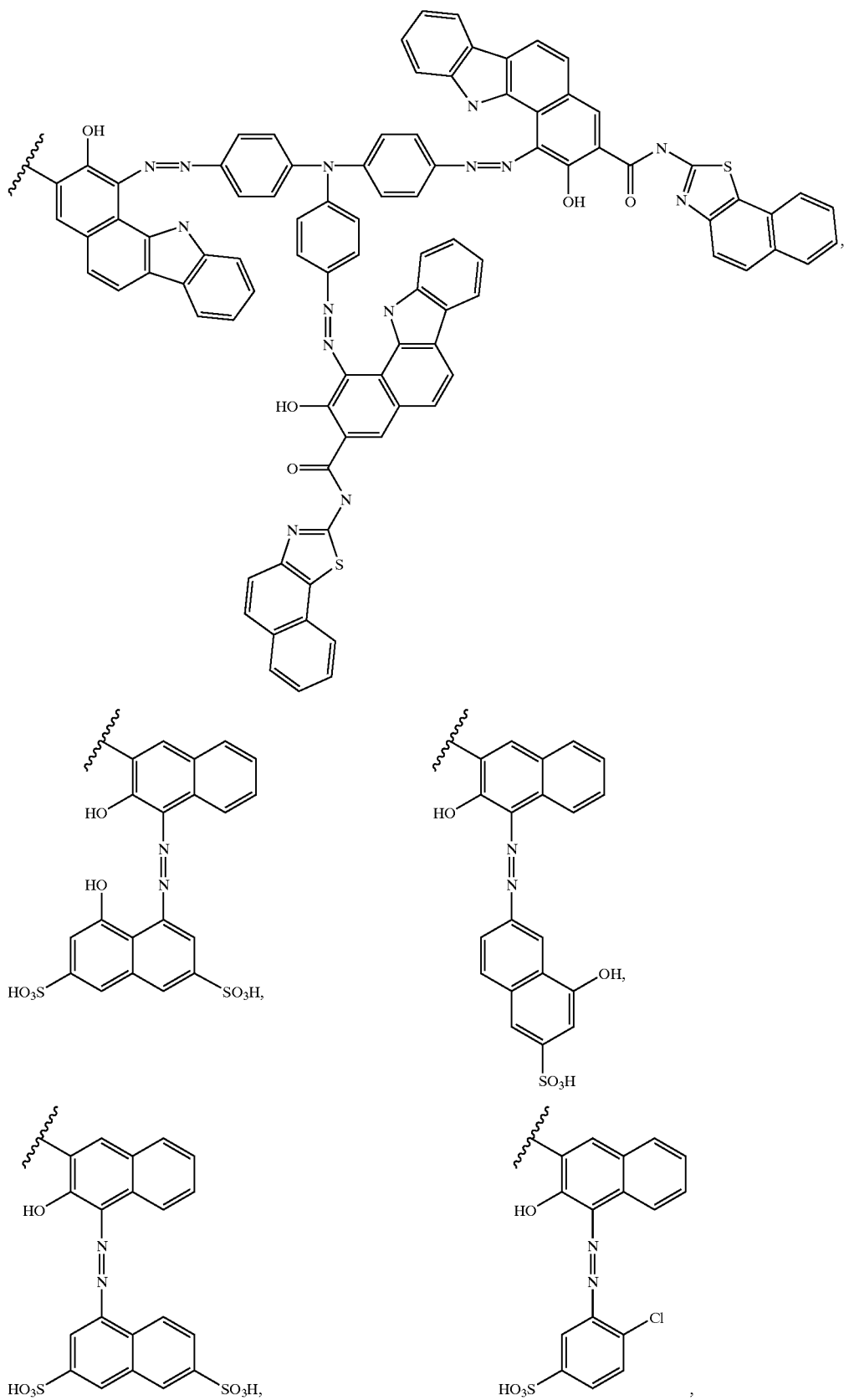

-continued
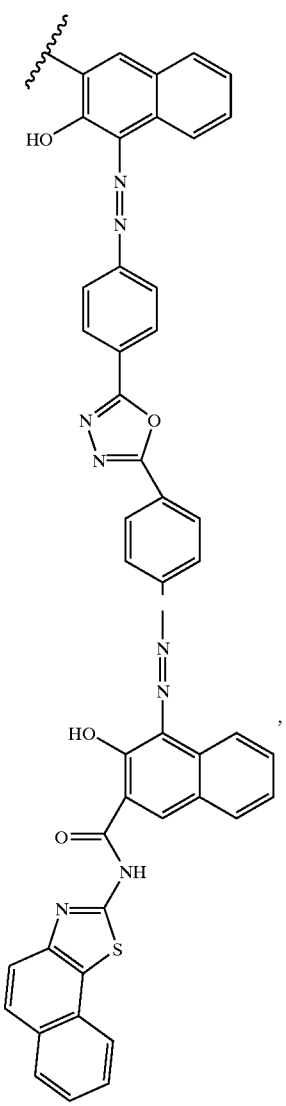
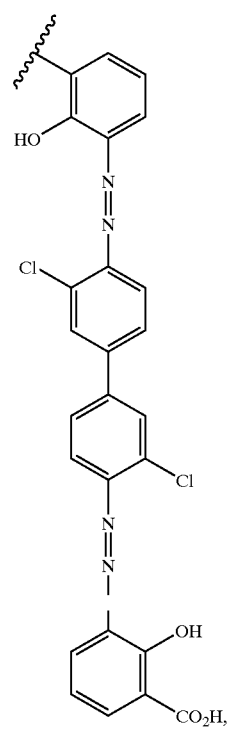
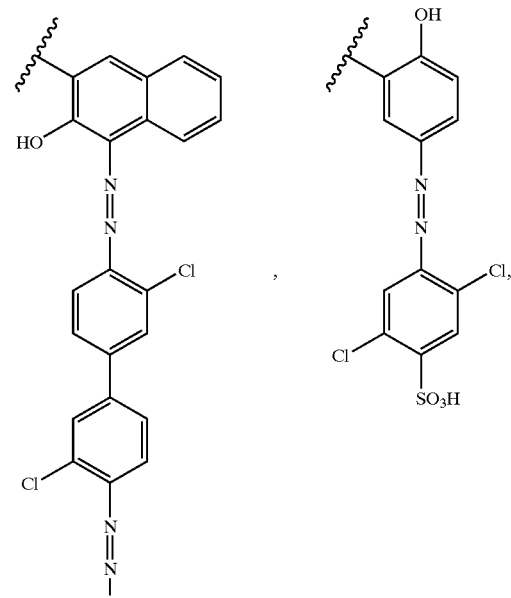
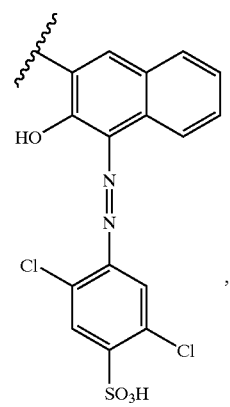

-continued
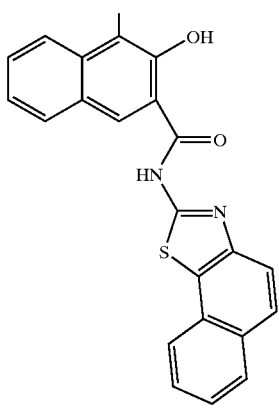
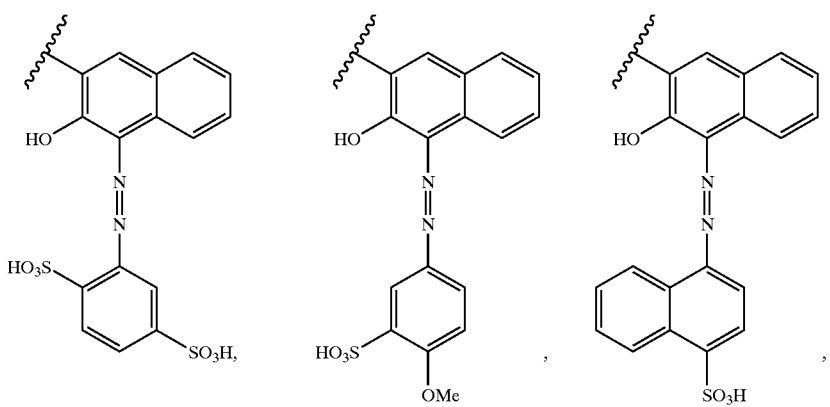
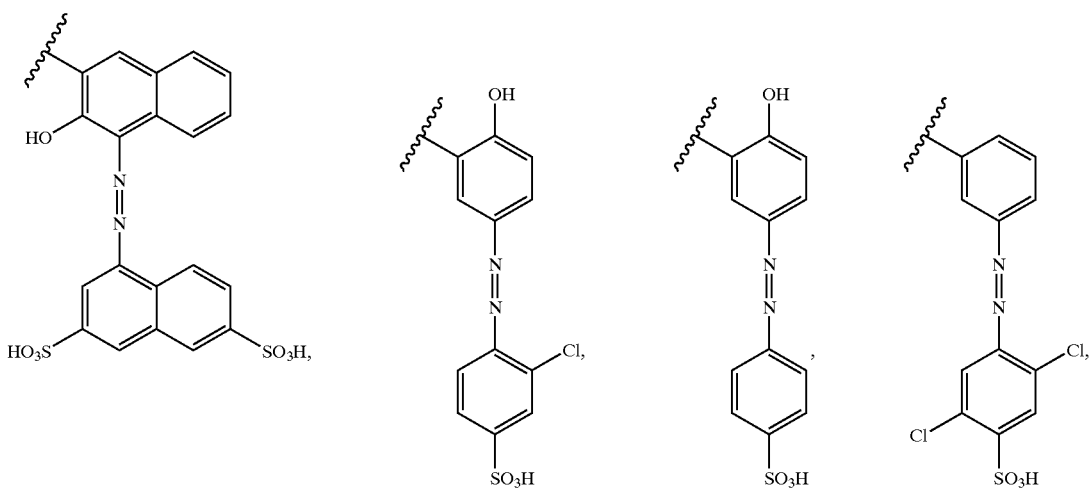

-continued
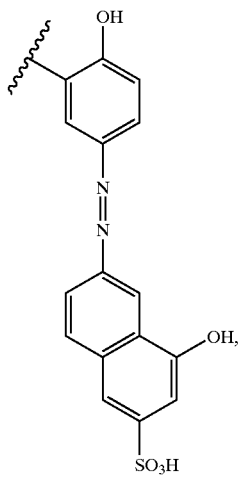 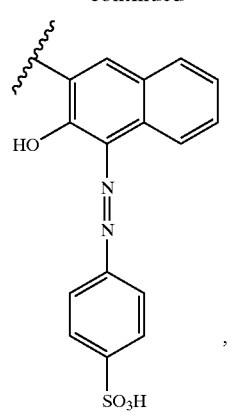 , 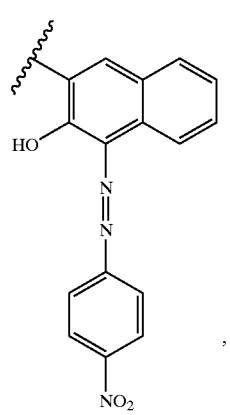 ,
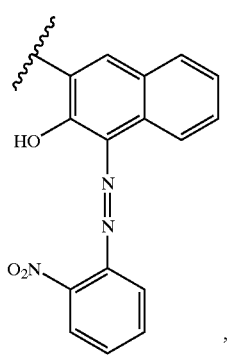 , 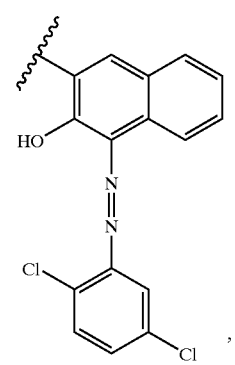 , 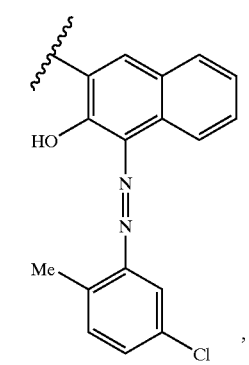 ,
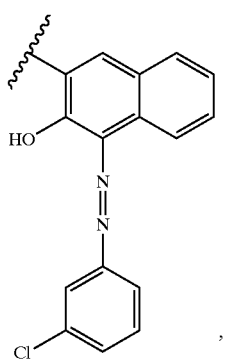 , 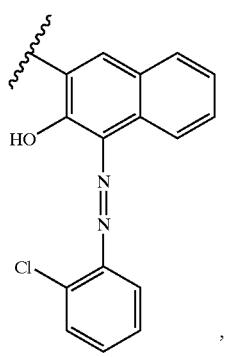 , 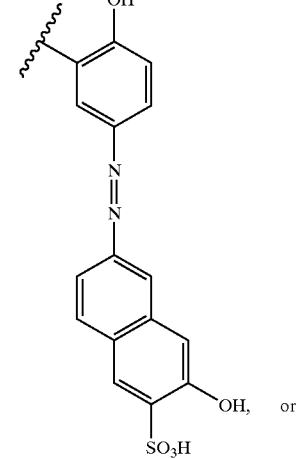 or
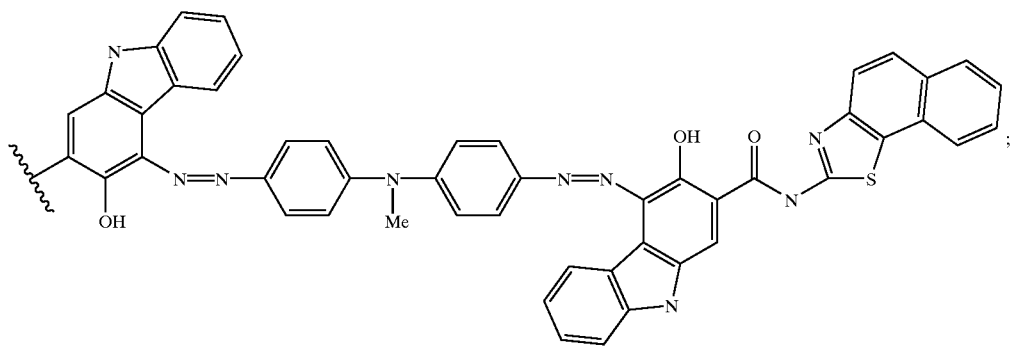;

when R2, R3, and R4 are all hydrogen, R5 and R6 together equal —CO—CH=C(Ph)—O—, then R1 cannot be phenyl, 4-methylphenyl, 4-chlorophenyl, or 4-methoxyphenyl;

when R2, R3, and R4 are all hydrogen, R5 and R6 together equal —S—C(NHCOPh)=N—, then R1 cannot be phenyl;

when R2, R3 and R5 are all hydrogen and R4 and R5 together equal —CH=CH—CH=CH—, then R1 cannot be phenyl;

when R2, R3 and R5 are all hydrogen and R4 and R5 together equal —OCF$_2$CF$_2$O—, then R1 cannot be 2-chlorophenyl or 2,6-difluorophenyl;

when R2, R3, and R4 are all hydrogen and R5 and R6 together equal —OCF$_2$CF$_2$O—, then R1 cannot be 2-chlorophenyl or 2,6-difluorophenyl;

when R2, R4, and R6 are all hydrogen and R3 and R5 both equal chloro, then R1 cannot be phenyl or 4-nitrophenyl;

when R2, R4, and R6 are all hydrogen and R3 and R5 both equal bromo, then R1 cannot be phenyl or 4-nitrophenyl;

when R2, R4, and R6 are all hydrogen and R3 and R5 both equal methoxy, then R1 cannot be 4-(diethylphosphonomethyl)phenyl;

when R2, R4, and R6 are all hydrogen, R3 is methoxy and R5 is nitro, then R1 cannot be 4-guanidinophenyl or 4-(guanidinomethyl)phenyl;

when R2, R4, and R6 are all hydrogen, R3 is COCH$_3$ and R5 is bromo, then R1 cannot be equal 4-(diethylphosphonomethyl)phenyl;

when R2, R4, and R5 are all hydrogen, R3 is methoxy and R6 is chloro, then R1 cannot be 4-guanidinophenyl;

when R2, R3, and R6 are all hydrogen, R4 is fluoro and R5 is thiocyano, then R1 cannot be phenyl or 4-nitrophenyl;

when R2, R3, and R6 are all hydrogen, R4 is chloro, and R5 is methoxy, then R1 cannot be equal 4-(diethylphosphonomethyl)phenyl;

when R2 and R3 both equal hydrogen and R4, R5 and R6 are all bromo, then R1 cannot be phenyl or 4-nitrophenyl;

when R2 and R3 both equal hydrogen and R4, R5 and R6 are all methoxy, then R1 cannot be phenyl;

when R2 and R3 both equal H, R4 and R6 are both chloro and R5 is phenoxy, then R1 cannot be either 2-chlorophenyl or 2,6-difluorophenyl;

when R2 and R3 both equal H, R4 and R6 are both chloro, R5 is 4-(trifluoromethyl)phenoxy, then R1 cannot be 2,6-difluorophenyl;

when R2 and R4 both equal hydrogen, R4 and R6 both equal chloro, and R5 is:

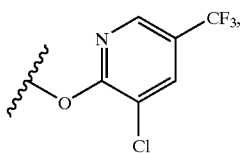

, then R1 cannot be either 2-chlorophenyl, or 2,6-difluorophenyl;

when R2 and R3 both equal hydrogen, R4 and R6 both equal chloro, and R5 is 4-(trifluoromethylthio)phenoxy, then R1 cannot be either 2-chlorophenyl or 2,6-difluorophenyl;

when R2 and R3 both equal hydrogen, R4 and R6 both equal chloro, and R5 is 4-(chloro)phenoxy, then R1 cannot be 2-chlorophenyl, 2-methylphenyl, 2-chloro-6-fluorophenyl, 2-chloro-3-pyridyl, or 2,6 difluorophenyl;

when R2 and R3 both equal hydrogen, R4 and R6 both equal chloro, and R5 is (2-chloro-4-trifluomethyl)phenoxy, then R1 cannot be 2,6-difluorophenyl;

when R2 and R3 both equal hydrogen, R4 and R6 both equal chloro, and R5 is:

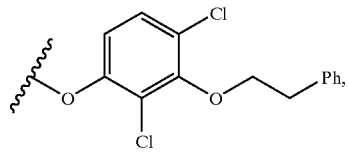

then R1 cannot be 2,6-difluorophenyl;

when R2 and R3 both equal hydrogen, R4 and R6 both equal chloro, and R5 is 2,4-dichlorophenoxy, then R1 cannot be either 2-chlorophenyl or 2,6-difluorophenyl;

when R2 and R3 both equal hydrogen, R4 and R6 both equal chloro, and R5 is 4-trifluoromethylphenoxy, then R1 cannot be either either 2-chlorophenyl or 2,6-difluorophenyl;

when R2 and R3 both equal hydrogen, R4 and R6 both equal chloro, and R5 is:

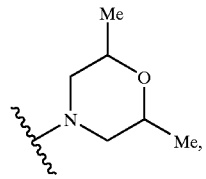

then R1 cannot be 2-chlorophenyl;

when R2 and R3 both equal hydrogen, R4 and R6 both equal chloro, and R5 is:

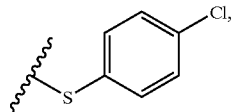

then R1 cannot be 2-chlorophenyl;

when R2 and R3 both equal hydrogen, R4 and R6 both equal chloro, and R5 is fluoro, then R1 cannot be 2,6-difluorophenyl;

when R2 and R3 both equal hydrogen, and R4, R5, and R6 are all chloro, then R1 cannot be either 4-nitrophenyl or phenyl;

when R2 and R3 both equal hydrogen, R4 and R6 both equal chloro, and R5 is OCF$_2$CF$_2$H$_1$, then R1 cannot be either 2-chlorophenyl or 2,6-difluorophenyl;

when R2 and R3 both equal hydrogen, R4 and R6 both equal chloro, and R5 is methoxy, then R1 cannot be 4-sulfamoylphenyl;

when R2 and R3 both equal hydrogen, R4 and R6 both equal chloro, and R5 is ethoxy, then R1 cannot be 2,6-difluorophenyl;

when R2 and R3 both equal hydrogen, R4 and R6 both equal chloro, and R5 is dimethylamino, then R1 cannot be either 2-chlorophenyl or 2,6-difluorophenyl;

when R2 and R3 both equal hydrogen, R4 and R6 both equal chloro, and R5 is SCH2CF3, then R2 cannot be or 2,6-difluorophenyl;

when R2 and R6 both equal ydrogen, R3 and R4 together equal —CH=CH—CH=CH—, and R5 is nitro, then R1 cannot be phenyl or 4-chlorophenyl;

when R2 and R4 both equal hydrogen, R3 is COCH3, R5 and R6 both equal methoxy, then R1 cannot be 4-(diethylphosphonomethyl)phenyl;

when R2 is hydrogen, R3, R4 and R6 are all methyl, and R5 is hydroxy, then R1 cannot be phenyl, 4-carboxyphenyl, or 4-sulfamoylphenyl; and when R2 is hydrogen, R3, R4 and R6 are all methyl, and R5 is methoxy, then R1 cannot be 4-sulfamoylphenyl.

Unless otherwise indicated, all chemicals were purchased from Aldrich Chemicals (Milwaukee, Wis.);

Unless otherwise indicated, all chemicals were purchased from Aldrich Chemicals (Milwaukee, Wis.);

EXAMPLE 1

Technique for Identifying Chemical Compounds that Stimulate the Growth of Bone This technique has been described in the scientific literature [Ghosh-Choudhury, N.; Windle, J; J.; Koop, B. A.; Harris, M. A.; Guerrero, D. L.; Wozney, J. M.; Mundy, G. R.; Harris, S. E.; "Immortalized Murine Osteoblasts Derived from BMP 2-T-Antigen Expressing Transgenic Mice" *Endocrinology* (1996) 137, 331–339]. These techniques are specifically incorporated herein by reference. This method may be used alone for identifying or selecting a library of candidate compounds with pharmacological activity for promoting, stimulating, or maintaining osteoblast growth, or in conjunction with the technique provided for selecting the spatially defined molecules and candidate substances that have osteoblast proliferative activity.

Immortalized murine osteoblasts (2T3 cells) containing a bone morphogenetic protein 2 (BMP-2) promoter fragment are isolated from the calvaria of transgenic mice and cloned. These 2T3 cells are reclonable and can be stably transfected with BMP-2 promoter luciferase constructs. The BMP-2 promoter activity can then be stimulated by recombinant human BMP-2 (rhRMP-2) or chemical compounds that stimulate osteoblast proliferation. Employing this BMP-2 promoter assay as an additional screening technique, the $ED_{50}$ of compounds that stimulate luciferase activity, and, by inference, osteoblast proliferation, can be further assessed. Other in vitro cellular assays for assessing the activity of screened and selected candidate compounds well known to those of ordinary skill in the art may be used instead of the above-described promoter assay and provide further measure of the compound's pharmacological activity in stimulating osteoblast proliferation. For example, a culture of osteoblast cells may be used.

2T3 cells in 10-cm tissue culture plastic plates are stably transfected with 10 micrograms of plasmid containing luciferase reporter gene driven by −2736/114 bp of BMP-2 promoter and 1 microgram of pSV2neo plasmid for G418-resistant clone selection.

The transfection is carried out by the calcium phosphate precipitation technique. The stable clonal cell lines are generated using MEM containing 7% FCS and 200 micrograms/mL G418. Luciferase enzyme activity can be measured in 15 different clonal cell lines. One cell line (2T3-BMP-2-LUC) is chosen here because using it assays for luciferase have shown little variability over 20 passages. For a control group, a stable clonal cell line (2T3-basic LUC) is established as above, using the promoterless luciferase vector, pGL2basic (Promega Corp., Madison, Wis.) in the place of the BMP-2 promoter luciferase plasmid. Both cell lines are plated in 35-mm tissue culture dishes and treated with 0, 2, 5, 10, and 20 nanograms/mL rhBMP-2 for 48 hr in MEM containing 2% FCS. Each concentration of rhBMP-2 is used in triplicate and each experiment repeated three times. Luciferase activity is measured using a kit from Promega and a luminometer.

EXAMPLE 2

Production of Multi-Gram Amounts of 2-(2-Methoxybenzoylamino)Benzthiazole

The present example sets forth a method whereby the benzthiozole compounds may be obtained. However, other methods may be used in the practice of the present invention. A solution of 4.5 g of 2-aminobenzthiazole in 40 mL of dichloromethane and 10 mL of pyridine was cooled in an ice bath. To this cooled solution was slowly added a solution of 2-methoxybenzoyl chloride in 10 mL of dichloromethane. The resulting mixture was stirred for 3 hours while the ice bath slowly warmed to room temperature. The reaction mixture was diluted with 200 mL of ethyl acetate and washed with 1 N HCl (2×50 mL), saturated $NaHCO_3$ (1×40 mL), and saturated NaCl (1×50 mL). After drying over $Na_2SO_4$, the solution containing the crude product was filtered and evaporated to dryness. The resulting 8.0 g of white solid was recrystalized from ethyl acetate to afford 4.0 g of 2-(2 methoxybenzoylamino)benzthiazole as white crystals, mp 196–197° C., as first crop.

Other chemical synthetic techniques well known to those of skill in the art may be used such as that described in Kamala et al. (Indian *J. Chem.* (1983), 22B, 1194–96) and Waisser et al. (Collect. Czech. *Chem. Commun.* (1991), 56, 2978–2985) and the attached list of references which are hereby incorporated by reference in their entirety.

EXAMPLE 3

General Method for the Evaluation of Pharmacologically Active Compounds—Anti Tumor Activity Cell Culture Murine B16 melanoma cell line are grown in RPMI 1640 medium supplemented with 10% heat-inactivated fetal bovine serum, 2 mM L-glutamine, 50 units/ml penicillin, 50 μg/ml streptomycin, 25 μg/ml gentamycin, 0.75% sodium bicarbonate, 10 mM HEPES buffer (pH 7.4), and 0.06 mg/ml AntiPPLO. Murine P388 leukemic cell line and human HT-29 colon adenocarcinoma line are to be maintained in RPMI 1640 medium supplemented with 10% heat-inactivated fetal bovine serum. P388/CPT (camptothecin resistant cell line) was maintained in RPMI-1640 medium supplemented with 20% heat-inactivated fetal bovine serum, 10 μM β-mercaptoethanol, 10 MM L-glutamine, 100 IU/ml penicillin, 100 μg/ml streptomycin, and 50 μg/ml gentamycin. MCF-7M human breast adenocarcinoma was maintained in IMEM medium supplemented with 5% non heat-inactivated fetal bovine serum and 1 nM insulin.

In vitro Growth Inhibitory Activity

Exponentially growing cells ($1-2\times10^3$ cells, unless specified otherwise) in 0.1 ml medium were seeded on day 0 in a 96-well microtiter plate. On day 1, 0.1 ml aliquots of medium containing graded concentrations of test analogs were added in duplicate to the cell plates. After incubation at 37° C. in a humidified incubator for 3 days (P388, P388/CPT, B16) or 6 days (HT-29, MCF-7M), the plates are centrifuged briefly and 100 μl of the growth medium is removed. Cell cultures are incubated with 50 μl of 3-(4,5-, dimethylthiazol-2-yl)-2,5-diphenyl-tetrazolium bromide [MTT, 1 mg/ml in Dulbecco's phosphate buffered saline (PBS)] for 4 hr at 37° C. The resulting purple formazan precipitate is solubilized with 200 μl of 0.04 N HCl in isopropyl alcohol. Absorbance was monitored in a BioRad Model 3550 Microplate Reader at a test wavelength of 570 nm and a reference wavelength of 630 nm. The absorbance is transferred to a PC 486 computer. The $IC_{50}$ values are determined by a computer program (EZ-ED50) that fits all of the data to the following four-parameter logistic equation:

$$Y = \frac{A_{max} - A_{min}}{[1 + (X/IC_{50})]^n} + A_{min}$$

where $A_{max}$ is the absorbance of control cells, $A_{min}$ is the absorbance of cells in the presence of highest agent concentration, Y is the observed absorbance, X is the agent concentration, $IC_{50}$ is the concentration of agent that inhibits the cell growth by 50% of control cells (based on the absorbance) and n is the slope of the curve.

EXAMPLE 4

Synthesis of Pharmacologically Active Compound From Anthrone

The present example demonstrates the synthesis of a pharmacologically active compound from anthrone, a compound that was found to have reduced pharmacological activity as determined through an assay for BMP-2 promoter activity. To 6.9 grams of 4-isopropoxy benzoic acid (commercially available from Aldrich) in a round-bottom flask connected to a reflux condenser fitted with drying tube filled with calcium chloride was added 20 mL of thionyl chloride. The resulting mixture was heated to reflux for 30 min and the excess thionyl chloride removed under reduced pressure. The remaining liquid was mixed with 20 mL of freshly distilled benzene and treated dropwise with 2.79 mL of diethylamine. An additional 20 mL of benzene was added, and the resulting mixture heated to reflux for one hour. After cooling to room temperature, the reaction mixture was diluted with ethyl acetate and washed with 1% HCl (2×50 mL), 5% NaOH (3×50 mL), 1% HCl (2×50 mL), 5% NaOH (1×50 mL), and brine (1×50 mL). The resulting organic solution was dried over $MgSO_4$, filtered and evaporated to afford 6.22 g of N,N-diethyl-4-i -propoxybenzamide as a colorless oil. A solution of this material and TMEDA (4.8 mL) in THF in a round-bottomed flask under argon was cooled to −78° C. and a solution of s-BuLi in hexanes, (30.5 mL, 1.3 M) was added slowly. The reaction mixture was stirred an additional hour at −78° C., then a cooled (−78° C.) solution of freshly distilled benzaldehyde (3.58 g) in THF was added. The reaction mixture was slowly allowed to warm to room temperature over 12 hours. The reaction mixture was treated with saturated aqueous $NH_4Cl$ (50 mL) and 1% HCl (20 mL) and extracted with ethyl acetate (3×50 mL). The combined organic layers were washed with a solution prepared from equal volumes of saturated $NH_4Cl$ and 1% HCl (1×50 mL) and brine (3×50 mL). The organic layer was dried over $Na_2SO_4$, filtered and evaporated. The residue was dissolved in 200 mL of toluene and 1 g of TsOH was added. The reaction mixture was heated to reflux for 20 hours. After cooling to room temperature, the reaction mixture was diluted with ethyl acetate (200 mL) and washed with 5% $K_2CO_3$ (3×50 mL), 1% HCl (2×50 mL), saturated $NH_4Cl$ (1×50 mL), and brine (2×50 mL). The organic layer was dried over $MgSO_4$, filtered and evaporated. The residue was recrystalized from ethyl acetate/hexanes to afford 5.0 g of lactone as colorless needles: $^1H$ NMR ($CDCl_3$) δ1.27 (d, J=7.8 Hz, 6H), 4.56 (hept, J=7.8 Hz, 1H), 6.26 (s, 1H), 6.67 (s, 1H), 6.95 (d, J=10.8 Hz, 1H), 7.25 (m, 5H), 7.79 (d, J=10.8 Hz, 1H). This material was dissolved in acetic acid and treated with 500 mg of 10% Pd on carbon under an atmosphere of hydrogen. The reaction mixture was heated to 85° C. for 2 hours. After cooling to room temperature, the catalyst was removed by filtration, and the solvent evaporated. The residue was dissolved in toluene (50 mL) and the solvent evaporated. The residue was dissolved in chloroform (25 mL) and treated with trifluoroacetic anhydride (2.5 mL) at room temperature overnight. The solvent was removed and the product recrystalized from ethyl acetate to afford 2.27 g of 3-i-propoxyanthrone as white crystals, mp 123–124° C. $^1H$ NMR ($CDCl_3$) δ1.29 (d, J=7.8 Hz, 6H), 4.42 (s, 2H), 4.53 (hept, J=7.8 Hz, 1H), 6.63 (d, J=3.4 Hz), 6.73 (dd, J=3.4, 10.8 Hz, 1H), 7.20 (m, 4H), 8.04 (d, J=10.8 Hz, 1H); $^{13}C$ NMR ($CDCl_3$) δ21.86, 39.93, 69.90, 112.50, 118.72, 119.93, 125.93, 128.30, 128.41, 129.08, 134.36, 140.64, 161.66, 172.45, 193.78; HRMS (CI) $MH^{30}$ ($C_{17}H_{17}O_2$) Found 253.1208, Calc'd. Oxyanthrone was converted to a material with increased pharmacological activity by three different methods:

Method 1: The crystalline material was placed in a glass vial and heated by placing the vial on a 250° C. hot plate for 1–10 minutes.

Method 2: The 3-i-propoxyanthrone was dissolved in toluene and heated in a sealed tube in a 310° C. oil bath for 14 hours. Evaporation of the solvent afforded the active material.

Method 3: A solution of 159 mg of 3-i-propoxyanthrone in acetic acid (25 mL) was treated with chromium trioxide (180 mg) at room temperature. After 20 hours, the acetic acid was removed under reduced pressure and the residue extracted with ethyl acetate. The organic solution was washed with 5% $Na_2CO_3$ (2×30 mL) and brine (2×30 mL) and then dried over $MgSO_4$. Filtration and evaporation afforded a residue that was subjected to chromatography ($SiO_2$, 8:1 hexanes/ethyl acetate) to afford a fraction consisting mainly of one spot by thin-layer chromatography ($SiO_2$, 3:1 hexanes/ethyl acetate, $R_f$~0.6).

EXAMPLE 5

Cell Differentiation Assay

This method will be used to select spatially defined candidate compounds useful in stimulating osteoblast proliferation and enriching a population of cells for osteoblasts. Eckhardt, S. G.; Dai, A; Davidson, K. K.; Fprseth, B. J.; Wahl, G. M.; Von Hoff, D. D in *Proc. Nat'l Acad. Sci. USA* (1994), 91, 6674–6678 which is hereby incorporated by reference, details the proliferation assay.

HL60 promyelocytic leukemia cells were grown in RPMI 1640 medium with 10% fetal bovine serum and 2 mM glutamine. Various compounds were added on day 0 of each culture at the concentrations indicated and was replaced each time the cells were passaged. All cells were passaged to maintain a density of <2 million cells per mL. Differentiation was assessed using a functional assay for mature myelocytes. For nitroblue tetrazolium reduction, 300,000 cells were suspended in 0.2 mL of RPMI 1640 medium supplemented with 10% fetal bovine serum and incubated for 20 min at 37° C. with an equal volume of 0.1% nitroblue tetrazolium (Sigma) and 50 ng of freshly diluted phorbal 12-myristate 13-caetate (Sigma). Cytospin slides were prepared and counted for the percentage of cells containing intracellular reduced blue-black formazan deposits by counting at least 500 cells and correcting for viability.

EXAMPLE 6

Retinoic Acid Displacement Assay

This method is the same as that taught by Eyrolles, L.; Kagechika, H.; Kawachi, E.; Fukasawa, H.; Iijima, T.; Matsushima, Y. Hashimoto, Y.; Shudo, K. J. *Med. Chem.* (1994), 37, 1508–1517 which is hereby incorporated by reference. The cells employed in this assay can be the same as those used in Example 1 or can be another suitable cell line. The method may be used as an additional screening step in selecting the chemically defined molecules herein, or the spatially defined chemical molecules herein, that posses a pharmacological activity for binding a biological receptor, such as a receptor that is a nuclear hormone receptor.

Pelleted and lysed COS-1 cells are adjusted to ca 1–2 mg/mL by dilution in buffer (0.3 M KCl, 20 mM Tris-HCl, pH 8.0, 1.5 mM EDTA, 1 mM PMSF, 1 microgram/mL pepstatin, 0.1 mg/mL bacitracin, 0.1 mM leupeptin, and 0.1 mg/mL aprotinin). The suspension is homogenized with a Teflon-glass homogenizer and centrifuged at 100000 g, 4° C. The supernatant is used in the displacement assay. The supernatant is incubated in the presence of 6 nM [3H]-cis-retinoic acid (Amersham) and various concentrations of added ligand for 16 hrs at 4° C. in the dark. The incubation mixture is absorbed by suction onto a nitrocellulose membrane. The membrane is washed three times with washing buffer (20 mM Tris-HCl, pH 8.0, 0.15 M NaCl) and then with 25% ethanol in distilled water. Radioactivity that remains on the filter is measured by liquid scintillation.

EXAMPLE 7

Determination of Bone Growth

This method may be used to select spatially and/or chemically defined molecules that would have an expected utility for promoting bone growth.
Mineralization/Bone Growth Assay 2T3 cells are plated at 10,000 cells/well in a 24-well (1.5 cm diameter/well) tissue culture plate using 1.0 mL MEM containing 7% FCS. They are allowed to grow to confluency (day 0), and the medium is then changed to the differentiation medium (7% FCS in MEM containing 100 micrograms/mL of ascorbic acid and 5 mM beta-glycerophosphate). Recombinant human BMP-2 (rhBMP-2) and/or 1,25-dihydroxyvitamin D3 [1,25-(OH)2D3] are added at various concentrations to triplicate wells. Media are changed every 2–3 days. At various times (4,9,12,16 etc days), plates are fixed in 10% formalin for 20 min, washed with distilled water followed by ethanol, and air dried. The plates are then stained with Van Giesen stain (matrix-collagen) and Von Kossa stain (mineral). Mineralized bone nodules are then quantitated for average area of mineralized nodule, total number of mineralized nodules per square centimeter, and total area of mineralized nodules per square centimeter using JAVA Image Analysis Software (Jandel Scientific, Corte Madera, Calif.).

Quantitation of Multilayering (Growth) During 2T3 Bone Cell Differentiation

Duplicate 24-well plates are set up as described above. Cell number is then determined in triplicate wells at various time points as previously described. The cell layer is washed with PBS, and the cells are then incubated with 0.1–0.5 mL 0.05% trypsin-25 mM EDTA (GIBCO, Gaithersburg, Md.) at 37 C. for 10–40 min (until the cells in the wells are visibly rounded up). An equal volume of FCS is then added, and the cells are dispersed to a single cell suspension with 25 up/down strokes using a 1.0 mL automatic pipetting device. Cell number is determine using a hemocytometer.

EXAMPLE 8

Preparation of 3-Benzamidoquinoline Compounds

This method may be used to prepare a broad range of compounds of the formula IV indicated in Table 1 below. Generally, 3-aminoquinoline, in the presence of a base catalyst or acid scavenger such as pyridine, is reacted with the activated form of a particular benzoic acid derivative or analog in a suitable organic solvent. Depending upon the reaction conditions employed, a suitable isolation procedure will be used.

For example, a solution of 3-aminoquinoline (40 mg, 0.28 mmol) in methylene chloride (1.0 ml) was thoroughly mixed with pyridine (25 μl). Subsequently, a slight molar excess of benzoyl chloridewas added and the reaction stirred at 25° C. for 30 min. to form the condensation product 3-benzamidoquinoline in acceptable yield.

Table 1 below summarizes some of the compounds of the formula IV made according to this example. The reaction yields are based upon 0.56 mmol of 3-aminoquinoline. These compounds are exemplary of the compounds and synthetic methods of the invention and should not be taken to limit the entire scope to which the present inventor is entitled.

TABLE 1

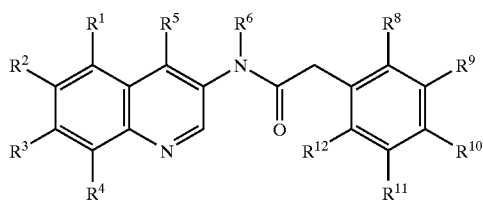

Formula IV
For the present compounds in Table 1, $R^1$, $R^2$, $R^3$, $R^4$, $R^5$ and $R^6$ are all hydrogen. The remaining substituents are defined below.
The yield of each compound is also indicated.

| Compound | $R^8$ | $R^9$ | $R^{10}$ | $R^{11}$ | $R^{12}$ | Yield (%) |
|---|---|---|---|---|---|---|
| A1 | —OMe | H | H | H | H | 20 |
| B1 | H | H | phenyl | H | H | 85 |
| C1 | H | —CF$_3$ | H | —CF$_3$ | H | 78 |
| D1 | H | H | -n-Bu | H | H | 49 |
| E1 | H | H | Cl | H | H | 93 |
| F1 | H | H | —CH$_2$Cl | H | H | 91 |
| G1 | H | —CH$_2$Cl | H | H | H | 42 |
| H1 | H | —OMe | H | H | H | 91 |
| I1 | H | H | —Et | H | H | 32 |
| J1 | H | —NO$_2$ | H | H | H | 99 |
| K1 | H | H | —NO$_2$ | H | H | 97 |
| L1 | H | H | —C$_5$H$_{11}$ | H | H | 18 |
| M1 | H | H | -n-Pr | H | H | 65 |
| N1 | H | —Me | H | H | H | 80 |
| O1 | —CF$_3$ | H | H | H | H | 78 |
| P1 | H | —CF$_3$ | H | H | H | 63 |
| Q1 | H | —OMe | —OMe | —OMe | H | 93 |
| R1 | H | —CN | H | H | H | 86 |
| S1 | H | H | —CN | H | H | 99 |
| T1 | H | Cl | Cl | H | H | 97 |
| U1 | F | F | H | H | H | 94 |
| V1 | F | H | F | H | H | 87 |
| W1 | H | F | F | H | H | 98 |
| X1 | H | F | H | F | H | 96 |
| Y1 | —OMe | H | —OMe | H | H | 72 |
| Z1 | H | —OMe | —OMe | H | H | 63 |

EXAMPLE 9

Preparation of 2-Benzamido-1,3-benzthiazole Compounds

The following general procedures can be used to prepare 2-benzamido-1,3-benzthiazole compounds of the Formula V indicated in Table 2 below. Generally, 2-amino-1,3-benzthiazole, in the presence of a base catalyst or acid scavenger such as pyridine, is reacted with a particular carbocyclic acid chloride. The target 2-benzamido-1,3-benzthiazole compound can be isolated as the free base or as the alkali metal salt of the amido nitrogen.

Procedure A

A solution of 2-amino-1,3-benzthiazole (700 mg, 4.7 mmol) in methylene chloride (20 ml) and pyridine (800 µl) was treated with 2,4-dimethoxybenzoyl chloride and stirred at 25° C. for 30 minutes. After this time, the reaction was treated with HCl (10 ml of 5 wt %) and the resulting precipitated collected by filtration. The solid was recrystallized from methanol to give 2-(2,4-dimethoxylbenzamido)-1,3-benzthiazole as colorless needles. (1.185 mg, 80% yield)

Procedure B, Alkali Metal Salt Form

A solution of 2-amino-1,3-benzthiazole (40 mg, 0.27 mmol) in methylene chloride (1 ml) and pyridine (100 µl) was treated with 4-n-butylbenzoyl chloride and stirred at 25° C. for 30 minutes. After this time, the reaction was treated with NaOH (0.5 ml, 5.0 M) and the resulting mixture stirred overnight. The resulting precipitate was collected by filtration and recrystallized from water to give 2-(4-n-butylbenzamido)-1,3-benzthiazole as pale yellow needles. (47 mg, 53%)

Table 2 below summarizes some of the compounds of the formula V made according to this example. The reaction yields are based upon 0.53 mmol of 2-amino-1,3-benzthiazole. These compounds are exemplary of the compounds and synthetic methods of the invention and should not be taken to limit the entire scope to which the present inventor is entitled.

TABLE 2

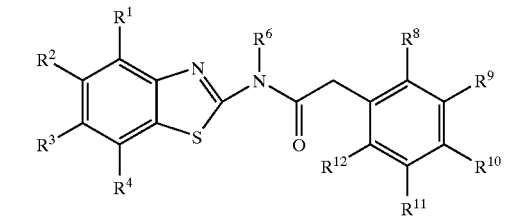

Formula V
For the present compounds in Table 2, $R^1$, $R^2$, $R^3$, $R^4$, and $R^6$ are all hydrogen. The remaining substituents are defined below.
The yield of each compound is also indicated.

| Compound | $R^8$ | $R^9$ | $R^{10}$ | $R^{11}$ | $R^{12}$ | Yield (%) |
|---|---|---|---|---|---|---|
| A2 | —OMe | H | H | H | H | 36 |
| B2 | H | H | —OMe | H | H | 94 |
| C2 | H | H | phenyl | H | H | 30 |
| D2 | H | —CF$_3$ | H | —CF$_3$ | H | 63 |
| E2 | H | H | H | H | H | 29 |
| F2 | H | H | n-Bu | H | H | 53 |
| G2 | H | H | t-Bu | H | H | 82 |
| H2 | H | H | Cl | H | H | 53 |
| I2 | H | H | —CN | H | H | 69 |
| J2 | H | Cl | Cl | H | H | 62 |
| K2 | F | F | H | H | H | 79 |
| L2 | —OMe | H | —OMe | H | H | 80 |
| M2 | H | —OMe | H | —OMe | H | 23 |
| N2 | H | H | Et | H | H | 44 |
| O2 | H | Me | H | H | H | 44 |

EXAMPLE 10

Preparation of 2-(cyclohexylamido)-1,3-benzthiazole

The present compound was prepare according to procedure B of Example 9. This compound is representative of compounds of the formula III:

W—L—Y    formula III wherein Y is a carbocyclic, more particularly a cyclohexyl, group. In this particular example, the target compound was isolated in 66% yield.

The above provides a detailed description of particular embodiments of the invention. It is recognized that departures from the disclosed embodiments may be made within the scope of the invention and that obvious modifications will occur to a person skilled in the art, and are intended to be within the scope of the present invention. The full scope of the invention is set out in the claims that follow and their equivalents. Accordingly, the claims and specification should not be construed to unduly narrow the full scope of protection to which the invention is entitled. Those of skill in the art should, in light of the present disclosure, appreciate that many changes can be made in the specific embodiments where are disclosed herein and still obtain a like or similar result without departing from the spirit and scope of the invention. All of the compositions and methods disclosed and claimed herein can be made and executed without undue experimentation in light of the present disclosure. It will be apparent that certain compounds which are both physiologically and chemically related may be substituted for the pharmacologically active compounds described herein while the same or similar results are achieved.

REFERENCES

The following references, to the extent that they provide exemplary procedural or other details supplementary to those set forth herein, are specifically incorporated herein by reference.

99647—Z Benzamid—and 2-anilinobenzothiazoles, Donche, et al. (1970) Ger. Offen. 2, 133,649.
Ghosh-Choudhury, N; Windle, J.; Koop, B. A.; Harris, M. A.; Guerrero, D. L.; Wozney, J. M.; Mundy, G. R.; Harris, S. E.; (1996) Endocrinology, 137:331–339.
J. Rosen, A. Day, T. K. Jones, E. T. Turner Jones, A. M. Nadzan and R. B. Stein, *J. Med. Chem.* (1995), 38(25), 4855–4874.
K. Waisser, J. Kunes, Z. Odlerova, Collect. Czech. *Chem. Comm.* 1991, 56, 2978–2985.
K. Kamala, P. J. Rao, K. K. Reddy, *Indian J. Chem.* 1983, 22B, 1194–1196.
M. R. Kirshenbaum, S-F. Chen, C. H. Behrens, L. M. Papp, M. M. Stafford, J-H. Sun, D. L. Behrens, J. R. Fredericks, S. T. Polkus, P. Sipple, A. D. Patten. D. Dexter, S. P. Seitz, J. L. Gross, *Cancer Res.* (1994), 54, 2199–2206.
S. G. Eckhardt, D. Dai, K. K. Davidson, B. J. Forseth, G. M. Wahl, D. D. Von Hoff, *Proc. Nat'l. Acad. Sci., USA*, (1994), 91, 6674–6679.
Vogel's Textbook of Practical Organic Chemistry, Fifth Ed., B. S. Furniss, A. J. Hannaford, P. W. G. Smith, A. R. Tatchell, New York: Wiley, 1989.
Comprehensive Organic Transformations, R. C. Larock, New York: VCH, 1989.
Organic Reactions Volumes 1–48, Editorial board, Roger Adams, editor-in-chief, Werner E. Buchmann, Louis F. Fieser (and others), New York: Wiley, 1942–1996.
Organic Syntheses Volumes 1–73, Editorial board, E. Vedejs, editor-in-chief, New York: Wiley, 1921–1996.
Protective Groups in Organic Synthesis, T. Greene, New York: Wiley, 1991.
Comprehensive Organic Chemistry Vol 1–6, chairman and deputy chairman of the editorial board, Sir Derek Barton and W. David Ollis, New York: Pergamon Press, 1979.
Comprehensive Organic Synthesis: selectivity, strategy, and efficiency in modern organic chemistry, Volumes 1–9, Barry M. Trost, Ian Fleming, editor(s), New York: Pergamon Press, 1991.
Comprehensive Organometallic Chemistry: the synthesis, reactions, and structures of organometallic compounds, Volumes 1–9, G. Wilkinson, editor, New York: Pergamon Press, 1982.
Comprehensive Heterocyclic Chemistry: the structure, reactions, synthesis and uses of heterocyclic compounds, Volumes 1–8, Alan R. Katritzky, chairman of the editorial board, New York: Pergamon, 1984.
The Chemistry of Heterocyclic Compounds Vol 1–53, New York: Wiley, 1950–1994.
Rodd's Chemistry of Carbon Compounds; a modern comprehensive treatise, Volumes 1–4, S. Coffey (ed.), New York, Elsevier Pub. Co., 1964-
Compendium of Organic Synthetic Methods, Ian T. Harrison and Shuyen Harrison, New York, Wiley-Interscience (1971-
Synthetic Methods of Organic Volumes 1–31, New York: S. Karger, 1951–1981.
Annual Reports in Organic Synthesis, New York: Academic Press, 1970–1995.
Advanced Organic Chemistry, 3rd Edition, J. March, Wiley: New York, 1985.
U.S. Pat. No. 5,322,847—Marfat et al. (1994)
Marfat et al. (1992), Chemical Abstracts, Vol. 117: 782, Abst. #90279j.
JP Patent No. 03130216 A2—Soda et al. (1991)
EP #404440 A2—Eggler et al. (1990)
EP #395093 A1—Kinoshita et al. (1990)
EP #221211 A1—Ritchey, Thomas R. (1985).

What is claimed is:
1. A method of stimulating bone growth comprising the step of:
administering to osteoblast or osteoblast precursor cells an effective amount of a compound of the formula III

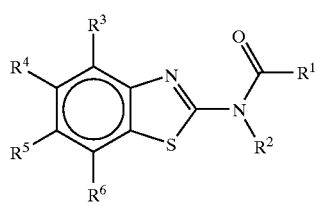

(III)

wherein:
R¹ is selected from the group consisting of:
aryl, naphthyl, cycloalkyl, cycloalkenyl, keto substituted cycloalkyl, and keto substituted cycloalkenyl, where each of the above substituents is substituted by one or more of the groups independently selected from the group consisting of:
C1–C7 alkyl, C1–C7 alkoxy, benzyloxy, hydroxy, C1–C2 haloalkyl, halo, cyano, —NO₂, —CF₃, carboxyl, hydrogen, (C1–C4) alkoxycarbonyl, —N(C1–C4 alkyl)₂, (C1–C4) alkylcarbonyloxy, aryl, (C1–C4) alkylcarbonylamino, (C1–C4)alkylcarbonyl, (C1–C4)alkyl-aryl and —NH₂;
R² is selected from the group consisting of:
H, C1–C4 alkyl, C1–C4 alkenyl, C1–C4 alkynyl, C1–C4 alkoxy and —NH₂;
R³ and R⁶ are selected from the group consisting of:
H, hydroxy, halo, (C1–C5)alkylcarbonyloxy, cyano, C1–C4 alkyl, C1–C4 alkenyl and C1–C4 alkoxy;
R⁴ and R⁵ are selected from the group consisting of:
H, halo, hydroxy, (C1–C4)alkyl-carbonyloxy, cyano, C1–C2 haloalkyl, C1–C4 alkoxy, benzoyl, (C1–C4)alkyl-aryl, (C1–C6) alkylaminocarbonyloxy, phenylaminocarbonyloxy, C1–C4 alkyl, C1–C4 alkenyl, C1–C4 alkynyl, (C1–C4)alkenyl-aryl, (C1–C4)alkynyl-aryl, (C1–C4)alkyl-(C6–C10) cycloalkyl, (C1–C4)alkenyl-(C6–C10)cycloalkyl, (C1–C4)alkynyl-(C6–C10)cycloalkyl, (C1–C4)

alkyl-(C6–C10)cycloalkenyl, (C1–C4)alkenyl-(C6–C10)cycloalkenyl, (C1–C4)alkynyl-(C6–C10)cycloalkenyl, carboxy or (C1–C4)alkoxycarbonyl.

2. The method of claim 1, wherein:

$R^3$ and $R^4$ join together to form a 5–7 membered carbocycle or oxacarbocycle fused to the ring to which they are attached, where the carbocycle or oxacarbocycle is independently substituted by one or more of the groups selected from the group consisting of:
C1–C4 alkyl, C1–C4 alkoxy, hydroxy, halo, carboxyl, hydrogen and aryl.

3. The method of claim 1, wherein:

$R^4$ and $R^5$ join together to form a 5–7 membered carbocycle or oxacarbocycle fused to the ring to which they are attached, where the carbocycle or oxacarbocycle is independently substituted by one or more of the groups selected from the group consisting of:
C1–C4 alkyl, C1–C4 alkoxy, hydroxy, halo, carboxyl, hydrogen and aryl.

4. The method of claim 1, wherein:

$R^5$ and $R^6$ join together to form a 5–7 membered carbocycle or oxacarbocycle fused to the ring to which they are attached, where the carbocycle or oxacarbocycle is independently substituted by one or more of the groups selected from the group consisting of:
C1–C4 alkyl, C1–C4 alkoxy, hydroxy, halo, carboxyl, hydrogen and aryl.

5. The method of claim 1, wherein:

$R^1$ is selected from the group consisting of:
aryl, naphthyl, and cycloalkyl, wherein each of the $R^1$ substituents is independently substituted by one or more of the groups consisting of:
C1–C7 alkyl, C1–C7 alkoxy, —NO$_2$, —CF$_3$, aryl, benzyloxy, hydroxy, C1–C2 haloalkyl, halo, cyano, carboxyl, hydrogen, aryl, (C1–C4)alkylcarbonylamino, (C1–C4)alkylcarbonyl, (C1–C4)alkyl-aryl, and —NH$_2$;

$R^2$ is H, C1–C4 alkoxy, amino, or C1–C4 alkyl;

$R^3$ and $R^6$ are independently selected from the group consisting of:
H, hydroxy, (C1–C5)alkylcarbonyloxy, cyano, C1–C4 alkyl, C1–C4 alkenyl and C1–C4 alkoxy; and $R^4$ and $R^5$ are independently selected from the group consisting of:
H, halo, hydroxy, (C1–C4)alkyl-carbonyloxy, cyano, C1–C2 haloalkyl, C1–C4 alkoxy, benzoyl, C1–C4 alkyl, C1–C4 alkenyl, C1–C4 alkynyl, (C1–C4)alkyl-aryl, (C1–C4)alkenyl-aryl, (C1–C4)alkynyl-aryl, (C1–C4)alkyl-(C6–C10)cycloalkyl, (C1–C4)alkenyl-(C6–C10)cycloalkyl, (C1–C4)alkynyl-(C6–C10)cycloalkyl, carboxy and (C1–C4)alkoxycarbonyl.

6. The method of claim 1, wherein:

$R^4$ and $R^5$ join together to form a 5–6 membered oxacarbocycle fused to the ring to which they are attached, where the carbocycle or oxacarbocycle is independently substituted by one or more substituents selected from the group consisting of:
C1–C4 alkyl, C1–C4 alkoxy, hydroxy, halo, carboxyl, hydrogen and aryl.

7. The method of claim 1, wherein:

the compound of the formula II is 2-(2-methoxybenzamido)-1,3-benzthiazole or a pharmaceutically acceptable salt thereof.

* * * * *